(12) United States Patent
Enan

(10) Patent No.: US 12,290,069 B2
(45) Date of Patent: May 6, 2025

(54) PEST CONTROL USING NATURAL PEST CONTROL AGENT BLENDS

(71) Applicant: TYRATECH, INC., Morrisville, NC (US)

(72) Inventor: Essam Enan, Davis, CA (US)

(73) Assignee: TYRATECH, INC., Morrisville, NC (US)

(*) Notice: Subject to any disclaimer, the term of this patent is extended or adjusted under 35 U.S.C. 154(b) by 0 days.

(21) Appl. No.: 18/736,009

(22) Filed: Jun. 6, 2024

(65) Prior Publication Data

US 2024/0315240 A1 Sep. 26, 2024

Related U.S. Application Data

(63) Continuation of application No. 18/512,157, filed on Nov. 17, 2023, now Pat. No. 12,035,713, which is a continuation of application No. 17/705,705, filed on Mar. 28, 2022, which is a continuation of application No. 17/454,610, filed on Nov. 11, 2021, now Pat. No. 11,896,007, which is a continuation of application No. 16/266,451, filed on Feb. 4, 2019, now abandoned, which is a continuation of application No. 15/286,110, filed on Oct. 5, 2016, now Pat. No. 10,368,543, which is a continuation of application No. 13/916,436, filed on Jun. 12, 2013, now Pat. No. 9,492,490, which is a continuation of application No. 12/936,133, filed as application No. PCT/US2009/037735 on Mar. 19, 2009, now Pat. No. 8,501,247.

(60) Provisional application No. 61/102,784, filed on Oct. 3, 2008, provisional application No. 61/043,084, filed on Apr. 7, 2008, provisional application No. 61/070,137, filed on Mar. 19, 2008.

(51) Int. Cl.

| | | |
|---|---|---|
| A01N 25/00 | (2006.01) |
| A01N 27/00 | (2006.01) |
| A01N 31/02 | (2006.01) |
| A01N 31/04 | (2006.01) |
| A01N 31/08 | (2006.01) |
| A01N 31/14 | (2006.01) |
| A01N 31/16 | (2006.01) |
| A01N 35/02 | (2006.01) |
| A01N 35/04 | (2006.01) |
| A01N 37/02 | (2006.01) |
| A01N 37/10 | (2006.01) |
| A01N 43/30 | (2006.01) |
| A01N 49/00 | (2006.01) |
| A01N 65/00 | (2009.01) |
| A01N 65/06 | (2009.01) |
| A01N 65/08 | (2009.01) |
| A01N 65/12 | (2009.01) |
| A01N 65/16 | (2009.01) |
| A01N 65/22 | (2009.01) |
| A01N 65/32 | (2009.01) |
| A01N 65/36 | (2009.01) |
| A61K 36/53 | (2006.01) |

(52) U.S. Cl.
CPC ............ *A01N 31/02* (2013.01); *A01N 25/00* (2013.01); *A01N 27/00* (2013.01); *A01N 31/04* (2013.01); *A01N 31/08* (2013.01); *A01N 31/14* (2013.01); *A01N 31/16* (2013.01); *A01N 35/02* (2013.01); *A01N 35/04* (2013.01); *A01N 37/02* (2013.01); *A01N 37/10* (2013.01); *A01N 43/30* (2013.01); *A01N 49/00* (2013.01); *A01N 65/00* (2013.01); *A01N 65/06* (2013.01); *A01N 65/08* (2013.01); *A01N 65/12* (2013.01); *A01N 65/16* (2013.01); *A01N 65/22* (2013.01); *A01N 65/32* (2013.01); *A01N 65/36* (2013.01); *A61K 36/53* (2013.01); *Y02A 50/30* (2018.01)

(58) Field of Classification Search
CPC .............................. A01N 49/00; A01N 65/00
See application file for complete search history.

(56) References Cited

U.S. PATENT DOCUMENTS

| | | |
|---|---|---|
| 3,931,306 A | 1/1976 | Hall et al. |
| 4,147,769 A | 4/1979 | Dea et al. |
| 4,415,669 A | 11/1983 | Hernandez |

(Continued)

FOREIGN PATENT DOCUMENTS

| | | |
|---|---|---|
| BE | 659040 A | 7/1965 |
| CN | 1481849 A * | 3/2004 |

(Continued)

OTHER PUBLICATIONS

Santoyo, Chemical composition and antimicrobial activity of *Rosmarinus officinalis* L. essential oil obtained via supercritical fluid extraction. Journal of food protection, (Apr. 2005) vol. 68, No. 4, pp. 790-795 (Year: 2005).*

(Continued)

*Primary Examiner* — Qiuwen Mi
(74) *Attorney, Agent, or Firm* — K&L Gates LLP

(57) ABSTRACT

According to an aspect of the present application, a composition for controlling a target pest comprises 0.1% to 4% isopropyl myristate, 0.1% to 15% thyme oil white, 0.1% to 2% geraniol, and at least one additional active ingredient selected from thymyl acetate, linalyl acetate, amyl butyrate, anise star oil, black seed oil, p-cymene, linalool, d-limonene, isopropyl myristate, lilac flower oil, methyl salicylate, alpha-pinene, piperonal, piperonyl alcohol, tetrahydrolinalool, thyme oil white, thyme oil red, thymol, vanillin, and wintergreen oil. The composition causes synergistic control of the target pest.

28 Claims, 25 Drawing Sheets

Specification includes a Sequence Listing.

(56) References Cited

U.S. PATENT DOCUMENTS

| | | | |
|---|---|---|---|
| 4,474,798 | A | 10/1984 | Inagi |
| 5,468,492 | A | 11/1995 | Szaloki et al. |
| 5,998,484 | A | 12/1999 | Zobitne et al. |
| 6,360,477 | B1 | 3/2002 | Flashinski |
| 6,610,254 | B1 | 8/2003 | Furner |
| 6,849,614 | B1 | 2/2005 | Bessette et al. |
| 7,247,647 | B2 | 7/2007 | Hughes |
| 7,294,330 | B2 | 11/2007 | Banowski et al. |
| 7,541,155 | B2 | 6/2009 | Enan |
| 7,622,269 | B2 | 11/2009 | Enan |
| 8,293,286 | B2 | 10/2012 | Nouvel |
| 8,501,247 | B2 | 8/2013 | Enan et al. |
| 8,507,013 | B2 | 8/2013 | Enan |
| 8,685,471 | B2 | 4/2014 | Enan |
| 8,691,256 | B2 | 4/2014 | Enan |
| 8,734,869 | B2 | 5/2014 | Enan |
| 8,865,230 | B2 | 10/2014 | Enan |
| 9,492,490 | B1 | 11/2016 | Enan |
| 10,368,543 | B2 | 8/2019 | Enan |
| 10,595,529 | B1 | 3/2020 | Enan |
| 11,882,839 | B2 | 1/2024 | Enan |
| 11,896,007 | B2 | 2/2024 | Enan |
| 12,035,713 | B2 | 7/2024 | Enan |
| 2003/0060379 | A1 | 3/2003 | Souter et al. |
| 2003/0194454 | A1 | 10/2003 | Bessette et al. |
| 2006/0263403 | A1 | 11/2006 | Enan |
| 2007/0020304 | A1* | 1/2007 | Tamarkin ............ A61K 8/4973 424/405 |
| 2007/0037733 | A1 | 2/2007 | Panten et al. |
| 2007/0054815 | A1 | 3/2007 | Convents et al. |
| 2007/0065527 | A1 | 3/2007 | Medvedev et al. |
| 2007/0098750 | A1 | 5/2007 | Bessette |
| 2007/0161526 | A1 | 7/2007 | Vlad et al. |
| 2007/0173423 | A1 | 7/2007 | Vermeer et al. |
| 2007/0178128 | A1 | 8/2007 | Bessette |
| 2007/0190094 | A1* | 8/2007 | Bessette ................ A01N 37/02 424/770 |
| 2007/0264297 | A1 | 11/2007 | Scialdone et al. |
| 2007/0272281 | A1 | 11/2007 | Pel |
| 2008/0047312 | A1 | 2/2008 | Hill et al. |
| 2008/0075796 | A1 | 3/2008 | Enan |
| 2008/0145462 | A1 | 6/2008 | Enan |
| 2008/0193387 | A1 | 8/2008 | de Wolff |
| 2009/0099135 | A1 | 4/2009 | Enan |
| 2009/0232918 | A1 | 9/2009 | Enan |
| 2011/0003317 | A1 | 1/2011 | Enan |
| 2011/0008471 | A1 | 1/2011 | Enan |
| 2011/0171135 | A1 | 7/2011 | Enan |
| 2013/0295153 | A1 | 11/2013 | Miresmailli et al. |
| 2014/0377385 | A1 | 12/2014 | Enan |
| 2015/0087516 | A1 | 3/2015 | Enan |
| 2015/0150838 | A1 | 6/2015 | Enan et al. |
| 2015/0201615 | A1 | 7/2015 | Schmidt et al. |
| 2015/0086656 | A1 | 12/2015 | Bailey-Jackson |
| 2016/0029625 | A1 | 2/2016 | Kennedy et al. |
| 2016/0165899 | A1 | 6/2016 | Bissinger et al. |
| 2016/0309726 | A1 | 10/2016 | Wilson |
| 2017/0318806 | A1 | 11/2017 | Kennedy et al. |
| 2018/0035674 | A1 | 2/2018 | Schmidt et al. |
| 2019/0015376 | A1 | 1/2019 | Enan et al. |
| 2019/0029253 | A1 | 1/2019 | Enan |
| 2019/0274312 | A1 | 9/2019 | Bissinger et al. |
| 2019/0320653 | A1 | 10/2019 | Enan |
| 2022/0232826 | A1 | 7/2022 | Enan |
| 2024/0016144 | A1 | 1/2024 | Schmidt et al. |

FOREIGN PATENT DOCUMENTS

| | | |
|---|---|---|
| CN | 1701663 A | 11/2005 |
| GB | 2349336 A | 11/2000 |
| JP | 10-120519 A | 5/1998 |
| JP | 2003-113392 A | 4/2003 |
| WO | WO 99/37148 A1 | 7/1999 |
| WO | WO 00/05964 A1 | 2/2000 |
| WO | WO 2006/116817 A1 | 11/2006 |

OTHER PUBLICATIONS

Diab et al, Chemical composition of Lebanese rosemary (*Rosmarinus officinalis* L.) essential oil as a function of the geographical region and the harvest time. Journal of essential oil research: JEOR (2002), vol. 14, No. 6, pp. 449-452 (Year: 2002).*
Cu et al, GC/MS analysis of star anise oil Journal of Essential Oil Research (1990), 2(2), 91-2 (Year: 1990).*
Li et al., Determination of star anise oil obtained from different extraction means. Zhongguo Liangyou Xuebao (2012), 27(11), 50-53 (Year: 2012).*
Colby, S.R., "Calculating synergistic and antagonistic responses of herbicide combinations", Weeds, 1967, vol. 15:1, pp. 20-22.
Mohagheghzadeh et al., "Volatile constituents of callus and flower-bearing tops of Zataria multiflora Boiss. (Lamiaceae)", Flavour and Fragrance Journal, 2000, 15, pp. 373-376.
Saleem et al., "Biological significance of essential oil of Zataria multiflora boiss," Natural Product Research, Dec. 2004, vol. 18, No. 6, pp. 493-497.
Stassi et al., "The Antimicrobial Activity of the Essential Oils of Four Juniperus Species Growing Wild in Greece", Flavour and Fragrance Journal, 1996, vol. 11, pp. 71-74.
Wilson et al., "Rapid Evaluation of Plant Extracts and Essential Oils for Antifungal Activity Against Botrytis cinerea", Plant Disease, 1997, vol. 81, No. 2, pp. 204-210.
Cho et al., Isolation of antifouling active pyroglutamic acid, triethyl citrate and di-n-octylphthalate from the brown seaweed *Ishige okamurae*, Journal of Applied Phycology, Oct. 2005, vol. 17, No. 5, pp. 431-435.
Environmental Protection Agency, Biochemical pesticide plant floral volatile attractant compounds: cinnamaldehyde, cinnamyl alcohol, 4-methoxy cinnamaldehyde 3-phenyl propanol, 4-methoxy phenethyl alcohol, indole, and 1,2,4-trimethoxybenzene; exemption from the requirement of a pesticide tolerance, Federal Register, vol. 59, No. 65, Apr. 5, 1994.
Isopropyl myristate, Wikipedia, first paragraph, Jun. 2, 2021, pp. 1-3.
Santoyo et al., Chemical Composition and Antimicrobial Activity of *Rosmarinus officinalis* L. Essential Oil Obtained via Supercritical Fluid Extraction, Journal of Food Protection, vol. 68, No. 4, 2005, pp. 790-795.
Diab et al., Chemical Composition of Lebanese Rosemary (*Rosmarinus officinalis* L.) Essential Oil as a Function of the Geographical Region and the Harvest Time, J. Essent. Oil Res., 14, Nov.-Dec. 2002, pp. 449-452.
Menut et al., Aromatic Plants of Tropical Central Africa. 23. Chemical Composition of Leaf Essential Oils of *Eucalyptus goniocalyx* F. Muell. and *Eucalyptus patens* Benth. Grown in Rwanda, J. Agric. Food Chem. 1995, 43, pp. 1267-1271.
Asllani et al., Chemical Composition of Albanian Thyme Oil (*Thymus vulgaris* L.) J. Essent. Oil Res., 15, May/Jun. 2003, pp. 165-167.
Politeo et al., Chemical composition and antioxidant activity of essential oils of twelve spice plants, Croatia Cehmica Acta, 2006, 79, 4, pp. 545-552.
Soliman et al., A Comparative Study of the Essential Oils from Certain *Mentha* and *Salvia* Species Grown in Egypt, Egyptian Journal of Pharmaceutical Sciences, 1997, 38, 4-6, pp. 553-561.
U.S. Appl. No. 18/543,203, filed Dec. 18, 2023.
U.S. Appl. No. 18/647,695, filed Apr. 26, 2024.
U.S. Appl. No. 18/761,935, filed Jul. 2, 2024.
Salido et al., Chemical composition and seasonal variations of rosemary oil from Southern Spain, Journal of Essential Oil Research, Jan./Feb. 2003, vol. 15, No. 1, pp. 10-14.
Sawyer Picaridin Insect Repellent Lotion, accessed on Dec. 3, 2024, 2024, pp. 1-11.

* cited by examiner

**Synergy of armor lead blend against *Ascaris suum* in culture media**

| Test agent | % as presented in the armor lead blend | Tested concentration | % kill in 10 hrs after exposure |
|---|---|---|---|
| Control (surfactant#7) | 0.12% | N/A | 0.0% |
| Armor lead blend | 100% | 10 μg/ml | 100% |
| Comp 2 | 7% | 0.7 μg/ml | 10% |
| Comp 1 | 35% | 3.5 μg/ml | 40% |
| Comp 4 | 4% | 0.4 μg/ml | 0.0% |
| Comp 3 | 30% | 3.0 μg/ml | 20% |
| carrier | 24% | 2.4 μg/ml | 10% |

FIG. 4

Acaris suum – In vitro Study by NCSU Vet School/Dr. Levy 30 min – number of worms moving out of 3/test group

| Concentration | Rx1 | Rx2 | Control 062707 |
|---|---|---|---|
| 10 mL | 0/3 | 0/3 | 3/3 |
| 1 mL | 3/3 | 3/3* | Not determined |
| 0.5 mL | 3/3 | 3/3* | Not determined |
| 0.1 mL | 3/3 | 3/3 | Not determined |

120 min – number of worms moving out of 3/test group

| Concentration | Rx1 | Rx2 | Control 062707 |
|---|---|---|---|
| 10 mL | 0/3 | 0/3 | 3/3 |
| 1 mL | 1/3 | 1/3 | Not determined |
| 0.5 mL | 3/3 | 3/3* | Not determined |
| 0.1 mL | 3/3 | 3/3 | Not determined |

320 min – number of worms moving out of 3/test group

| Concentration | Rx1 | Rx2 | Control 062707 |
|---|---|---|---|
| 10 mL | 0/3 | 0/3 | 3/3 |
| 1 mL | 0/3 | 0/3 | Not determined |
| 0.5 mL | 1/3 | 0/3 | Not determined |
| 0.1 mL | 3/3 | 3/3 | Not determined |

72 h – number of worms moving out of 3/test group

| Concentration | Rx1 | Rx2 | Control 062707 |
|---|---|---|---|
| 10 mL | --- | --- | 3/3 |
| 1 mL | --- | --- | Not determined |
| 0.5 mL | --- | --- | Not determined |
| 0.1 mL | 0/3 | 0/3 | Not determined |

FIG. 5

Prophylaxis of Blend 27 against H. nana in mouse model

| Treatment | Worm load | %Egg reduction | %cure rate |
|---|---|---|---|
| Control | 4.487 + 11.81 | | 0.0% |
| 1 mg/kg 3wks continue | 1.189 + 8.54 | 78% | 89.5% |
| 100 mg/kg 3 days continue | 0.770 + 0.16 | 94% | |
| Control | 5.720 + 12.0 | | |
| 10 mg/kg 3 wks continue | 0.400 + 2.30 | 79% | 91% |
| Control | 9.750 + 28.20 | | |
| 20 mg/kg 3 days continue | 0.070 + 0.35 | 68% | 87.8% |

Cure rate = no viable eggs/ no viable worms in treated animals as compared to controls

FIG. 8

*H. nana* in-vivo cure rate of encapsulated
Blend 27 determined based on absence of worms

| Compound | Dose | No. of mice | No. of mice negative when examined | % cure rate |
|---|---|---|---|---|
| AA100307 | 1 mg Daily | 21 | 14 | 66.7% |
| AA100307 | 3 mg Daily | 27 | 16 | 59.2% |
| AA100307 | 5 mg Daily | 24 | 17 | 70.8% |
| AA100407 | 1 mg Daily | 25 | 14 | 56.0% |
| AA100407 | 3 mg Daily | 27 | 13 | 48.1% |
| AA100407 | 5 mg Daily | 24 | 18 | 75.0% |
| AA100507 | 1 mg Daily | 24 | 16 | 66.7% |
| AA100507 | 3 mg Daily | 25 | 18 | 72.0% |
| AA100507 | 5 mg Daily | 21 | 16 | 76.2% |
| Control | infected untreated | 22 | 6 | 27.3% |

| | Chemical A (%) | Chemical B (%) | Chemical C (%) | Chemical D (%) |
|---|---|---|---|---|
| AA100307-1, zein | 4.2 | 38.1 | 14.9 | 42.8 |
| AA100407-1, shellac | 6.8 | 26.9 | 8.5 | 57.8 |
| AA100507-1, 75% s : 25% z | 5.9 | 22.0 | 7.8 | 64.4 |

FIG. 9

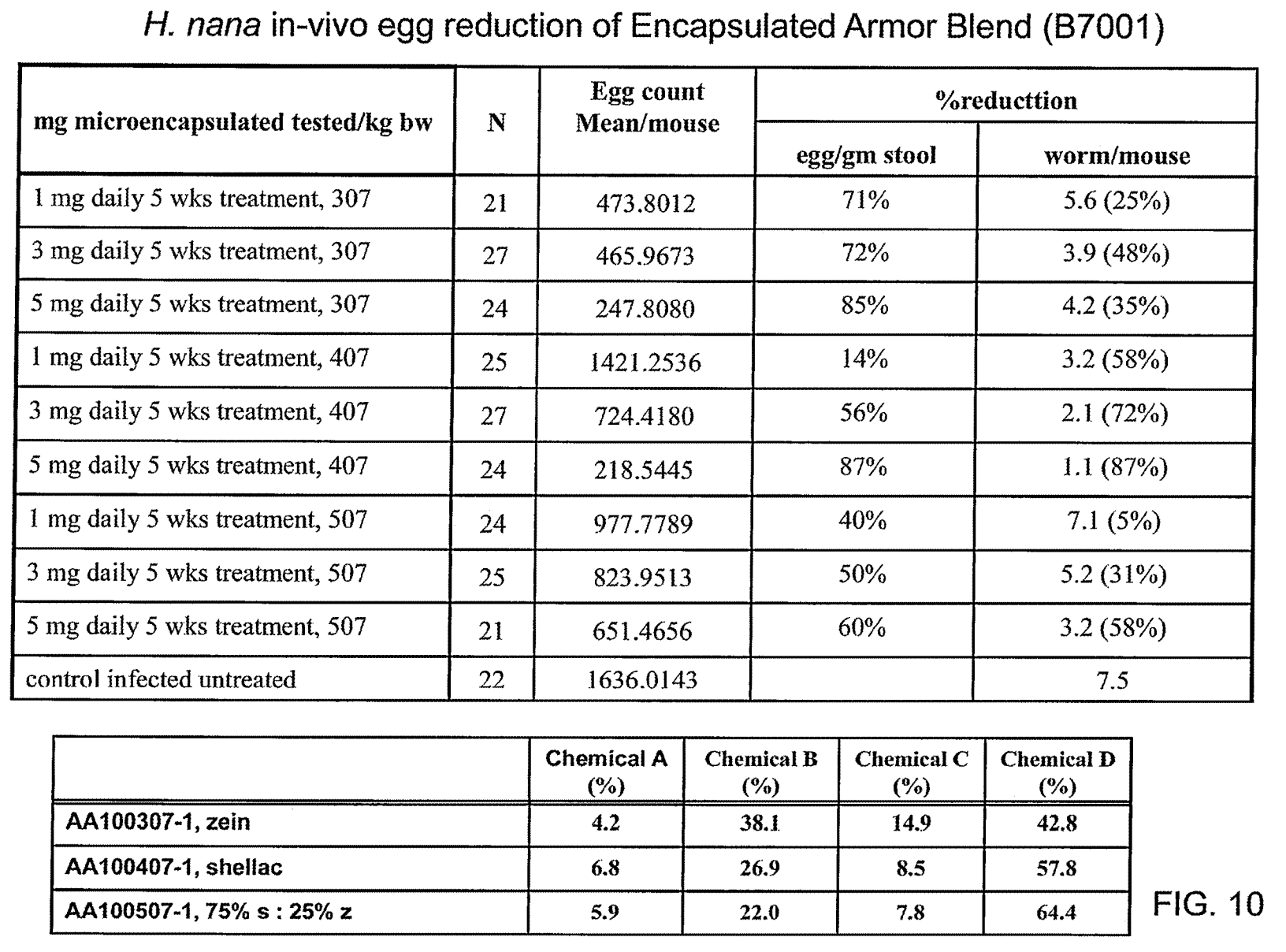

*H. nana* in-vivo egg reduction of Encapsulated Armor Blend (B7001)

| mg microencapsulated tested/kg b

Residual Activity of TyraTech 25b/4a (B5028), 25b/4b and Sergeant's Nature's Guardian Flea and Tick Squeeze-On for Pets Against *Ctenocephalides felis*, common cat flea.

| Test Surface | Test Formulation | Mortality 30 minutes after exposure to treated surface |
|---|---|---|
| Vinyl | Control (water) | 0% (N=40 insects) |
| | 25b/4a (30% Active Ingredient) B5028 | 93% ± 9.5% (N=40 insects) (100% ± 0% at 1 hour) |
| | 25b/4b (30% Active Ingredient) | 14% ± 21.6% (N=40 insects) (35% ± 15.2% at 4 hours) |
| Stainless Steel | Control (water) | 0% (N=40 insects) |
| | 25b/4a (30% Active Ingredient) | 100% (N=40 insects) |
| | 25b/4b (30% Active Ingredient) | 98% ± 4.1% (N=40 insects) (100% ± 0% at 1 hour) |
| Collagen Membrane | Control (water) | 0% (N=40 insects) |
| | 25b/4a (30% Active Ingredient) | 100% (N=40 insects) |
| | 25b/4b (30% Active Ingredient) | 100% (N=40 insects) |
| | Sergeant's Nature's Guardian Flea and Tick (22% Active Ingredient) | 100% (N=40 insects) |

FIG. 11

**Residual Activity of TyraTech Blend and Sergeant's Nature's Guardian Against *Dermacentor andersoni*.**

Residual Activity of TT Blend and Sergeant's Nature's Guardian at 2.5% and 5% on SS Panels against *D. andersoni* Ticks; 72 hours.

FIG. 15

Ectoparasites - Animal Study

| Treatment | Tested Conc. | + 2 days | | + 4 days | |
|---|---|---|---|---|---|
| | | Ticks | Fleas | ticks | fleas |
| A - Non Treatment Control | N/A | 38% | 40% | 38% | 40% |
| B - Sentry - Natural Defense C816 MSP101 | 7.4% | 80% | 94% | 82% | 94% |
| C - TyraTech HL1-30 041701-8 | 7.4% | 86% | 86% | 88% | 91% |
| D - TyraTech HL3-24 041702-08 | 7.4% | 76% | 85% | 80% | 84% |
| E - TyraTech B5028-20 041703-08 | 7.4% | 86% | 81% | 90% | 92% |
| F - TyraTech AAT-25 041704-08 | 7.4% | 86% | 83% | 84% | 95% |
| G - TyraTech AAT Plus-25 041705-08 | 7.4% | 94% | 96% | 100% | 100% |

Dogs were sprayed with 3 gm/kg bw tested materials 24 hrs prior to insect infestation

FIG. 16

TyraTech Formulation Direct Spray Efficacy Against Ticks.

| Treatment (1 ml from at Trigger Sprayer at 18 inches distance) | Kill Efficacy at 30 minutes post spray | Kill Efficacy at 4 hours post spray |
|---|---|---|
| Control (water) | 0% | 0% |
| CL17 (062006) | 100% | 100% |
| 25b/4a WB 30% | 53% | 93% |
| 25b/4b WB 30% | 44% | 54% |
| DKSH/TT 1 (100306) | 90% | 100% |
| DKSH/TT 2 (100306) | 23% | 33% |
| DKSH/TT 3 (100306) | 85% | 100% |

FIG. 20

Residual Activity of TyraTech products on Ticks When Applied to Blood Filled Membranes.

| Treatment | Mortality 30 min | Mortality 1 Hr | Mortality 2 Hr | Mortality 4 Hr |
|---|---|---|---|---|
| Water | 0% | 0% | 0% | 0% |
| 25b/4a 30% oil, (6.1% AI) 0.50ml applied | 40% | 80% | 80% | 100% |
| 25b/4b 30% oil (6.1% AI), 0.5ml applied | 80% | 100% | 100% | 100% |
| Sergeant's Nature's Guardian Natural Flea and Tick Squeeze on for dogs and puppies (25b-15 AVAO) | 40% | 40% | 80% | 80% |

N=5 Ticks per determination

FIG. 21

PEST CONTROL USING NATURAL PEST CONTROL AGENT BLENDS

CROSS REFERENCE TO RELATED APPLICATIONS

The present application is a continuation application claiming priority under 35 U.S.C. § 120 to U.S. patent application Ser. No. 18/512,157, filed Nov. 17, 2023, which in turn is a continuation application claiming priority under 35 U.S.C. § 120 to U.S. patent application Ser. No. 17/705,705, filed Mar. 28, 2022, which in turn is a continuation application claiming priority under 35 U.S.C. § 120 to U.S. patent application Ser. No. 17/454,610, filed Nov. 11, 2021, issued as U.S. Pat. No. 11,896,007, which in turn is a continuation application claiming priority under 35 U.S.C. § 120 to U.S. patent application Ser. No. 16/266,451, filed Feb. 4, 2019, now abandoned, which in turn is a continuation application claiming priority under 35 U.S.C. § 120 to U.S. patent application Ser. No. 15/286,110, filed Oct. 5, 2016, issued as U.S. Pat. No. 10,368,543, which in turn is a continuation application claiming priority under 35 U.S.C. § 120 to U.S. patent application Ser. No. 13/916,436, filed Jun. 12, 2013, issued as U.S. Pat. No. 9,492,490, which in turn is a continuation application claiming priority under 35 U.S.C. § 120 to U.S. patent application Ser. No. 12/936,133, filed Jan. 28, 2011, issued as U.S. Pat. No. 8,501,247, which in turn is a U.S. National Stage entry under 35 U.S.C. § 371 of International Application No. PCT/US2009/037735, filed on Mar. 19, 2009, designating the United States of America and published in English on Sep. 24, 2009, which in turn claims priority to each of U.S. Provisional Patent Application No. 61/070,137, filed Mar. 19, 2008, U.S. Provisional Patent Application No. 61/043,084, filed Apr. 7, 2008, and U.S. Provisional Patent Application No. 61/102,784, filed Oct. 3, 2008. The contents of each of the foregoing applications is hereby incorporated herein by reference.

FIELD OF THE INVENTION

The invention disclosed herein generally relates to synergistic compositions for controlling a target pest, and methods of using the same. In addition, embodiments of the invention are directed to methods of making and designing an improved agent for control of a target pest.

INCORPORATION BY REFERENCE OF SEQUENCE LISTING

The present application contains a Sequence Listing which has been submitted electronically in ASCII format and is hereby incorporated by reference in its entirety. Said ASCII copy, created on Jan. 3, 2024, is named TYTCH-024US4CONCON SL.xml and is 3,622 bytes in size.

BACKGROUND

Various chemicals and mixtures have been studied for pesticidal activity for many years with a goal of obtaining a product which is selective for invertebrates such as insects and has little or no toxicity to vertebrates such as mammals, fish, fowl and other species and does not otherwise persist in and damage the environment.

Most of the previously known and commercialized products having sufficient pesticidal activity to be useful also have toxic or deleterious effects on mammals, fish, fowl or other species which are not the target of the product. For example, organophosphorus compounds and carbamates inhibit the activity of acetylcholinesterase in insects as well as in all classes of animals. Chlordimeform and related formamidines are known to act on octopamine receptors of insects but have been removed from the market because of cardiotoxic potential in vertebrates and carcinogenicity in animals and a varied effect on different insects. Other compounds, which can be less toxic to mammals and other non-target species, are sometimes difficult to identify.

SUMMARY OF THE INVENTION

Embodiments of the invention relate to a composition for controlling a target pest, wherein the composition includes at least two active ingredients selected from the group consisting of thymyl acetate, linalyl acetate, amyl butyrate, anise star oil, black seed oil, p-cymene, geraniol, isopropyl myristate, d-limonene, linalool, lilac flower oil, methyl salicylate, alpha-pinene, piperonal, piperonyl alcohol, tetrahydrolinalool, thyme oil white, thyme oil red, thymol, vanillin, and wintergreen oil, wherein the composition causes synergistic control of the target pest.

In some embodiments, the target pest is an endoparasite, and the composition includes at least two active ingredients selected from the group consisting of alpha-pinene, thymol, para-cymene, linalool, thymyl acetate, and linalyl acetate. In some embodiments, the composition includes at least three active ingredients selected from the group. In some embodiments, the composition includes alpha-pinene, thymol, para-cymene, and linalool. In some embodiments, the composition includes alpha-pinene, para-cymene, thymyl acetate, and linalyl acetate.

In some embodiments, the endoparasite is a flatworm. In some embodiments, the flatworm is *Hymenolepis nana*.

In some embodiments, the endoparasite is a roundworm. In some embodiments, the roundworm is *Ascaris suum* or *Toxocara canis*.

In some embodiments, where alpha-pinene is present in the composition in an amount within a range of 1-10%, the composition includes thymol or thymol acetate in an amount within a range of 20-75%, para-cymene in an amount within a range of 2%-50%, and linalool or linalyl acetate in an amount within a range of 3%-40%. These percentages can be in terms of weight percentage or in volume percentage.

In some embodiments, where alpha-pinene is present in the composition in an amount within a range of 4%-8%, the composition includes thymol or thymol acetate in an amount within a range of 30-65%, para-cymene in an amount within a range of 4%-40%, and linalool or linalyl acetate in an amount within a range of 6%-30%. These percentages can be in terms of weight percentage or in volume percentage.

In some embodiments, the active ingredients are encapsulated using an encapsulating agent. In some embodiments, the encapsulating agent is selected from the group consisting of zein and shellac, or a combination thereof.

In some embodiments, the target pest is an ectoparasite, and the composition includes at least two active ingredients selected from the group consisting of amyl butyrate, anise star oil, black seed oil, p-cymene, geraniol, isopropyl myristate, d-limonene, linalool, lilac flower oil, methyl salicylate, alpha-pinene, piperonal, piperonyl alcohol, tetrahydrolinalool, thyme oil white, thyme oil red, thymol, vanillin, and wintergreen oil.

In some embodiments, the ectoparasite is at least one selected from the group of: a flea, a tick, a mosquito, a thrip, and a fly. In some embodiments, the ectoparasite at least one selected from the group consisting of *Ctenocephalides felis*,

*Dermacentor andersoi, Rhipicephalus sanguineus, Aedes aegypti,* and *Stomoxys calcirans.*

In some embodiments, the at least two active ingredients are selected from the group consisting of geraniol, d-limonene, linalool, piperonal, tetrahydrolinalool, and vanillin. In some embodiments, where geraniol is present in the composition within a range of 3%-30%, the composition includes d-limonene in an amount within a range of 7%-30%, linalool in an amount within a range of 4%-20%4, piperonal in an amount within a range of 2%-25%, tetrahydrolinalool in an amount within a range of 6%-22%, and vanillin in an amount within a range of 0.3%-1.5%. These percentages can be in terms of weight percentage or in volume percentage.

In some embodiments, the at least two active ingredients are selected from the group consisting of amyl butyrate, anise star oil, and thyme oil white. In some embodiments, where amyl butyrate is present in the composition within a range of 15%-30%, the composition includes anise star oil in an amount within a range of 40%-65%, and thyme oil white in an amount within a range of 15%-30%. These percentages can be in terms of weight percentage or in volume percentage.

In some embodiments, the at least two active ingredients are thyme oil white and wintergreen oil. In some embodiments, where thyme oil white is present in the composition within a range of 10-30%, the composition includes wintergreen oil in an amount within a range of 25%-55%. These percentages can be in terms of weight percentage or in volume percentage.

In some embodiments, the at least two active ingredients are selected from the group consisting of d-limonene, lilac flower oil, and thyme oil white. In some embodiments, where d-limonene is present in the composition within a range of 15%-35%, the composition includes lilac flower oil in an amount within a range of 30%-55%, and thyme oil white in an amount within a range of 20%-40%. These percentages can be in terms of weight percentage or in volume percentage.

In some embodiments, the at least two active ingredients are selected from the group consisting of alpha-pinene, thymol, para-cymene, and linalool. In some embodiments, where alpha-pinene is present in the composition in an amount within a range of 1-10%, the composition includes thymol in an amount within a range of 25%-45%, para-cymene in an amount within a range of 20%-35%, and linalool in an amount within a range of 2%-15%. These percentages can be in terms of weight percentage or in volume percentage.

In some embodiments, the at least two active ingredients are selected from the group consisting of d-limonene, linalool, piperonal, piperonyl alcohol, tetrahydrolinalool, and vanillin. In some embodiments, where d-limonene is present in the composition within a range of 5%-15%, the composition includes linalool in an amount within a range of 10%6-25%, piperonal in an amount within a range of 15%-30%, piperonyl alcohol in an amount within a range of 5%-15%, tetrahydrolinalool in an amount within a range of 10%-30%, and vanillin in an amount within a range of 0.5%-5%. These percentages can be in terms of weight percentage or in volume percentage.

In embodiments of the invention, an antiparasitic formulation is provided, wherein the antiparasitic formulation includes the composition of any of the foregoing, and wherein the composition is present within a range of 1%-30%, with the balance of the formulation containing a solvent or surfactant.

Embodiments of the invention also relate to a method of treating a parasitic infestation in a subject, wherein the method includes administering to the subject an effective amount of any of the foregoing compositions or an antiparasitic formulations that contains any of the foregoing compositions.

Embodiments of the invention can also relate to the use of any of the foregoing compositions for the manufacture of a medicament for treating or preventing parasitic infection.

In embodiments of the invention, a pharmaceutical composition is provided, wherein the pharmaceutical composition contains a pharmaceutically adequate carrier or diluent and a sufficient amount of any of the foregoing compositions.

Embodiments of the invention are directed to a method of making an improved agent for control of a target pest, the method including: providing a complex agent comprising a plurality of fractions; isolating at least a first fraction of the agent; screening the first fraction using a screening system containing at least one invertebrate receptor to obtain a first screening result; comparing the first screening result with a second screening result, wherein the second screening result includes an outcome of a screening of the complex agent against the at least one invertebrate receptor, and wherein the first and second screening results are indicative of a potential activity against the target pest; and changing a characteristic of the complex agent, thereby making the improved agent, wherein the changing is based upon information obtained from at least one of the screening step and the comparing step.

In some embodiments, the first screening result includes a value that is higher than that of the second screening result, and the changing includes increasing a relative amount of the first fraction.

In some embodiments, the first screening result includes a value that is lower than that of the second screening result, and the changing includes decreasing a relative amount of the first fraction.

In some embodiments, the first fraction can include a single active ingredient.

In some embodiments, the changing step includes: obtaining a chemical analog or derivative of the active ingredient; screening the analog or derivative against the invertebrate receptor, wherein the screening results are indicative of potential activity against the target pest, thereby identifying an active analog or derivative of the active ingredient. In some embodiments, the changing step can further include combining the active analog or derivative with the complex agent.

In some embodiments, the chemical analog or derivative is a chemical analog that is an isomer of the active ingredient. In some embodiments, the chemical analog or derivative is a chemical derivative of the active ingredient.

In some embodiments, the chemical derivative of the active ingredient is an organic-group containing derivative of the active ingredient.

In some embodiments, the chemical derivative of the active ingredient is alkylated derivative of the active ingredient. In some embodiments, the alkylated derivative is a methylated, ethylated, propylated, butylated, cerylated, decylated, heptylated, hexylated, myricylated, myristyl, nonlyated, octylated, palmitylated, pentylated, stearylated, isopropylated, isobutylated, lignocerylated, pentacosylated, heptacosylated, montanylated, nonacosylated, pentan-2-ylated, isopentylated, 3-methylbutan-2-ylated, tert-pentylated, neopentylated, undecylated, tridecylated, pentadecylated, margarylated, nonadecylated, arachidylated, henicosylated, behenylated, tricosylated, cyclobutyl, or cyclopropyl derivative.

In some embodiments, the chemical derivative of the active ingredient is an arylated derivative of the active ingredient. In some embodiments, the arylated derivative is a phenylated or biphenyl-4-ylated derivative.

In some embodiments, the chemical derivative of the active ingredient is a halogenated derivative of the active ingredient. In some embodiments, the halogenated derivative of the active ingredient is a fluorinated, chlorinated, brominated, or iodinated derivative of said active ingredient.

In some embodiments, the chemical derivative of the active ingredient is an alkenylated derivative. In some embodiments, the alkenylated derivative is an oleylated, allylated, isopropenylated, vinylated, prenylated, or phytylated derivative.

In some embodiments, the chemical derivative of the active ingredient is a hydroxylated derivative of the active ingredient. In some embodiments, the chemical derivative of the active ingredient is a thiolated derivative of the active ingredient. In some embodiments, the chemical derivative of the active ingredient is a carboxylated derivative of the active ingredient. In some embodiments, the chemical derivative of the active ingredient is an amidated derivative of the active ingredient. In some embodiments, the chemical derivative of the active ingredient is an aminated derivative of the active ingredient. In some embodiments, the chemical derivative of the active ingredient is an esterified derivative of the active ingredient. In some embodiments, the chemical derivative of the active ingredient is an acylated derivative of the active ingredient. In some embodiments, the chemical derivative of the active ingredient is a sulfonated derivative of the active ingredient.

In some embodiments, the changing step further includes identifying a second active analog or derivative of an active ingredient and combining the active analog or derivative with the second active analog or derivative. In some embodiments, the changing step further includes combining the active analog or derivative of the active ingredient with an active ingredient of the complex agent. In some embodiments, the changing step further includes combining the active analog or derivative of the active ingredient with a second complex agent. In some embodiments, the changing step further includes combining the active analog or derivative of the active ingredient with an active ingredient identified in a second complex agent. In some embodiments, the changing step further includes combining the active analog or derivative of the active ingredient with an active analog or derivative of an active ingredient identified in a second complex agent. In some embodiments, the changing step further includes combining the active analog or derivative of the active ingredient with a fraction of the complex agent.

In some embodiments, the first fraction can contain a plurality of ingredients.

In some embodiments, the method further includes isolating a second fraction from said complex agent, wherein the changing of a characteristic of the complex agent includes combining the first and second fractions.

In some embodiments, the changing of a characteristic of the complex agent includes combining the first fraction with a second complex agent.

In some embodiments, the method further includes the steps of: isolating at least a third fraction from the first fraction; screening the third fraction in a second screening step using said screening system to obtain a third screening result; comparing the third screening result with a fourth screening result in a second comparing step, wherein the fourth screening result includes an outcome of a screening of the improved agent against at least one invertebrate receptor, and wherein the third and fourth screening results are indicative of a potential activity against the target pest; and changing a characteristic of the improved agent to make a further improved agent, wherein the changing is based upon information obtained from at least one of the second screening step and the second comparing step.

In some embodiments, the changing of a characteristic of the complex agent includes combining the first fraction with a fraction of a second complex agent.

Embodiments of the invention also relate to an improved agent that is potentially active against a target pest, wherein the improved agent contains at least one modification as compared to a starting agent, and wherein the modification produces a change in activity with respect to the activity of said starting agent, and wherein the activity includes an activity upon at least one invertebrate receptor, and wherein activity upon the receptor is indicative of potential activity against the target pest.

In some embodiments, the starting agent is a complex agent. In some embodiments, the starting agent is a fraction of a complex agent.

In some embodiments, the change in activity with respect to the activity of the starting agent is an increase in activity.

BRIEF DESCRIPTION OF THE DRAWINGS

Those of skill in the art will understand that the drawings, described below, are for illustrative purposes only. The drawings are not intended to limit the scope of the present teachings in any way.

FIG. 1 is a graph illustrating Ca2+ mobilization in cells expressing a Drosophila tyramine receptor in response to treatment with Blend 27.

FIG. 2 is a graph illustrating shows Ca2+ mobilization in cells expressing a Drosophila tyramine receptor in response to treatment with Blend 27 or individual components of Blend 27, all administered at 0.5 mg/mL.

FIG. 3 illustrates Ca2+ mobilization in cells expressing a Drosophila tyramine receptor in response to treatment with Blend 27 ("Armor lead blend") or individual components ("Chemical A", "Chemical B", "Chemical C", "Chemical D") of Blend 27, where the individual components are administered in concentrations that reflect the % (v/v) in which they are found in Blend 27.

FIG. 4 is a table illustrating the synergistic effect of the individual components of Blend 27 ("B7001") when combined in the blend on the mortality of the endoparasite *Ascaris suum*.

FIG. 5 is a series of tables illustrating the in vitro effect of Blend 27 ("B7001") on the control of the endoparasite *Ascaris suum* as measured in in vitro assays.

FIG. 6 is a bar graph illustrating the synergistic effect of Components 1-5 on the cure when combined in Blend 27 on the cure rate of the endoparasite *H. nana* in animals.

FIG. 7 is a diagram showing the experimental protocol used to study the effect of Blend 27 on treating mice infected with the endoparasite *H. nana*.

FIG. 8 is a table illustrating the effect of administered amount and duration of treatment using Blend 27 for the treatment and prevention of *H. nana* infection in mice.

FIG. 9 is a table showing the in vivo cure rate of different administered doses of encapsulated formulations of Blend 27 for treatment of *H. nana* infection in mice.

FIG. 10 is a table showing the in vivo treatment (in terms of egg reduction) of different administered doses of encapsulated formulations of Blend 27 ("Armor Blend (B7001)") for treatment of *H. nana* infection in mice.

FIG. 11 is a table showing the effect of Blends 11A ("25b/4a (B5028)") and 8 ("25b/4b") on the mortality of the ectoparasite *Ctenocephalides felis* (cat flea) on different test surfaces.

FIG. 15 is a bar graph illustrating the residual effect of Blend 75 ("F-4002") at different concentrations on the mortality of the ectoparasite *Dermacentor andersoni* (wood tick) at 72 hours after exposure compared to a commercial brand at the same comparison concentrations.

FIG. 16 is a table illustrating the effect of various blends on the mortality of ectoparasites *Ctenocephalides felis* (cat flea) and *Rhipicephalus sanguineus* (tick) compared to a commercial blend at the same comparison concentration.

FIG. 20 is a table illustrating the kill efficacy of various blends in spray formulation at 30 minutes and 4 hours post-exposure on ticks.

FIG. 21 is a table illustrating the residual activity of various blends compared to a commercial formulation.

DETAILED DESCRIPTION OF THE INVENTION

Figure 1:
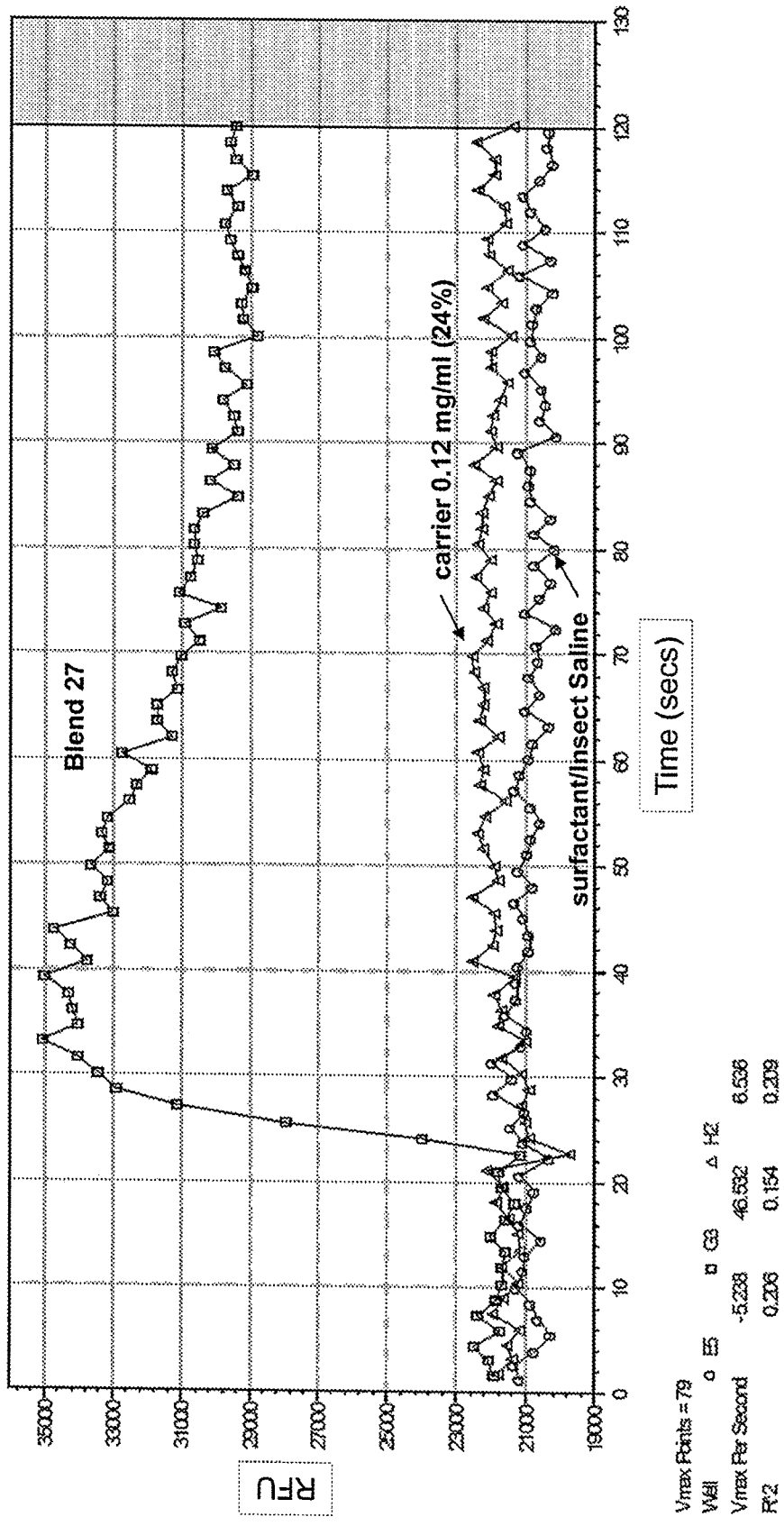

Embodiments of the present invention provide compositions for controlling a target pest.

Embodiments of the invention include compositions for controlling a target pest, which can include one or more plant essential oils and methods for using these compositions. The plant essential oils, when combined, can have a synergistic effect. The compositions also can include a fixed oil, which is typically a non-volatile non-scented plant oil. Additionally, in some embodiments, these compositions can be made up of generally regarded as safe (GRAS) compounds. In some embodiments, the composition contains at least two active ingredients selected from the group consisting of: thymyl acetate, linalyl acetate, amyl butyrate, anise star oil, black seed oil, p-cymene, geraniol, isopropyl myristate, d-limonene, linalool, lilac flower oil, methyl salicylate, alpha-pinene, piperonal, piperonyl alcohol, tetrahydrolinalool, thyme oil white, thyme oil red, thymol, vanillin, and wintergreen oil.

The target pest can be selected from, for example, the group consisting of a fungus, a plant, an animal, a moneran, a protist, and the like. The target pest can be an arthropod species, such as, for example, an insect, an arachnid, or an arachnoid. The target pest can be a species belonging to an animal order, such as, for example, Acari, Anoplura, Araneae, Blattodea, Coleoptera, Collembola, Diptera, Gryllopotera, Heteroptera, Homoptera, Hymenoptera, Isopoda, Isoptera, Lepidoptera, Mantodea, Mallophaga, Neuroptera, Odonata, Orthoptera, Psocoptera, Siphonaptera, Symphyla, Thysanura, Thysanoptera, and the like. In preferred embodiments of the invention, the target pest is a parasite. In some embodiments, the target pest is an endoparasite. In some embodiments, the target pest is an ectoparasite.

Embodiments of the invention are directed to methods of screening compositions for pest-control potential, compositions for controlling pests, and methods for using these compositions.

As used herein, "pests" can mean any organism whose existence it can be desirable to control. Pests can include, for example, bacteria, cestodes, fungi, insects, nematodes, parasites, plants, and the like.

As used herein, "pesticidal" can mean, for example, antibacterial, antifungal, antiparasitic, herbicidal, insecticidal, and the like.

For purposes of simplicity, the term "insect" shall be used in this application; however, it should be understood that the term "insect" refers, not only to insects, but also to mites, spiders, and other arachnids, larvae, and like invertebrates. Also for purposes of this application, the term "pest control" shall refer to having a repellant effect, a pesticidal effect, or both. "Repellant effect" is an effect wherein more insects are repelled away from a host or area that has been treated with the composition than a control host or area that has not been treated with the composition. In some embodiments, repellant effect is an effect wherein at least about 75% of insects are repelled away from a host or area that has been treated with the composition. In some embodiments, repellant effect is an effect wherein at least about 90% of insects are repelled away from a host or area that has been treated with the composition. "Pesticidal effect" is an effect wherein treatment with a composition causes at least about 1% of the insects to die. In this regard, an LC1 to LC100 (lethal concentration) or an LD1 to LD100 (lethal dose) of a composition will cause a pesticidal effect. In some embodiments, the pesticidal effect is an effect wherein treatment with a composition causes at least about 5% of the exposed insects to die. In some embodiments, the target pest is a non-insect, such as a parasite.

Embodiments of the invention can be used to control parasites. As used herein, the term "parasite" includes endoparasites and ectoparasites. Endoparasites include, but are not limited to, protozoa, including intestinal protozoa, tissue protozoa, and blood protozoa. Ectoparasites include, but are not limited to, roundworms, worms, ticks, fleas, lice and other organisms found on an external orifice or found on or in a skin surface.

In some embodiments, the pesticidal effect is an effect wherein treatment with a composition causes at least about 10% of the exposed pests to die. In some embodiments, the pesticidal effect is an effect wherein treatment with a composition causes at least about 25% of the pests to die. In some embodiments the pesticidal effect is an effect wherein treatment with a composition causes at least about 50% of the exposed pests to die. In some embodiments the pesticidal effect is an effect wherein treatment with a composition causes at least about 75% of the exposed pests to die. In some embodiments the pesticidal effect is an effect wherein treatment with a composition causes at least about 90% of the exposed pests to die.

In some embodiments of the invention, treatment with compositions of the invention will result in a knockdown of the target pest occurring within a few seconds to a few minutes. "Knockdown" is an effect wherein treatment with a composition causes at least about 1% to display reduced mobility. In some embodiments, the knockdown is an effect wherein treatment with a composition causes at least about 5%, 10%, 15%, 20%, 25%, 30%, 35%, 40%, 45%, or 50% of the exposed pests to die. In some embodiments, the knockdown is an effect wherein treatment with a composition causes at least about 55%, 60%, 65%, 70%, 75%, 80%, 85%, 90%, or 95% of the exposed pests to die.

The compositions of the present invention can be used to control target pest by either treating a host directly, or treating an area in which the host will be located, for example, an indoor living space, outdoor patio or garden. For purposes of this application, host is defined as a plant, human or other animal. In some embodiments, the host is an insect.

Treatment can include use of a oil-based formulation, a water-based formulation, a residual formulation, and the like. In some embodiments, combinations of formulations can be employed to achieve the benefits of different formulation types.

Embodiments of the invention are directed to compositions for controlling insects and methods for using these compositions. Compositions of the present invention can include any of the following oils, or mixtures thereof.

Embodiments of the invention are directed to compositions for controlling insects and methods for using these compositions. Compositions of the present invention can include any of the following oils, or mixtures thereof.

Exemplary Active Ingredients

Methyl salicylate, also known as betula oil. Methyl salicylate is a major component of oil of wintergreen and is sometimes referred to interchangeably with oil of wintergreen. It is a natural product of many species of plants, is the methyl ester of salicylic acid, and can be produced chemically from the condensation reaction of salicylic acid and methanol. Some of the plants producing it are called wintergreens, hence the common name. Methyl salicylate can be used by plants as a pheromone to warn other plants of pathogens (Shulaev, et al. (Feb. 20, 1997) *Nature* 385: 718-721). The release of methyl salicylate can also function as an exopheromone aid in the recruitment of beneficial insects to kill the herbivorous insects (James, et al. (August 2004) *J. Chem. Ecol.* 30(8): 1613-1628). Numerous plants produce methyl salicylate including species of the family Pyrolaceae and of the genera *Gaultheria* and *Betula*. It is noted that, where a given blend or formulation or other composition is disclosed herein as containing wintergreen oil, an alternative embodiment, containing methyl salicylate in place of wintergreen oil, is also contemplated. Likewise, where a blend or formulation of other composition includes methyl salicylate, an alternative embodiment, containing wintergreen oil, is also contemplated.

Thyme Oil is a natural product that can be extracted from certain plants, including species from the Labiatae family; for example, thyme oil can be obtained from *Thymus vulgaris* (also known as, *T. ilerdensis, T aestivus*, and *T velantianus*), generally by distillation from the leafy tops and tender stems of the plant. Two commercial varieties of Thyme oil are recognized, the 'red,' the crude distillate, which is deep orange in color, and the 'white,' which is colourless or pale yellow, which is the 'red' rectified by re-distilling. Thyme oil principally contains the phenols thymol and carvacrol, along with borneol, linalool, and cymene, and rosmarinic and ursolic acids. Where an embodiment describes the use of thyme oil white, other embodiments are specifically contemplated in which the thyme oil white is replaced by thyme oil red, thymol, carvacrol, borneol, linalool, cymene, rosmarinic acid, ursolic acid, or a mixture of any of these with each other or with thyme oil white. Particularly preferable are mixtures of thyme oil white and thyme oil red that contain 10% or less thyme oil red, more preferably 5% or less, and most preferably 1%.

Thymol is a monoterpene phenol derivative of cymene, $C_{10}H_{13}OH$, isomeric with carvacrol, found in thyme oil, and extracted as a white crystalline substance. It is also known as hydroxycymene and 5-methyl-2-(1-methylethyl) phenol. Where an embodiment describes the use of thymol, other embodiments are specifically contemplated in which the thymol is replaced by carvacrol, thyme oil white, thyme oil red, or a mixture of any of these with each other or with thyme oil white.

Black seed oil is obtained from the seeds of *Nigella sativa*. Its chief constituents are carvone, α-pinene, sabinene, β-pinene, and p-cymene, as well as the fatty acids myristic acid, palmitic acid, palmitoleic acid, stearic acid, oleic acid, linoleic acid, linolenic acid, and arachidic acid. Where an embodiment describes the use of any form of black seed oil, other embodiments are specifically contemplated in which the black seed oil is replaced by d-carvone, l-carvone, a racemic mixture of d-carvone and l-carvone, α-pinene, sabinene, β-pinene, or p-cymene, or a mixture of any of these with each other, with any of myristic acid, palmitic acid, palmitoleic acid, stearic acid, oleic acid, linoleic acid, linolenic acid, or arachidic acid or with any form of black seed oil.

Linalool is a naturally-occurring terpene alcohol chemical found in many flowers and spice plants. It is also known as 3,7-dimethylocta-1,6-dien-3-ol. It has two stereoisomeric forms: (S)-(+)-linalool (known as licareol) and (R)-(−)-linalool (known as coriandrol). Linalool can be obtained as linalool coeur (a racemic mixture, CAS number 78-70-6), or in preferred derivative forms such as tetrahydrolinalool (the saturated form), ethyl linalool, linalyl acetate, and pseudo linalyl acetate (7-octen-2-ol, 2-methyl-6-methylene:acetate). Where an embodiment describes the use of any form of linalool, other embodiments are specifically contemplated in which the linalool is replaced by licareol, coriandrol, tetrahydrolinalool, ethyl linalool, linalyl acetate, pseudo linalyl acetate, or a mixture of any of these with each other or with any form of linalool. Similarly, where an embodiment describes the use of tetrahydrolinalool, other embodiments are specifically contemplated in which the tetrahydrolinalool is replaced by licareol, coriandrol, racemic linalool, ethyl linalool, linalyl acetate, pseudo linalyl acetate, or a mixture of any of these with each other or with tetrahydrolinalool. Additionally, where an embodiment describes the use of ethyl linalool, other embodiments are specifically contemplated in which the ethyl linalool is replaced by licareol, coriandrol, tetrahydrolinalool, racemic linalool, linalyl acetate, pseudo linalyl acetate, or a mixture of any of these with each other or with ethyl linalool. Finally, where an embodiment describes the use of linalyl acetate, other embodiments are specifically contemplated in which the linalyl acetate is replaced by licarcol, coriandrol, tetrahydrolinalool, racemic linalool, ethyl linalool, pseudo linalyl acetate, or a mixture of any of these with each other or with linalyl acetate.

Geraniol, also called rhodinol and 3,7-dimethyl-2,6-octadien-1-ol, is a monoterpenoid and an alcohol. It is the primary part of oil-of-rose and palmarosa oil. It is used in perfumes and as a flavoring. It is also produced by the scent glands of honey bees to help them mark nectar-bearing flowers and locate the entrances to their hives. Geraniol can be obtained in a highly pure form as Geraniol Fine, FCC (Food Chemicals Codex grade), which is 98% minimum pure geraniol and 99% minimum nerol and geraniol. Geraniol can be also be obtained, for example, as Geraniol 60, Geraniol 85, and Geraniol 95. When Geraniol is obtained as Geraniol 60, Geraniol 85, or Geraniol 95, then about forty percent, fifteen percent, or five percent of the oil can be nerol. Nerol is a monoterpene ($C_{10}H_{18}O$), the cis-isomer of geraniol, which can be extracted from attar of roses, oil of orange blossoms and oil of lavender. Citral (3,7-dimethyl-2,6-octadienal or lemonal) is the generic name for the aldehyde form of nerol and geraniol, and can be obtained from lemon myrtly, *Litsea cubeba*, lemongrass, Lemon *verbena*, lemon balm, lemon, and orange. The E-isomer of citral is known as geranial or citral A. The Z-isomer is known as neral or citral B. Where an embodiment describes the use of any form of geraniol, other embodiments are specifically contemplated in which the geraniol is replaced by another form of geraniol (such as Geraniol Fine FCC or any geraniol/nerol mixture), nerol, geranial, neral, citral, or a mixture of any of these with each other or with any form of geraniol. Similarly, Where an embodiment describes the use of any form of citral, other embodiments are specifically contemplated in which the citral is replaced by a form of geraniol (such as Geraniol Fine FCC or any gernaiol/nerol mixture), nerol, geranial, neral, or a mixture of any of these with each other or with citral.

Vanillin (also known as methyl vanillin, vanillic aldehyde, vanilin, and 4-hydroxy-3-methoxybenzaldehyde) is the primary component of the extract of the vanilla bean. In addition to vanillin, natural vanilla extract also contains p-ydroxybenzaldehyde, vanillic acid, piperonal, and p-hydroxybenzoic acid. Synthetic vanillin is used as a flavoring agent in foods, beverages, and pharmaceuticals. Where an embodiment describes the use of vanillin, other embodiments are specifically contemplated in which the vanillin is replaced by natural vanilla extract, p-hydroxybenzaldehyde, vanillic acid, piperonal, ethyl vanillin, or p-hydroxybenzoic acid, or a mixture of any of these with each other or with vanillin.

Isopropyl myristate is the ester of isopropanol and myristic acid; it is also known as 1-tetradecanoic acid, methylethyl ester, myristic acid isopropyl ester, and propan-2-yl tetradecanoate. Where an embodiment describes the use of isopropyl myristate, other embodiments are specifically contemplated in which isopropyl myristate may be replaced by similar chemicals such as isopropyl palmitate, isopropyl isothermal, putty stearate, isostearyl neopentonate, myristyl myristate, decyl oleate, octyl sterate, octyl palmitate, isocetyl stearate, or PPG myristyl propionate, or a mixture of any of these with each other or with isopropyl myristate.

Piperonal (heliotropine, protocatechuic aldehyde methylene ether) is an aromatic aldehyde that comes as transparent crystals, $C_8H_6O_3$, and has a floral odor. It is used as flavoring and in perfume. It can be obtained by oxidation of piperonyl alcohol. Where an embodiment describes the use of piperonal, other embodiments are specifically contemplated in which piperonal may be replaced by piperonyl alcohol, 3,4-methylenedi oxybenzylamine, 3,4-methylenedioxymandelonitrile, piperonylic acid, piperonyl acetate, piperonylacetone, piperonylideneacetone, piperonyl isobutyrate, piperonyl butoxide, piperonylglycine, or protocatecheuic acid or a mixture of any of these with each other or with piperonal. Similarly, where an embodiment describes the use of piperonyl alcohol, other embodiments are specifically contemplated in which piperonyl alcohol may be replaced by piperonal, 3,4-methylenedioxybenzylamine, 3,4-methylenedioxymandelonitrile, piperonylic acid, piperonyl acetate, piperonylacetone, piperonylidenecacetone, piperonyl isobutyrate, piperonyl butoxide, piperonylglycine, or protocatecheuic acid, or a mixture of any of these with each other or with piperonyl alcohol.

The pinenes encompass the isomeric forms α-pinene and β-pinene; both are important constituents of pine resin. Important pinene derivatives include the bicyclic ketones verbenone and chrysanthone. Where an embodiment describes the use of α-pinene, other embodiments are specifically contemplated in which α-pinene may be replaced by β-pinene, verbenone, or chrysanthone, or a mixture of any of these with each other or with α-pinene. Where an embodiment describes the use of s-pinene, other embodiments are specifically contemplated in which β-pinene may be replaced by α-pinene, verbenone, or chrysanthone, or a mixture of any of these with each other or with β-pinene.

Cymene is a monoterpene-related hydrocarbon, consisting of a benzene ring substituted with a methyl group and an isopropyl group. The para-substituted form occurs naturally and is a component of oil of cumin and thyme. The ortho- and meta-substituted also exist, but are less common. Where an embodiment describes the use of p-cymene, other embodiments are specifically contemplated in which terpinolene may be replaced by o-cymene or m-cymene, or a mixture of any of these with each other or with p-cymene.

Other ingredients, including but not limited to black seed oil, borneol, camphene, carvacrol, β-caryophyllene, triethylcitrate, p-cymene, hedion, heliotropine, hercolyn D, lilac flower oil, lime oil, limonene, linalool, ethyl-linalool, tetrahydro-linanool, α-pinene, β-pinene, piperonal, piperonyl alcohol, α-terpinene, tert-butyl-p-benzoquinone, α-thujene, and triethyl citrate can also be included in the compositions of the present invention.

In addition, the use of several long-chain aldehydes, such as octanal, nonanal, decanal, and dodecanal. Where an embodiment describes the use of one such aldehyde, other embodiments are specifically contemplated in which the designated aldehyde is replaced with any of the other aldehydes, or a mixture of any of these aldehydes with each other or with the designated aldehyde.

Tocopherols are a class of chemicals consisting of various methylated phenols, some of which have vitamin E activity. These include a-tocopherol, β-tocopherol, γ-tocopherol, and δ-tocopherol. Also belonging to this family are the tocotrienols, including α-tocotrienol, β-tocotrienol, γ-tocotrienol, and δ-tocotrienol. In preferred embodiments, mixtures of these compositions, such as tocopherol gamma tenox or Tenox GT, are employed. Where an embodiment describes the use of one tocopherol, other embodiments are specifically contemplated in which the designated tocopherol is replaced with any of the other tocopherols, or a mixture of any of these tocopherols with each other or with the designated tocopherol.

Certain mixtures of liquefied hydrocarbons, such as propellants A-46, A-70, or 142A may be used as propellants in embodiments of spray mixtures. Where an embodiment describes the use of one propellant, other embodiments are specifically contemplated in which the designated propellant is replaced with any of the other propellant, or a mixture of any of these propellants with each other or with the designated propellant.

In certain exemplary compositions of the invention that include lilac flower oil, one or more of the following compounds can be substituted for the lilac flower oil: tetrahydrolinalool; ethyl linalool; heliotropine; hedion; hercolyn D; and triethyl citrate. In certain exemplary compositions of the invention that include black seed oil, one or more of the following compounds can be substituted for the black seed oil: alpha thujene: alpha-pinene; Beta-pinene; p-cymene; limonene; and tert-butyl-p-benzoquinone. In certain exemplary compositions of the invention that include thyme oil, one or more of the following compounds can be substituted for the thyme oil: thymol, α-thujone; α-pinene, camphene, β-pinene, p-cymene, α-terpinene, linalool, borneol, β-caryophyllene, and carvacrol. In certain exemplary embodiments of the invention that include methyl salicylate, oil of wintergreen can be substituted for the methyl salicylate. In certain exemplary embodiments of the invention that include oil of wintergreen, methyl salicylate can be substituted for the oil of wintergreen.

D-limonene is the main odour constituent of citrus (plant family Rutaceae), and is found in, among other citrus oils, lemon oil, lime oil, and orange oil. Where an embodiment describes the use of d-limonene, other embodiments are specifically contemplated in which the d-limonene is replaced by lemon oil, orange oil, lime oil, citrus oil, l-limonene, or dipentene (the racemic mixture of d-limonene and l-limonene).

Oils used to prepare the exemplary compositions of the present invention can be obtained commercially.

Exemplary embodiments of the invention also can include isopropyl myristate, which is an ester of isopropyl alcohol and myristic acid, is used as a thickening agent and emollient.

In those compositions including more than one oil, each oil can make up between about 0.1%, or less, to about 99%, or more, by weight, of the composition mixture. For example, one composition of the present invention comprises about 1% thymol and about 99% No geraniol. Optionally, the compositions can additionally comprise a fixed oil, which is a non-volatile non-scented plant oil. Fixed oils useful in the formulations of the present invention include, but are not limited to, castor oil, corn oil, cumin oil, mineral oil, olive oil, peanut oil, safflower oil, sesame oil, and soy bean oil.

In some embodiments, the pest control composition can include at least one of methyl salicylate, thyme oil, thymol, and/or geraniol. In other exemplary embodiments, pest control compositions include at least two of methyl salicylate, thyme oil, thymol, and/or geraniol. In other exemplary embodiments, pest control compositions according to the invention include methyl salicylate, thymol, and geraniol.

In some embodiments, the pest control composition can include at least two active ingredients selected from the group consisting of thymyl acetate, linalyl acetate, amyl butyrate, anise star oil, black seed oil, p-cymene, geraniol, isopropyl myristate, d-limonene, linalool, lilac flower oil, methyl salicylate, alpha-pinene, piperonal, piperonyl alcohol, tetrahydrolinalool, thyme oil white, thyme oil red, thymol, vanillin, and wintergreen oil.

In some embodiments, the pest control composition can include at least two active ingredients selected from the group consisting of alpha-pinene, thymol, para-cymene, linalool, thymyl acetate, and linalyl acetate. In some embodiments, the pest control composition can include at least three active ingredients selected from the group. In some embodiments, the composition includes alpha-pinene, thymol, para-cymene, and linalool. In some embodiments, the composition includes alpha-pinene, para-cymene, thymyl acetate, and linalyl acetate.

In some embodiments, where alpha-pinene is present in the composition in an amount within a range of 1-10%, the composition includes thymol or thymol acetate in an amount within a range of 20-75%, para-cymene in an amount within a range of 2%-50%, and linalool or linalyl acetate in an amount within a range of 3%-40%. These percentages can be in terms of weight percentage or in volume percentage.

In some embodiments, where alpha-pinene is present in the composition in an amount within a range of 4%-8%, the composition includes thymol or thymol acetate in an amount within a range of 30-65%, para-cymene in an amount within a range of 4%-40/o, and linalool or linalyl acetate in an amount within a range of 6%-30%. These percentages can be in terms of weight percentage or in volume percentage.

In some embodiments, the pest control composition can include at least two active ingredients selected from the group consisting of amyl butyrate, anise star oil, black seed oil, p-cymene, geraniol, isopropyl myristate, d-limonene, linalool, lilac flower oil, methyl salicylate, alpha-pinene, piperonal, piperonyl alcohol, tetrahydrolinalool, thyme oil white, thyme oil red, thymol, vanillin, and wintergreen oil.

In some embodiments, the at least two active ingredients are selected from the group consisting of geraniol, d-limonene, linalool, piperonal, tetrahydrolinalool, and vanillin. In some embodiments, where geraniol is present in the composition within a range of 3%-30%, the composition includes d-limonene in an amount within a range of 7%-30%, linalool in an amount within a range of 4%-20%, piperonal in an amount within a range of 2%-25%, tetrahydrolinalool in an amount within a range of 6%-22%, and vanillin in an amount within a range of 0.3%-1.5%. These percentages can be in terms of weight percentage or in volume percentage.

In some embodiments, the at least two active ingredients are selected from the group consisting of amyl butyrate, anise star oil, and thyme oil white. In some embodiments, where amyl butyrate is present in the composition within a range of 15%-30%, the composition includes anise star oil in an amount within a range of 40%-65%, and thyme oil white in an amount within a range of 15%-30%. These percentages can be in terms of weight percentage or in volume percentage.

In some embodiments, the at least two active ingredients are thyme oil white and wintergreen oil. In some embodiments, where thyme oil white is present in the composition within a range of 10-30%, the composition includes wintergreen oil in an amount within a range of 25%-55%. These percentages can be in terms of weight percentage or in volume percentage.

In some embodiments, the at least two active ingredients are selected from the group consisting of d-limonene, lilac flower oil, and thyme oil white. In some embodiments, where d-limonene is present in the composition within a range of 15%-35%, the composition includes lilac flower oil in an amount within a range of 30%-55%, and thyme oil white in an amount within a range of 20%-40%. These percentages can be in terms of weight percentage or in volume percentage.

In some embodiments, the at least two active ingredients are selected from the group consisting of alpha-pinene, thymol, para-cymene, and linalool. In some embodiments, where alpha-pinene is present in the composition in an amount within a range of 1-10%, the composition includes thymol in an amount within a range of 25-45%, para-cymene in an amount within a range of 20%-35%, and linalool in an amount within a range of 2%-15%. These percentages can be in terms of weight percentage or in volume percentage.

In some embodiments, the at least two active ingredients are selected from the group consisting of d-limonene, linalool, piperonal, piperonyl alcohol, tetrahydrolinalool, and vanillin. In some embodiments, where d-limonene is present in the composition within a range of 5%-15%, the composition includes linalool in an amount within a range of 10%-25%, piperonal in an amount within a range of 15%-30%, piperonyl alcohol in an amount within a range of 5%-15%, tetrahydrolinalool in an amount within a range of 10%-30%, and vanillin in an amount within a range of 0.5%-5%. These percentages can be in terms of weight percentage or in volume percentage.

While embodiments of the invention can include active ingredients, carriers, inert ingredients, and other formulation components, preferred embodiments begin with a primary blend. A primary blend is preferably a synergistic combination containing two or more active ingredients and, optionally, additional ingredients. The primary blends can then be combined with other ingredients to produce a formulation. Accordingly, where concentrations, concentration ranges, or amounts, are given herein, such quantities typically are in reference to a primary blend or blends. Thus, when a primary blend is further modified by addition of other ingredients to produce a formulation, the concentrations of the active ingredients are reduced proportional to the presence of other ingredients in the formulation.

In preferred blends, methyl salicylate can be included at a concentration of between 10% or less to 60% or more; at a concentration of between 15%-50%; at a concentration of between 20%-45%; or at a concentration of about 39% by weight.

Thymol can be included at a concentration of between 5% or less to 40% or more; at a concentration of between 15%-25%; or at a concentration of about 20% by weight.

Thyme Oil can be included at a concentration of between 5% or less to 40% or more, at a concentration of between 15%-25%, or at a concentration of about 20% by weight. Geraniol can be included at a concentration of between 5% or less to 40% or more, at a concentration of 15%-25%, or at a concentration of about 20% by weight.

In exemplary embodiments, the pest control formulation also includes isopropyl myristate at a concentration of between 10-30%, more preferably 15-25%, and most preferably about 20%. Vanillin is included, preferably at a concentration between 0.5 and 4%, most preferably about 1%.

In exemplary embodiments of the invention, thymol is present in crystal form. By using the crystal form, the more volatile components of the pest control composition are stabilized and remain in the area requiring pest control for a longer period. This is explained in U.S. Provisional Application No. 60/799,434, filed May 10, 2006 which is incorporated in its entirety herein by reference. Of course, other components can be included to stabilize the pest control composition. The stabilizer can be a crystal powder, dust, granule or other form which provides an absorption surface area for the pest control composition. Other plant essential oils that are crystalline at room temperature and can be used as stabilizers in formulations of the invention include but are not limited to cinnamic alcohol crystals, salicylic acid crystals, cedrol crystals, piperonal crystals, piperonyl alcohol crystals, (s)-cis-verbenol crystals and DL—menthol crystals which are all crystalline at room temperature. Another stabilizer that can be used is a crystal of Winsense WS-3, cyclohexanecarboxamide, N-methyl-2-(1-methylethyl) and Winsense WE-23, (N-2,3-trimethy-2-isopropylbutamide) and the like. Another useful stabilizer is talc powder.

In order to produce the stabilized formulation, the stabilizer and the insect-control composition are mixed to allow the stabilizer to become coated with the composition as described in U.S. Provisional Application No. 60/799,434, mentioned above.

The compositions of the present invention can comprise, in admixture with a suitable carrier and optionally with a suitable surface active agent, plant essential oil compounds and/or derivatives thereof, natural and/or synthetic, including racemic mixtures, enantiomers, diastereomers, hydrates, salts, solvates and metabolites, etc.

A suitable carrier can include any carrier in the art known for plant essential oils, provided the carrier does not adversely effect the compositions of the present invention. The term "carrier" as used herein means an inert or fluid material, which can be inorganic or organic and of synthetic or natural origin, with which the active compound is mixed or formulated to facilitate its application to the container or carton or other object to be treated, or to facilitate its storage, transport and/or handling. In general, any of the materials customarily employed in formulating repellents, pesticides, herbicides, or fungicides, are suitable. The compositions of the present invention can be employed alone or in the form of mixtures with such solid and/or liquid dispersible carrier vehicles and/or other known compatible active agents such as other repellants, pesticides, or acaricides, nematicides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use. The compositions of the present invention can be formulated or mixed with, if desired, conventional inert pesticide diluents or extenders of the type usable in conventional pest control agents, e.g., conventional dispersible carrier vehicles such as gases, solutions, emulsions, suspensions, emulsifiable concentrates, spray powders, pastes, soluble powders, dusting agents, granules, foams, pastes, tablets, aerosols, natural and synthetic materials impregnated with active compounds, encapsulating agents, microcapsules, coating compositions for use on seeds, and formulations used with burning equipment, such as fumigating cartridges, fumigating cans and fumigating coils, as well as ULV cold mist and warm mist formulations, etc.

Exemplary encapsulating agents can include, but are not limited to, gum arabic, dextrins, low viscosity modified starches, arabinogalactan, gum acacia, casein, gelatin, carboxymethyl cellulose, tragacanth, karaya, sodium alginate, tannin, celluloses, zein shellac, or mixtures thereof.

The compositions of the present invention can further comprise surface-active agents. Examples of surface-active agents that can be employed with the present invention, include emulsifying agents, such as non-ionic and/or anionic emulsifying agents (e.g., polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents such as lignin, sulfite waste liquors, methyl cellulose, etc.

In some embodiments, water-based formulations are preferred. Although oil-based formulations of insect-control agents are generally more effective, water-based formulations have the advantage that they do not leave behind an oily residue on treated surfaces. Preparation of water-based formulations for pest control are disclosed in U.S. Provisional Application No. 60/747,592, filed May 18, 2006, which is incorporated in its entirety herein by reference.

In some embodiments, water-based formulations are provided wherein water and a surfactant comprise between about 1% to about 99%, by weight, of the composition mixture. For example, one composition of the present invention comprises about 1% water and surfactant and about 99% of a composition, including: about 39% Methyl salicylate; about 20% Thymol (crystal); about 20% Geraniol 60; and about 1% Vanillin. For another example, one composition of the present invention comprises about 50% water and surfactant and about 50% of a composition, including: about 39% Methyl salicylate; about 20% Thymol (crystal); about 20% Geraniol 60; and about 1% Vanillin.

The surfactant of the water-based formulation is provided to facilitate mixture of the insect-control composition with the water. The surfactant may include an end having a carboxyl group, which will face the water molecules, and a hydrocarbon end, which will face an oil component of the insect-control composition. As such, the surfactant allows the water and the oil component of the composition to be mixed to form an emulsion. Various surfactants may be used in the formulation of the present invention, for example, sodium lauryl sulfate (SLS, anionic), chlorhexidine (CLH, cationic), and Poloxamer 407 (POL407, nonionic), Sodium dodecylsulfate (SDS), Sodium cholate, Sodium deoxycholate, N-Lauroylsarcosine, Lauryldimethylamine-oxide (LDAO), Cetyltrimethylammoniumbromide (CTAB), Bis(2-ethylhexyl)sulfosuccinate, or mixtures thereof.

The solvent of the water-based formulation serves to reduce the water-oil surface tension of the emulsion. By reducing this surface tension, the oil spots are more readily dispersed in the water, and a thin film of the oil-water mixture is allowed to form on the treated surfaces, which surfaces may include areas within a household, outdoor areas, plants and the insects themselves. The solvent may also serve as a carrier and a synergist. The solvent may assist in fast penetration through the cell membrane of an insect being controlled to ensure the arrival of sufficient active ingredients to the site of action. Various solvents may be used, for example, isopar M, isopar C, or mixtures thereof.

To produce the water-based formulation, the insect-control composition containing one or more plant essential oils is mixed with water to create a slurry. The surfactant is then added to create certain embodiments of the water-based formulation. To create other embodiments of the water-based formulation, the solvent is then added. The final concentration of the insect-control composition in the formulation may be, for example, about 10-25%. The final concentration of the surfactant in the formulation may be, for example, about 1-10%. The final concentration of the solvent in the formulation may be, for example, 0 to about 10%. Some embodiments of the present invention are characterized by rapid killing, e.g., kill-on-contact, and some embodiments are characterized by residual effects, i.e., formulation remains on treated surface affecting pest control for an extended period of time. In the case of the embodiment characterized by residual effects, it should be noted that the solvent-component of the formulation is not necessary. In such embodiments of the invention, the formulation includes: water, an insect-control composition, a surfactant, and a stabilizer, such as the one described in the patent application entitled, "Formulations of Insect-Control Compositions having Residual Activity and Methods for Production and Use Thereof," filed on May 10, 2005. Such embodiments may optionally include the solvent described herein.

Once the water-based formulation has been prepared, it may be applied to a desired area to affect pest control in that area. Once applied, it will form a thin film on the treated surfaces, adhering thereto and providing effective pest control. The formulation may be applied to the area in a variety of manners known in the art, for example, the formulation may be prepared as an aerosol or trigger spray.

In some embodiments, a mixture of an pest control composition that includes one or more plant essential oils with a carrier is provided. For example, embodiments of the present invention can include a carrier having a surface area, with the insect-control composition coated on the surface area of the carrier. The carrier may be, for example, crystals, powder, dust, granules or the like, which provides an absorption surface area for the insect-control compositions. One example of a carrier that can be used in accordance with the present invention is diatomaceous earth (DE). DE is a naturally occurring sedimentary rock that is easily crumbled into a fine powder. This powder has an abrasive feel, similar to pumice powder, and is very light, due to its high porosity. Diatomaceous earth consists of fossilized remains of diatoms, a type of hard-shelled algae.

In some embodiments, the carrier and the insect-control composition are mixed to allow the carrier to become coated with the composition. In some embodiments of the invention, after the carrier has been coated with the insect-control composition to form the formulation, the formulation can be applied to a desired area to affect pest control in that area. Because the carrier reduces the volatility of the insect-control composition, the composition will remain active in the desired area for an amount of time that is greater than the time the composition, alone, i.e., unformulated composition, would remain in the desired area. As such, the formulation continues to provide insect-control after the time by which the composition, alone, would have volatilized.

In some embodiments, the pest control compositions can be combined with one or more synthetic pesticides such as a pyrethroid, a chloronicotinyl insecticide, and a neonicotinoid. For example, the pest control blends can be combined with deltamethrin, clothianidin, or imidacloprid. The synthetic pesticides can be obtained commerically.

Embodiments of the present invention can be used to control insects by treating an area directly. For example, the area can be treated by spreading the formulation, for example, manually, automatically, with a fertilizer spreader, or the like.

The compositions of the present invention can be used to control insects by either treating a host directly, or treating an area in which the host will be located. For example, the host can be treated directly by using a cream or spray formulation, which can be applied externally or topically, e.g., to the skin of a human. A composition can be applied to the host, for example, in the case of a human, using formulations of a variety of personal products or cosmetics for use on the skin or hair. For example, any of the following can be used: fragrances, colorants, pigments, dyes, colognes, skin creams, skin lotions, deodorants, talcs, bath oils, soaps, shampoos, hair conditioners and styling agents.

The compositions of a select number of specifically contemplated embodiments of the present invention, which includes exemplary synergistic blends, are shown in Table 1. This table provides exemplary combinations of ingredients for useful blends in accordance with the invention. In many cases a particular ingredient is listed very specifically such as, for example, with reference to a CAS number and/or particular modifiers of the basic name of the ingredient. Such specific listings are non-limiting examples of types of ingredients, and similar ingredients (such as, for example, with different CAS numbers and/or variant forms of the type of ingredient) can be substituted within the scope of certain embodiments of the invention.

Table 1 also provides an exemplary range of amounts of each ingredient expressed as a weight/weight percentage of the listed blend. The exemplary range for each ingredient in each blend is provided as a number in the fourth column indicating a value at the low end of such exemplary range, and in the fifth column indicating a value at the high end of such exemplary range. The provided ranges are exemplary, other useful ranges exist and are expressly within the scope of certain embodiments on the invention. Namely, other high and low amounts defining other useful ranges and/or amounts of the listed ingredients, can include 1%, 2%, 5%, 10%, 15%, 20%, 25%, 40%, 50%, 60%, 75%, 85%, 95%, 110%, 125%, 150%, 175%, 200%, 250%, 300%, 400%, 500%, 750%, 900%, or 1000% of the amount listed as the low amount and/or the high amount, with the caveat that the relative percentage of any given ingredient cannot exceed 99.99% of the total blend of ingredients.

TABLE 1

BLENDS

| | Compounds | CAS Registry Number | low % | high % |
|---|---|---|---|---|
| Blend 1 | LFO | | 4 | 30 |
| | D-Limonene | 5989-27-5 | 8 | 99 |
| | Thyme Oil White | 8007-46-3 | 0.1 | 20 |
| | Blend 65 | | 8 | 99 |
| Blend 2 | D-Limonene | 5989-27-5 | 9 | 99 |
| | Thyme Oil White | 8007-46-3 | 0.1 | 20 |
| | Linalool Coeur | 78-70-6 | 0.1 | 4 |
| | Tetrahydrolinalool | 78-69-3 | 0.1 | 5 |
| | Vanillin | 121-33-5 | 0.06 | 0.3 |
| | Isopropyl myristate | 110-27-0 | 0.1 | 5 |
| | Piperonal (aldehyde) [Heliotropine] | 120-57-0 | 0.1 | 5 |
| | Blend 66 | | 8 | 99 |
| | Geraniol Fine FCC | 106-24-1 | 0.1 | 4 |
| | Triethyl Citrate | 77-93-0 | 0.1 | 5 |
| Blend 3 | D-Limonene | 5989-27-5 | 45 | 99 |
| | Thyme Oil White | 8007-46-3 | 0.1 | 10 |
| | Blend 66 | | 5 | 30 |
| | Blend 63 | | 0.1 | 10 |
| Blend 4 | LFO | | 30 | 99 |
| | BSO | 977017-84-7 | 15 | 99 |
| Blend 5 | BSO | 977017-84-7 | 15 | 99 |
| | Linalool Coeur | 78-70-6 | 6 | 40 |

TABLE 1-continued

BLENDS

| | Compounds | CAS Registry Number | low % | high % |
|---|---|---|---|---|
| | Tetrahydrolinalool | 78-69-3 | 8 | 45 |
| | Vanillin | 121-33-5 | 0.1 | 5 |
| | Isopropyl myristate | 110-27-0 | 10 | 55 |
| | Piperonal (aldehyde) [Heliotropine] | 120-57-0 | 0.1 | 20 |
| | Geraniol Fine FCC | 106-24-1 | 0.1 | 25 |
| Blend 6 | D-Limonene | 5989-27-5 | 0.1 | 25 |
| | BSO | 977017-84-7 | 15 | 85 |
| | Linalool Coeur | 78-70-6 | 0.1 | 25 |
| | Tetrahydrolinalool | 7869-3 | 0.1 | 25 |
| | Vanillin | 121-33-5 | 0.1 | 3 |
| | Isopropyl myristate | 110-27-0 | 0.1 | 30 |
| | Piperonal (aldehyde) [Heliotropine] | 120-57-0 | 0.1 | 10 |
| | Geraniol Fine FCC | 106-24-1 | 0.1 | 15 |
| | Methyl Salicylate 98% Nat | 119-36-8 | 8 | 70 |
| Blend 7 | Thyme Oil White | 8007-46-3 | 15 | 90 |
| | Wintergreen Oil | 68917-75-9 | 15 | 99 |
| | Vanillin | 121-33-5 | 0.1 | 4 |
| | Isopropyl myristate | 110-27-0 | 20 | 99 |
| Blend 8 | D-Limonene | 5989-27-5 | 20 | 99 |
| | Thyme Oil White | 8007-46-3 | 0.1 | 25 |
| | Wintergreen Oil | 68917-75-9 | 25 | 99 |
| Blend 9 | LFO | | 6 | 40 |
| | D-Limonene | 5989-27-5 | 25 | 99 |
| | Thyme Oil White | 8007-46-3 | 5 | 30 |
| | Linalool Coeur | 78-70-6 | 0.1 | 3 |
| | Citral | 5392-40-5 | 0.1 | 20 |
| | gamma-terpinene | 99-85-4 | 0.1 | 20 |
| | Alpha-Pinene, 98% | 80-56-8 | 0.1 | 5 |
| | alpha-Terpineol | 98-55-5 | 0.1 | 15 |
| | Terpinolene | 586-62-9 | 0.1 | 15 |
| | Para-Cymene | 99-87-6 | 0.1 | 5 |
| | Linalyl Acetate | 115-95-7 | 0.1 | 6 |
| | Beta Pinene | 127-91-3 | 0.1 | 6 |
| | Camphor Dextro | 464-49-3 | 0.05 | 0.3 |
| | Terpinene 4 OL | 562-74-3 | 0.05 | 0.3 |
| | Alpha Terpinene | 99-86-5 | 0.1 | 6 |
| | Borneol L | 507-70-0 | 0.1 | 3 |
| | Camphene | 79-92-5 | 0.1 | 2 |
| | Decanal | 112-31-2 | 0.06 | 0.3 |
| | Dodecanal | 112-54-9 | 0.06 | 0.3 |
| | Fenchol Alpha | 512-13-0 | 0.005 | 0.1 |
| | Geranyl Acetate | 105-87-3 | 0.06 | 0.3 |
| | Isoborneol | 124-76-5 | 0.08 | 1 |
| | 2-Methyl 1,3-cyclohexadiene | 30640-46-1, 1888-90-0 | 0.08 | 1 |
| | Myrcene | 123-35-3 | 0.1 | 3 |
| | Nonanal | 124-19-6 | 0.005 | 0.08 |
| | Octanal | 124-13-0 | 0.005 | 0.2 |
| | Tocopherol Gamma (TENOX ®) | 54-28-4 | 0.005 | 0.08 |
| Blend 10 | D-Limonene | 5989-27-5 | 0.1 | 25 |
| | Thyme Oil White | 8007-46-3 | 0.1 | 25 |
| | Blend 65 | | 40 | 99 |
| | Linalool Coeur | 78-70-6 | 0.1 | 6 |
| | Tetrahydrolinalool | 78-69-3 | 0.1 | 8 |
| | Vanillin | 121-33-5 | 0.08 | 0.6 |
| | Isopropyl myristate | 110-27-0 | 0.1 | 8 |
| | Piperonal (aldehyde) [Heliotropine] | 120-57-0 | 0.1 | 8 |
| | Geraniol Fine FCC | 106-24-1 | 0.1 | 4 |
| | Triethyl Citrate | 77-93-0 | 0.1 | 8 |
| Blend 11 | Thyme Oil White | 8007-46-3 | 3 | 65 |
| | Wintergreen Oil | 68917-75-9 | 15 | 99 |
| | Isopropyl myristate | 110-27-0 | 20 | 99 |
| Blend 12 | D-Limonene | 5989-27-5 | 5 | 30 |
| | Linalool Coeur | 78-70-6 | 8 | 40 |
| | Tetrahydrolinalool | 78-69-3 | 15 | 99 |
| | Vanillin | 121-33-5 | 0.1 | 8 |
| | Isopropyl myristate | 110-27-0 | 15 | 85 |

TABLE 1-continued

BLENDS

| | Compounds | CAS Registry Number | low % | high % |
|---|---|---|---|---|
| | Piperonal (aldehyde)[Heliotropine] | 120-57-0 | 5 | 30 |
| | Geraniol Fine FCC | 106-24-1 | 5 | 30 |
| Blend 13 | D-Limonene | 5989-27-5 | 5 | 30 |
| | Geraniol Fine FCC | 106-24-1 | 5 | 30 |
| | Blend 62 | | 50 | 99 |
| Blend 14 | D-Limonene | 5989-27-5 | 5 | 30 |
| | Blend 72 | | 55 | 99 |
| Blend 15 | D-Limonene | 5989-27-5 | 5 | 30 |
| | Linalool Coeur | 78-70-6 | 10 | 55 |
| | Tetrahydrolinalool | 78-69-3 | 10 | 65 |
| | Vanillin | 121-33-5 | 0.1 | 4 |
| | Isopropyl myristate | 110-27-0 | 10 | 60 |
| | Piperonal (aldehyde)[Heliotropine] | 120-57-0 | 10 | 65 |
| | Piperonyl Alcohol | 495-76-1 | 0.1 | 25 |
| Blend 16 | D-Limonene | 5989-27-5 | 5 | 30 |
| | BSO | 977017-84-7 | 15 | 80 |
| | Linalool Coeur | 78-70-6 | 5 | 30 |
| | Tetrahydrolinalool | 78-69-3 | 6 | 35 |
| | Vanillin | 121-33-5 | 0.1 | 4 |
| | Mineral Oil White (USP) | 8042-47-5 | 8 | 45 |
| | Isopropyl myristate | 110-27-0 | 8 | 45 |
| | Piperonal (aldehyde)[Heliotropine] | 120-57-0 | 0.1 | 15 |
| | Geraniol Fine FCC | 106-24-1 | 0.1 | 20 |
| Blend 17 | D-Limonene | 5989-27-5 | 10 | 99 |
| | Linalool Coeur | 78-70-6 | 0.1 | 10 |
| | Tetrahydrolinalool | 7869-3 | 0.1 | 10 |
| | Vanillin | 121-33-5 | 0.08 | 0.6 |
| | Isopropyl myristate | 110-27-0 | 0.1 | 10 |
| | Piperonal (aldehyde)[Heliotropine] | 120-57-0 | 0.1 | 10 |
| | Piperonyl Alcohol | 495-76-1 | 0.1 | 5 |
| | Blend 66 | | 10 | 99 |
| Blend 18 | Linalool Coeur | 78-70-6 | 0.1 | 15 |
| | Tetrahydrolinalool | 78-69-3 | 0.1 | 20 |
| | Vanillin | 121-33-5 | 0.1 | 2 |
| | Isopropyl myristate | 110-27-0 | 0.1 | 20 |
| | Piperonal (aldehyde)[Heliotropine] | 120-57-0 | 0.1 | 20 |
| | Piperonyl Alcohol | 495-76-1 | 0.1 | 10 |
| | Blend 66 | | 40 | 99 |
| Blend 19 | LFO | | 20 | 99 |
| | D-Limonene | 5989-275 | 15 | 85 |
| | Thyme Oil White | 8007-46-3 | 15 | 90 |
| Blend 20 | D-Limonene | 5989-27-5 | 15 | 85 |
| | Thyme Oil White | 8007-46-3 | 15 | 95 |
| | Blend 63 | | 20 | 99 |
| Blend 21 | D-Limonene | 5989-27-5 | 15 | 85 |
| | Thyme Oil White | 8007-46-3 | 15 | 90 |
| | Linalool Coeur | 78-70-6 | 0.1 | 15 |
| | Tetrahydrolinalool | 78-69-3 | 0.1 | 25 |
| | Vanillin | 121-33-5 | 0.1 | 2 |
| | Isopropyl myristate | 110-27-0 | 0.1 | 25 |
| | Piperonal (aldehyde)[Heliotropine] | 120-57-0 | 0.1 | 25 |
| | Geraniol Fine FCC | 106-24-1 | 0.1 | 10 |
| | Triethyl Citrate | 77-93-0 | 0.1 | 25 |
| Blend 22 | Phenyl Ethyl Propionate | | 20 | 99 |
| | Methyl Salicylate | | 20 | 99 |
| | Blend 43 | | 15 | 85 |
| Blend 23 | D-Limonene | 5989-27-5 | 0.1 | 10 |
| | Thyme Oil White | 8007-46-3 | 0.1 | 15 |
| | Benzyl Alcohol | 100-51-6 | 8 | 50 |
| | Isopar M | 64742-47-8 | 10 | 65 |
| | Water | 7732-18-5 | 25 | 99 |
| | Blend 63 | | 0.1 | 15 |
| | Stock 10% SLS Solution | | 0.1 | 10 |
| Blend 24 | D-Limonene | 5989-27-5 | 0.1 | 10 |
| | Thyme Oil White | 8007-46-3 | 0.1 | 15 |
| | Linalool Coeur | 78-70-6 | 0.1 | 3 |
| | Tetrahydrolinalool | 78-69-3 | 0.1 | 4 |
| | Vanillin | 121-33-5 | 0.05 | 0.3 |
| | Isopropyl myristate | 110-27-0 | 0.1 | 4 |
| | Piperonal (aldehyde)[Heliotropine] | 120-57-0 | 0.1 | 4 |
| | Geraniol Fine FCC | 106-24-1 | 0.1 | 2 |
| | Triethyl Citrate | 77-93-0 | 0.1 | 4 |
| | Benzyl Alcohol | 100-51-6 | 8 | 50 |
| | Isopar M | 64742-47-8 | 10 | 65 |
| | Water | 7732-18-5 | 25 | 99 |
| | Stock 10% SLS Solution | | 0.1 | 10 |
| Blend 25 | D-Limonene | 5989-27-5 | 6 | 40 |
| | Thyme Oil White | 8007-46-3 | 8 | 45 |
| | Benzyl Alcohol | 100-51-6 | 30 | 99 |
| | Blend 63 | | 10 | 55 |
| Blend 26 | LFO | | 0.1 | 25 |
| | D-Limonene | 5989-27-5 | 8 | 99 |
| | Thyme Oil White | 8007-46-3 | 0.1 | 20 |
| | Blend 66 | | 8 | 99 |
| Blend 27 | Linalool Coeur | 78-70-6 | 0.1 | 20 |
| | Soy Bean Oil | 8016-70-4 | 10 | 70 |
| | Thymol (crystal) | 89-83-8 | 20 | 99 |
| | Alpha-Pinene, 98% | 80-56-8 | 0.1 | 10 |
| | Para-Cymene | 99-87-6 | 15 | 85 |
| Blend 28 | Linalool Coeur | 78-70-6 | 0.1 | 25 |
| | Thymol (crystal) | 89-83-8 | 25 | 99 |
| | Alpha-Pinene, 98% | 80-56-8 | 0.1 | 15 |
| | Para-Cymene | 99-87-6 | 20 | 99 |
| Blend 29 | D-Limonene | 5989-27-5 | 0.1 | 25 |
| | Thyme Oil White | 8007-46-3 | 0.1 | 30 |
| | Blend 65 | | 35 | 99 |
| | Linalool Coeur | 78-70-6 | 0.1 | 8 |
| | Tetrahydrolinalool | 78-69-3 | 0.1 | 10 |
| | Vanillin | 121-33-5 | 0.08 | 1 |
| | Isopropyl myristate | 110-27-0 | 0.1 | 10 |
| | Piperonal (aldehyde)[Heliotropine] | 120-57-0 | 0.1 | 5 |
| | Geraniol Fine FCC | 106-24-1 | 0.1 | 5 |
| Blend 30 | D-Limonene | 5989-27-5 | 15 | 85 |
| | Thyme Oil White | 8007-46-3 | 0.1 | 15 |
| | Methyl Salicylate | | 35 | 99 |
| Blend 31 | Thyme Oil White | 8007-46-3 | 0.1 | 5 |
| | Wintergreen Oil | 68917-75-9 | 0.1 | 8 |
| | Isopropyl myristate | 110-27-0 | 0.1 | 6 |
| | Span 80 | 1338-43-8 | 0.1 | 2 |
| | Isopar M | 64742-47-8 | 8 | 45 |
| | Water | 7732-18-5 | 40 | 99 |
| | Bifenthrin | 83657-04-3 | 0.005 | 0.2 |
| Blend 32 | Castor Oil hydrogenated-PEO40 | | 30 | 99 |
| | Lemon Grass Oil-India | | 10 | 70 |
| | Blend 1 | | 10 | 70 |
| Blend 33 | LFO | | 8 | 50 |
| | D-Limonene | 5989-27-5 | 35 | 99 |
| | Thyme Oil White | 8007-46-3 | 6 | 35 |
| | BSO | 977017-84-7 | 0.1 | 15 |
| Blend 34 | D-Limonene | 5989-27-5 | 0.1 | 25 |
| | Thyme Oil White | 8007-46-3 | 0.1 | 30 |
| | Blend 65 | | 30 | 99 |
| | Linalool Coeur | 78-70-6 | 0.1 | 5 |
| | Tetrahydrolinalool | 78-69-3 | 0.1 | 8 |
| | Vanillin | 121-33-5 | 0.06 | 0.5 |
| | Isopropyl myristate | 110-27-0 | 0.1 | 8 |
| | Piperonal (aldehyde)[Heliotropine] | 120-57-0 | 0.1 | 8 |
| | Geraniol Fine FCC | 106-24-1 | 0.1 | 4 |
| | Triethyl Citrate | 77-93-0 | 0.1 | 8 |
| | Isopar M | 64742-47-8 | 8 | 40 |
| Blend 35 | Isopropyl myristate | 110-27-0 | 20 | 99 |
| | Wintergreen Oil | | 25 | 99 |
| | Blend 68 | | 10 | 60 |
| Blend 36 | Wintergreen Oil | 68917-75-9 | 25 | 99 |
| | Isopropyl myristate | 110-27-0 | 20 | 99 |
| | Thyme Oil Red | 8007-46-3 | 10 | 60 |
| Blend 37 | Wintergreen Oil | 68917-75-9 | 25 | 99 |
| | Vanillin | 121-33-5 | 0.06 | 0.3 |

TABLE 1-continued

BLENDS

| | Compounds | CAS Registry Number | low % | high % |
|---|---|---|---|---|
| | Isopropyl myristate | 110-27-0 | 20 | 99 |
| | Thyme Oil Red | 8007-46-3 | 10 | 60 |
| Blend 38 | Thyme Oil White | 8007-46-3 | 15 | 95 |
| | Isopropyl myristate | 110-27-0 | 25 | 99 |
| | Geraniol Fine FCC | 106-24-1 | 10 | 70 |
| Blend 39 | Isopropyl myristate | 110-27-0 | 25 | 99 |
| | Geraniol Fine FCC | 106-24-1 | 10 | 70 |
| | Blend 68 | | 20 | 99 |
| Blend 40 | Orange Terpenes | 68647-72-3 | 0.1 | 25 |
| | Blend 68 | | 0.1 | 30 |
| | Blend 69 | | 35 | 99 |
| | Blend 71 | | 6 | 40 |
| Blend 41 | Linalool Coeur | 78-70-6 | 10 | 70 |
| | Amyl Butyrate | 540-18-1 | 10 | 70 |
| | Anise Star Oil | | 30 | 99 |
| Blend 42 | Thyme Oil White | 8007-46-3 | 15 | 75 |
| | Amyl Butyrate | 540-18-1 | 10 | 70 |
| | Anise Star Oil | | 30 | 99 |
| Blend 43 | Tetrahydrolinalool | 78-69-3 | 10 | 70 |
| | Vanillin | 121-33-5 | 0.1 | 4 |
| | Hercolyn D | 8050-15-5 | 0.1 | 15 |
| | Isopropyl myristate | 110-27-0 | 8 | 45 |
| | Piperonal (aldehyde)[Heliotropine] | 120-57-0 | 0.1 | 25 |
| | Ethyl Linalool | 10339-55-6 | 10 | 70 |
| | Hedione | 24851-98-7 | 0.1 | 20 |
| | Triethyl Citrate | 77-93-0 | 5 | 30 |
| | Dipropylene glycol (DPG) | 246-770-3 | 0.1 | 25 |
| Blend 44 | Blend 63 | | 25 | 99 |
| | Thyme Oil White | | 30 | 99 |
| Blend 45 | Linalool coeur | 78-70-6 | 0.1 | 20 |
| | Tetrahydrolinalool | 78-69-3 | 0.1 | 25 |
| | Vanillin | 121-33-5 | 0.1 | 2 |
| | Isopropyl myristate | 110-27-0 | 0.1 | 30 |
| | Piperonal (aldehyde)[Heliotropine] | 120-57-0 | 0.1 | 30 |
| | Geraniol Fine FCC | 106-24-1 | 0.1 | 15 |
| | Triethyl citrate | 77-93-0 | 0.1 | 30 |
| | Thyme Oil White | | 30 | 99 |
| Blend 46 | Phenyl Ethyl Propionate | | 10 | 55 |
| | Benzyl Alcohol | 100-51-6 | 30 | 99 |
| | Methyl Salicylate | | 10 | 55 |
| | Blend 43 | | 8 | 40 |
| Blend 47 | Thyme Oil White | 8007-46-3 | 15 | 75 |
| | Amyl Butyrate | 540-18-1 | 10 | 70 |
| | Anise Star Oil | | 30 | 99 |
| | Genistein | | 0.005 | 0.1 |
| Blend 48 | Linalool coeur | 78-70-6 | 10 | 70 |
| | Amyl Butyrate | 540-18-1 | 10 | 70 |
| | Anise Star Oil | | 30 | 99 |
| | Thyme Oil White | | 0.005 | 0.1 |
| Blend 49 | LFO | | 10 | 70 |
| | BSO | 977017-84-7 | 10 | 70 |
| | Benzyl Alcohol | 100-51-6 | 30 | 99 |
| Blend 50 | Isopropyl myristate | 110-27-0 | 10 | 70 |
| | Wintergreen oil | | 15 | 90 |
| | Thyme oil white | | 8 | 40 |
| | Myristicin | | 15 | 99 |
| Blend 51 | Isopropyl myristate | 110-27-0 | 15 | 80 |
| | Wintergreen oil | | 15 | 95 |
| | Isopropyl alcohol | 67-63-0 | 0.1 | 10 |
| | Thyme oil white | | 8 | 40 |
| | Myristicin | | 15 | 75 |
| Blend 52 | Isopropyl myristate | 110-27-0 | 20 | 99 |
| | Wintergreen oil | | 25 | 99 |
| | Thyme oil white | | 10 | 60 |
| | Genistein | | 0.001 | 0.1 |
| Blend 53 | Isopropyl myristate | 110-27-0 | 20 | 99 |
| | Wintergreen oil | | 20 | 99 |
| | Isopropyl alcohol | 67-63-0 | 5 | 30 |
| | Thyme oil white | | 8 | 50 |
| | Genistein | | 0.001 | 0.1 |
| Blend 54 | Isopropyl myristate | 110-27-0 | 10 | 70 |
| | Wintergreen oil | | 15 | 90 |
| | Thyme oil white | | 8 | 40 |
| | Genistein | | 0.001 | 0.1 |
| | Myristicin | | 15 | 99 |
| Blend 55 | Mineral oil white | 8042-47-5 | 20 | 99 |
| | Wintergreen oil | | 25 | 99 |
| | Thyme oil white | | 10 | 60 |
| Blend 56 | Mineral oil white | 8042-47-5 | 10 | 50 |
| | Wintergreen oil | | 10 | 65 |
| | Thyme oil white | | 5 | 30 |
| | Benzaldehyde | | 30 | 99 |
| Blend 57 | Mineral oil white | 8042-47-5 | 10 | 55 |
| | Wintergreen oil | | 10 | 65 |
| | Thyme oil white | | 5 | 30 |
| | Genistein | | 15 | 75 |
| | Benzaldehyde | | 15 | 80 |
| Blend 58 | Linalool Coeur | 78-70-6 | 4 | 65 |
| | Thymol (crystal) | 89-83-8 | 20 | 99 |
| | Alpha-Pinene, 98% | 80-56-8 | 1 | 10 |
| | Para-Cymene | 99-87-6 | 1 | 55 |
| | Trans-Anethole | 4180-23-8 | 10 | 55 |
| Blend 59 | Linalool Coeur | 78-70-6 | 0.1 | 30 |
| | Thymol (crystal) | 89-83-8 | 25 | 99 |
| | Alpha-Pinene, 98% | 80-56-8 | 0.1 | 30 |
| | Para-Cymene | 99-87-6 | 15 | 99 |
| Blend 60 | Soy Bean Oil | 8016-70-4 | 15 | 75 |
| | Alpha-Pinene, 98% | 80-56-8 | 0.1 | 10 |
| | Para-Cymene | 99-87-6 | 15 | 85 |
| | Linalyl Acetate | 115-95-7 | 0.1 | 20 |
| | Thymol acetate | 528-79-0 | 20 | 99 |
| Blend 61 | Alpha-Pinene, 98% | 80-56-8 | 0.1 | 30 |
| | Para-Cymene | 99-87-6 | 10 | 55 |
| | Linalyl Acetate | 115-95-7 | 10 | 70 |
| | Thymol acetate | 528-79-0 | 30 | 99 |
| Blend 62 | Linalool Coeur | 78-70-6 | 10 | 60 |
| | Tetrahydrolinalool | 78-69-3 | 10 | 70 |
| | Vanillin | 121-33-5 | 0.1 | 8 |
| | Isopropyl myristate | 110-27-0 | 15 | 90 |
| | Piperonal (aldehyde)[Heliotropine] | 120-57-0 | 5 | 30 |
| | Geraniol Fine FCC | 106-24-1 | 8 | 40 |
| Blend 63 | Linalool Coeur | 78-70-6 | 8 | 40 |
| | Tetrahydrolinalool | 78-69-3 | 10 | 55 |
| | Vanillin | 121-33-5 | 0.1 | 4 |
| | Isopropyl myristate | 110-27-0 | 10 | 55 |
| | Piperonal (aldehyde)[Heliotropine] | 120-57-0 | 10 | 55 |
| | Geraniol Fine FCC | 106-24-1 | 5 | 30 |
| | Triethyl Citrate | 77-93-0 | 10 | 55 |
| Blend 64 | Linalool Coeur | 78-70-6 | 10 | 60 |
| | Tetrahydrolinalool | 78-69-3 | 10 | 70 |
| | Vanillin | 121-33-5 | 0.1 | 4 |
| | Isopropyl myristate | 110-27-0 | 10 | 70 |
| | Piperonal (aldehyde)[Heliotropine] | 120-57-0 | 10 | 70 |
| | Piperonyl Alcohol | 495-76-1 | 0.1 | 30 |
| Blend 65 | D-Limonene | 5989-27-5 | 25 | 99 |
| | Linalool Coeur | 78-70-6 | 0.1 | 4 |
| | Citral | 5392-40-5 | 5 | 30 |
| | gamma-terpinene | 99-85-4 | 5 | 30 |
| | Alpha-Pinene, 98% | 80-56-8 | 0.1 | 6 |
| | alpha-Terpineol | 98-55-5 | 0.1 | 20 |
| | Terpinolene | 586-62-9 | 0.1 | 20 |
| | Para-Cymene | 99-87-6 | 0.1 | 5 |
| | Linalyl Acetate | 115-95-7 | 0.1 | 8 |
| | Beta Pinene | 127-91-3 | 0.1 | 10 |
| | Camphor Dextro | 464-49-3 | 0.06 | 0.3 |
| | Terpinene 4 OL | 562-74-3 | 0.06 | 0.3 |
| | Alpha Terpinene | 99-86-5 | 0.1 | 10 |
| | Bomneol L | 507-70-0 | 0.1 | 5 |
| | Camphene | 79-92-5 | 0.1 | 2 |
| | Decanal | 112-31-2 | 0.08 | 0.6 |
| | Dodecanal | 112-54-9 | 0.06 | 0.3 |
| | Fenchol Alpha | 512-13-0 | 0.001 | 0.1 |

TABLE 1-continued

BLENDS

| | Compounds | CAS Registry Number | low % | high % |
|---|---|---|---|---|
| | Geranyl Acetate | 105-87-3 | 0.08 | 0.6 |
| | Isoborneol | 124-76-5 | 0.1 | 2 |
| | 2-Methyl 1,3-cyclohexadiene | 30640-46-1, 1888-90-0 | 0.1 | 2 |
| | Myrcene | 123-35-3 | 0.1 | 4 |
| | Nonanal | 124-19-6 | 0.001 | 0.1 |
| | Octanal | 124-13-0 | 0.05 | 0.2 |
| | Tocopherol Gamma (TENOX ®) | 54-28-4 | 0.001 | 0.1 |
| Blend 66 | D-Limonene | 5989-27-5 | 30 | 99 |
| | Linalool Coeur | 78-70-6 | 0.1 | 5 |
| | gamma-terpinene | 99-85-4 | 6 | 40 |
| | Alpha-Pinene, 98% | 80-56-8 | 0.1 | 8 |
| | Terpinolene | 586-62-9 | 0.1 | 25 |
| | Para-Cymene | 99-87-6 | 0.1 | 6 |
| | Linalyl Acetate | 115-95-7 | 0.1 | 10 |
| | Beta Pinene | 127-91-3 | 0.1 | 10 |
| | Camphor Dextro | 464-49-3 | 0.1 | 10 |
| | Terpinene 4 OL | 562-74-3 | 0.06 | 0.3 |
| | Alpha Terpinene | 99-86-5 | 0.08 | 0.6 |
| | Borneol L | 507-70-0 | 0.1 | 5 |
| | Camphene | 79-92-5 | 0.1 | 3 |
| | Decanal | 112-31-2 | 0.08 | 0.6 |
| | Dodecanal | 112-54-9 | 0.08 | 0.6 |
| | Fenchol Alpha | 512-13-0 | 0.001 | 0.1 |
| | Geranyl Acetate | 105-87-3 | 0.08 | 0.6 |
| | Isoborneol | 124-76-5 | 0.1 | 2 |
| | 2-Methyl 1,3-cyclohexadiene | 30640-46-1, 1888-90-0 | 0.1 | 2 |
| | Myrcene | 123-35-3 | 0.1 | 5 |
| | Nonanal | 124-19-6 | 0.001 | 0.2 |
| | Octanal | 124-13-0 | 0.05 | 0.3 |
| | Tocopherol Gamma (TENOX ®) | 54-28-4 | 0.001 | 0.2 |
| Blend 67 | D-Limonene | 5989-27-5 | 20 | 99 |
| | Linalool Coeur | 78-70-6 | 5 | 30 |
| | Alpha-Pinene, 98% | 80-56-8 | 0.1 | 15 |
| | Terpinolene | 586-62-9 | 5 | 30 |
| | Para-Cymene | 99-87-6 | 5 | 30 |
| | Linalyl Acetate | 115-95-7 | 0.1 | 15 |
| | Beta Pinene | 127-91-3 | 0.1 | 15 |
| | Alpha Terpinene | 99-86-5 | 0.1 | 15 |
| | Camphene | 79-92-5 | 0.1 | 20 |
| | Myrcene | 123-35-3 | 0.1 | 30 |
| Blend 68 | D-Limonene | 5989-27-5 | 0.08 | 1 |
| | Thyme Oil Red | 8007-46-3 | 0.1 | 4 |
| | Thymol (crystal) | 89-83-8 | 30 | 99 |
| | alpha-Terpineol | 98-55-5 | 0.1 | 6 |
| | Para-Cymene | 99-87-6 | 10 | 60 |
| | Linalyl Acetate | 115-95-7 | 0.1 | 5 |
| | Caryophyllene-B | 87-44-5 | 0.1 | 10 |
| | Borneol L | 507-70-0 | 0.1 | 6 |
| | Myrcene | 123-35-3 | 0.1 | 4 |
| | Tea Tree Oil | | 0.1 | 6 |
| | Cypress Oil | | 0.1 | 10 |
| | Peppermint Terpenes | 8006-90-4 | 0.1 | 30 |
| | Linalool 90 | | 0.1 | 10 |
| Blend 69 | D-Limonene | 5989-27-5 | 30 | 99 |
| | Citral | 5392-40-5 | 0.1 | 25 |
| | gamma-terpinene | 99-85-4 | 5 | 30 |
| | Alpha-Pinene, 98% | 80-56-8 | 0.1 | 5 |
| | alpha-Terpineol | 98-55-5 | 0.1 | 15 |
| | Terpinolene | 586-62-9 | 0.1 | 20 |
| | Lime Distilled Oil | | 0.06 | 0.3 |
| | Lime Expressed Oil | | 0.06 | 0.3 |
| | Linalyl Acetate | 115-95-7 | 0.1 | 6 |
| | Caryophyllene-B | 87-44-5 | 0.06 | 0.3 |
| | Beta Pinene | 127-91-3 | 0.1 | 8 |
| | Terpinene 4 OL | 562-74-3 | 0.005 | 0.2 |
| | Alpha Terpinene | 99-86-5 | 0.1 | 6 |
| | Borneol L | 507-70-0 | 0.1 | 5 |
| | Camphene | 79-92-5 | 0.1 | 2 |
| | Geranyl Acetate | 105-87-3 | 0.08 | 0.6 |
| | Isoborneol | 124-76-5 | 0.06 | 0.3 |
| | Linalool 90 | | 0.1 | 3 |
| | Camphor Gum | | 0.005 | 0.2 |
| | Aldehyde C-10 | | 0.005 | 0.2 |
| | Aldehyde C-12 | | 0.06 | 0.3 |
| Blend 70 | Eugenol | 97-53-0 | 0.003 | 0.1 |
| | Eucalyptol (1,8 Cineole) | | 0.05 | 0.3 |
| | Methyl Salicylate | | 60 | 99.9 |
| | Linalool 90 | | 0.05 | 0.3 |
| | Ethyl Salicylate | | 0.05 | 0.3 |
| Blend 71 | Tetrahydrolinalool | 78-69-3 | 6 | 35 |
| | Hercolyn D | 8050-15-5 | 0.1 | 25 |
| | Isopropyl myristate | 110-27-0 | 0.1 | 20 |
| | Piperonal (aldehyde)[Heliotropine] | 120-57-0 | 5 | 30 |
| | Ethyl Linalool | 10339-55-6 | 5 | 30 |
| | Triethyl Citrate | 77-93-0 | 0.1 | 30 |
| | Dipropylene glycol (DPG) | 246-770-3 | 5 | 30 |
| | Cinnamic Alcohol | 104-54-1 | 0.1 | 5 |
| | Eugenol | 97-53-0 | 0.1 | 5 |
| | Phenyl Ethyl Alcohol | 60-12-8 | 10 | 65 |
| | Iso Eugenol | | 0.08 | 1 |
| | Methyl Dihydrojasmonate | | 5 | 30 |
| Blend 72 | Linalool Coeur | 78-70-6 | 8 | 40 |
| | Tetrahydrolinalool | 78-69-3 | 10 | 70 |
| | Vanillin | 121-33-5 | 0.1 | 8 |
| | Isopropyl myristate | 110-27-0 | 15 | 85 |
| | Piperonal (aldehyde)[Heliotropine] | 120-57-0 | 5 | 30 |
| | Piperonyl Alcohol | 495-76-1 | 5 | 30 |
| | Geraniol Fine FCC | 106-24-1 | 5 | 30 |
| Blend 73 | Blend 11 | | 50 | 99 |
| | Stock 10% SLS Solution | | 5 | 30 |
| Blend 74 | Polyglycerol-4-oleate | 9007-48-1 | 0.1 | 3 |
| | Lecithin | 8002-43-5 | 0.08 | 0.6 |
| | Water | 7732-18-5 | 5 | 30 |
| | Blend 11 | | 50 | 99 |
| Blend 75 | Potassium Sorbate | 590-00-1 or 24634-61-5 | 0.1 | 4 |
| | Xanthan Gum | 11138-66-2 | 0.08 | 1 |
| | Water | 7732-18-5 | 45 | 99 |
| | Blend 74 | | 10 | 50 |
| Blend 76 | Potassium Sorbate | 590-00-1 or 24634-61-5 | 0.1 | 2 |
| | Polyglycerol-4-oleate | 9007-48-1 | 0.1 | 2 |
| | Xanthan Gum | 11138-66-2 | 0.08 | 1 |
| | Lecithin | 8002-43-5 | 0.06 | 0.3 |
| | Water | 7732-18-5 | 20 | 99 |
| | Blend 11 | | 15 | 99 |
| Blend 77 | Thyme Oil White | 8007-46-3 | 0.1 | 25 |
| | Wintergreen Oil | 68917-75-9 | 2 | 55 |
| | Isopropyl myristate | 110-27-0 | 1 | 40 |
| | Potassium Sorbate | 590-00-1 or 24634-61-5 | 0.06 | 0.3 |
| | Polyglycerol-4-oleate | 9007-48-1 | 0.1 | 2 |
| | Xanthan Gum | 11138-66-2 | 0.08 | 1 |
| | Lecithin | 8002-43-5 | 0.06 | 0.3 |
| | Water | 7732-18-5 | 20 | 99 |
| Blend 78 | Polyglycerol-4-oleate | 9007-48-1 | 0.1 | 3 |
| | Lecithin | 8002-43-5 | 0.08 | 0.6 |
| | Water | 7732-18-5 | 5 | 30 |
| | Blend 11 | | 50 | 99 |
| Blend 79 | Water | 7732-18-5 | 0.1 | 20 |
| | Blend 74 | | 40 | 99 |
| | Stock 2.5% Xanthan-1% Ksorbate | | 6 | 40 |
| Blend 80 | Water | 7732-18-5 | 0.1 | 10 |
| | Blend 78 | | 45 | 99 |
| | Stock 2.5% Xanthan-1% Ksorbate | | 6 | 40 |

TABLE 1-continued

BLENDS

| | Compounds | CAS Registry Number | low % | high % |
|---|---|---|---|---|
| Blend 81 | Potassium Sorbate | 590-00-1 or 24634-61-5 | 0.1 | 4 |
| | Xanthan Gum | 11138-66-2 | 0.08 | 1 |
| | Water | 7732-18-5 | 45 | 99 |
| | Blend 78 | | 10 | 50 |
| Blend 82 | Blend 1 | | 0.1 | 8 |
| | Water | | 60 | 99 |
| Blend 83 | Polyglycerol-4-oleate | 9007-48-1 | 0.1 | 3 |
| | Lecithin | 8002-43-5 | 0.08 | 0.6 |
| | Water | 7732-18-5 | 5 | 30 |
| | Blend 11 | | 50 | 99 |
| Blend 84 | Potassium Sorbate | 590-00-1 or 24634-61-5 | 0.1 | 4 |
| | Xanthan Gum | 11138-66-2 | 0.08 | 1 |
| | Water | 7732-18-5 | 45 | 99 |
| | Blend 83 | | 10 | 50 |
| Blend 85 | Citronella Oil | 106-22-9 | 0.08 | 0.6 |
| | Carbopol 940 | [9003-01-4] | 0.08 | 0.6 |
| | BHT (butylated hydroxytoluene) | 128-37-0 | 0.06 | 0.3 |
| | Water | 7732-18-5 | 30 | 99 |
| | Emulsifying Wax | 67762-27-0, 9005-67-8 | 8 | 40 |
| | Light Liquid Paraffin | 8012-95-1 | 0.1 | 10 |
| | White Soft Paraffin | [8009-03-8] | 0.1 | 25 |
| | Sodium Metabisulphate | [7681-57-4] | 0.08 | 1 |
| | Propylene Glycol | [57-55-6] | 0.1 | 6 |
| | Methyl Paraben | 199-76-3] | 0.08 | 0.6 |
| | Propyl Paraben | [94-133] | 0.005 | 0.2 |
| | Cresmer RH40 hydrogenated castor oil | [61791-12-6] | 0.1 | 15 |
| | Triethanolamine | [102-71-6] | 0.08 | 0.6 |
| | Vitamin E Acetate | 58-95-7] | 0.002 | 0.08 |
| | Disodium EDTA | [139-33-3] | 0.005 | 0.2 |
| | Blend 1 | | 0.1 | 15 |
| Blend 86 | Span 80 | 1338-43-8 | 0.005 | 0.2 |
| | Sodium Benzoate | 532-32-1 | 0.08 | 0.6 |
| | Isopar M | 64742-47-8 | 15 | 85 |
| | A46 Propellant | | 8 | 45 |
| | Water | 7732-18-5 | 25 | 99 |
| | Isopropyl alcohol | 67-63-0 | 0.1 | 5 |
| | Blend 8 | | 6 | 40 |
| Blend 87 | Isopar M. | 64742-47-8 | 30 | 99 |
| | A46 Propellant | | 20 | 99 |
| | Isopropyl alcohol | 67-63-0 | 0.1 | 10 |
| | Blend 25 | | 0.1 | 20 |
| Blend 88 | Isopar M | 64742-47-8 | 30 | 99 |
| | A46 Propellant | | 20 | 99 |
| | Bifenthrin | 83657-04-3 | 0.005 | 0.2 |
| | Isopropyl alcohol | 67-63-0 | 0.1 | 10 |
| | Blend 25 | | 0.1 | 20 |
| Blend 89 | Isopar M | 64742-47-8 | 30 | 99 |
| | A46 Propellant | | 20 | 99 |
| | Blend 20 | | 0.1 | 20 |
| Blend 90 | Potassium Sorbate | 590-00-1 or 24634-61-5 | 0.06 | 0.3 |
| | Polyglycerol-4-oleate | 9007-48-1 | 0.08 | 0.6 |
| | Xanthan Gum | 11138-66-2 | 0.08 | 0.6 |
| | Lecithin | 8002-43-5 | 0.003 | 0.1 |
| | Water | 7732-18-5 | 45 | 99 |
| | Isopropyl alcohol | 67-63-0 | 0.1 | 8 |
| | Blend 35 | | 8 | 45 |
| Blend 91 | Potassium Sorbate | 590-00-1 or 24634-61-5 | 0.06 | 0.3 |
| | Polyglycerol-4-oleate | 9007-48-1 | 0.08 | 0.6 |
| | Xanthan Gum | 11138-66-2 | 0.08 | 1 |
| | Lecithin | 8002-43-5 | 0.003 | 0.1 |
| | Water | 7732-18-5 | 50 | 99 |
| | Blend 35 | | 8 | 40 |
| Blend 92 | Isopropyl myristate | 110-27-0 | 0.1 | 10 |
| | Geraniol Fine FCC | 106-24-1 | 0.1 | 8 |
| | Potassium Sorbate | 590-00-1 or 24634-61-5 | 0.06 | 0.3 |
| | Polyglycerol-4-oleate | 9007-48-1 | 0.1 | 2 |
| | Xanthan Gum | 11138-66-2 | 0.08 | 1 |
| | Lecithin | 8002-43-5 | 0.05 | 0.2 |
| | Water | 7732-18-5 | 3 | 99 |
| | Blend 68 | | 0.1 | 10 |
| | Isopropyl alcohol | 67-63-0 | 0.1 | 8 |
| Blend 93 | Wintergreen Oil | 68917-75-9 | 0.1 | 15 |
| | Isopropyl myristate | 110-27-0 | 0.1 | 10 |
| | Thyme Oil Red | 8007-46-3 | 0.1 | 6 |
| | Stock 0.3% SLS-0.1% Xanthan Soln | | 55 | 99 |
| Blend 94 | Stock 0.3% SLS & 0.1% Xanthan Soln | | 60 | 99 |
| | Blend 38 | | 0.1 | 15 |
| Blend 95 | Lecithin, Soya | 8030-76-0 | 0.08 | 0.6 |
| | Polyglycerol-4-oleate | 9007-48-1 | 0.1 | 3 |
| | Water | 7732-18-5 | 5 | 30 |
| | Blend 11 | | 50 | 99 |
| Blend 96 | Thyme Oil White | 8007-46-3 | 20 | 99 |
| | Isopropyl myristate | 110-27-0 | 15 | 95 |
| | Lecithin, Soya | 8030-76-0 | 0.08 | 0.6 |
| | Polyglycerol-4-oleate | 9007-48-1 | 0.1 | 3 |
| | Water | 7732-18-5 | 5 | 30 |
| | Wintergreen Oil | | 10 | 65 |
| Blend 97 | Lecithin, Soya | 8030-76-0 | 0.06 | 0.3 |
| | Polyglycerol-4-oleate | 9007-48-1 | 0.1 | 3 |
| | Water | 7732-18-5 | 5 | 30 |
| | Blend 7 | | 50 | 99 |
| Blend 98 | Thyme Oil White | 8007-46-3 | 10 | 55 |
| | Wintergreen Oil | 68917-75-9 | 20 | 99 |
| | Vanillin | 121-33-5 | 0.1 | 4 |
| | Isopropyl myristate | 110-27-0 | 15 | 90 |
| | Lecithin, Soya | 8030-76-0 | 0.06 | 0.3 |
| | Polyglycerol-4-oleate | 9007-48-1 | 0.1 | 3 |
| | Water | 7732-18-5 | 5 | 30 |
| Blend 99 | Polyglycerol-4-oleate | 9007-48-1 | 0.1 | 6 |
| | Water | 7732-18-5 | 0.1 | 25 |
| | Blend 11 | | 50 | 99 |
| Blend 100 | Thyme Oil White | 8007-46-3 | 20 | 99 |
| | Isopropyl myristate | 110-27-0 | 15 | 95 |
| | Polyglycerol-4-oleate | 9007-48-1 | 0.1 | 6 |
| | Water | 7732-18-5 | 0.1 | 25 |
| | Wintergreen Oil | | 10 | 65 |
| Blend 101 | Potassium Sorbate | 590-00-1 or 24634-61-5 | 0.06 | 0.3 |
| | Polyglycerol-4-oleate | 9007-48-1 | 0.1 | 6 |
| | Xanthan Gum | 11138-66-2 | 0.08 | 1 |
| | Water | 7732-18-5 | 50 | 99 |
| | Blend 97 | | 6 | 35 |
| Blend 102 | D-Limonene | 5989-27-5 | 0.1 | 15 |
| | Thyme Oil White | 8007-46-3 | 0.1 | 5 |
| | Lecithin, Soya | 8030-76-0 | 0.001 | 0.04 |
| | Potassium Sorbate | 590-00-1 or 24634-61-5 | 0.06 | 0.3 |
| | Polyglycerol-4-oleate | 9007-48-1 | 0.1 | 6 |
| | Xanthan Gum | 11138-66-2 | 0.08 | 1 |
| | Water | 7732-18-5 | 50 | 99 |
| | Wintergreen Oil | | 0.1 | 10 |
| Blend 103 | Potassium Sorbate | 590-00-1 or 24634-61-5 | 0.06 | 0.3 |
| | Xanthan Gum | 11138-66-2 | 0.08 | 1 |
| | Water | 7732-18-5 | 50 | 99 |
| | Blend 95 | | 6 | 35 |
| Blend 104 | Thyme Oil White | 8007-46-3 | 0.1 | 10 |
| | Isopropyl myristate | 110-27-0 | 0.1 | 10 |
| | Lecithin, Sova | 8030-76-0 | 0.002 | 0.08 |
| | Potassium Sorbate | 590-00-1 or 24634-61-5 | 0.06 | 0.3 |
| | Polyglycerol-4-oleate | 9007-48-1 | 0.06 | 0.3 |
| | Xanthan Gum | 11138-66-2 | 0.08 | 1 |
| | Water | 7732-18-5 | 55 | 99 |
| | Wintergreen Oil | | 0.1 | 8 |
| Blend 105 | Potassium Sorbate | 590-00-1 or 24634-61-5 | 0.06 | 0.3 |

TABLE 1-continued

BLENDS

| | Compounds | CAS Registry Number | low % | high % |
|---|---|---|---|---|
| | Xanthan Gum | 11138-66-2 | 0.08 | 1 |
| | Water | 7732-18-5 | 50 | 99 |
| | Blend 99 | | 6 | 35 |
| Blend 106 | Thyme Oil White | 8007-46-3 | 0.1 | 10 |
| | Wintergreen Oil | 68917-75-9 | 0.1 | 8 |
| | Isopropyl myristate | 110-27-0 | 0.1 | 10 |
| | Potassium Sorbate | 590-00-1 or 24634-61-5 | 0.06 | 0.3 |
| | Polyglycerol-4-oleate | 9007-48-1 | 0.08 | 0.6 |
| | Xanthan Gum | 11138-66-2 | 0.08 | 1 |
| | Water | 7732-18-5 | 55 | 99 |
| Blend 107 | Potassium Sorbate | 590-00-1 or 24634-61-5 | 0.1 | 4 |
| | Xanthan Gum | 11138-66-2 | 0.1 | 8 |
| | Water | 7732-18-5 | 60 | 99 |
| Blend 108 | Sodium Benzoate | 532-32-1 | 0.1 | 6 |
| | Water | 7732-18-5 | 60 | 99 |
| Blend 109 | Span 80 | 1338-43-8 | 0.1 | 4 |
| | Tween 80 | | 0.1 | 5 |
| | Isopar M | 64742-47-8 | 8 | 40 |
| | Water | 7732-18-5 | 35 | 99 |
| | Blend 8 | | 0.1 | 10 |
| | 2% Sodium Benzoate | | 6 | 35 |
| Blend 110 | D-Limonene | 5989-27-5 | 0.1 | 5 |
| | Thyme Oil White | 8007-46-3 | 0.1 | 2 |
| | Wintergreen Oil | 68917-75-9 | 0.1 | 3 |
| | Span 80 | 1338-43-8 | 0.1 | 4 |
| | Tween 80 | | 0.1 | 5 |
| | Sodium Benzoate | 532-32-1 | 0.08 | 0.6 |
| | Isopar M | 64742-47-8 | 8 | 40 |
| | Water | 7732-18-5 | 40 | 99 |
| Blend 111 | Propellent A70 | | 10 | 65 |
| | Blend 109 | | 45 | 99 |
| Blend 112 | D-Limonene | 5989-27-5 | 0.1 | 5 |
| | Thyme Oil White | 8007-46-3 | 0.08 | 1 |
| | Wintergreen Oil | 68917-75-9 | 0.1 | 3 |
| | Span 80 | 1338-43-8 | 0.1 | 3 |
| | Tween 80 | | 0.1 | 5 |
| | Sodium Benzoate | 532-32-1 | 0.08 | 0.6 |
| | Isopar M | 64742-47-8 | 6 | 35 |
| | Water | 7732-18-5 | 35 | 99 |
| | Propellent A70 | | 10 | 65 |
| Blend 113 | Sodium Lauryl Sulfate | 151-21-3 | 5 | 30 |
| | Water | 7732-18-5 | 55 | 99 |
| Blend 114 | Sodium Lauryl Sulfate | 151-21-3 | 0.08 | 1 |
| | Xanthan Gum | 11138-66-2 | 0.06 | 0.3 |
| | Water | 7732-18-5 | 60 | 99.9 |
| Blend 115 | Citronella Oil | 106-22-9 | 0.08 | 0.6 |
| | Carbopol 940 | [9003-01-4] | 0.08 | 0.6 |
| | BHT (butylated hydroxytoluene) | 128-37-0 | 0.06 | 0.3 |
| | Water | 7732-18-5 | 30 | 99 |
| | Emulsifying Wax | 67762-27-0, 9005-67-8 | 8 | 40 |
| | Light Liquid Paraffin | 8012-95-1 | 0.1 | 10 |
| | White Soft Paraffin | [8009-03-8] | 0.1 | 25 |
| | Sodium Metabisulphate | [7681-57-4] | 0.08 | 1 |
| | Propylene Glycol | [57-55-6] | 0.1 | 6 |
| | Cresmer RH40 hydrogenated castor oil | [61791-12-6] | 0.1 | 15 |
| | Triethanolamine | [102-71-6] | 0.08 | 0.6 |
| | Vitamin E Acetate | 58-95-7] | 0.002 | 0.08 |
| | Disodium EDTA | [139-33-3] | 0.005 | 0.2 |
| | Blend 1 | | 0.1 | 15 |
| Blend 116 | Water | 7732-18-5 | 20 | 99 |
| | Blend 75 | | 35 | 99 |
| Blend 117 | D-Limonene | 5989-27-5 | 0.1 | 10 |
| | Thyme Oil White | 8007-46-3 | 0.1 | 15 |
| | Benzyl Alcohol | 100-51-6 | 8 | 50 |
| | Isopar M | 64742-47-8 | 10 | 65 |
| | Water | 7732-18-5 | 25 | 99 |
| | Bifenthrin | 83657-04-3 | 0.005 | 0.2 |
| | Blend 63 | | 0.1 | 15 |
| | Stock 10% SLS Solution | | 0.1 | 10 |
| Blend 118 | Thyme Oil White | 8007-46-3 | 0.1 | 2 |
| | Wintergreen Oil | 68917-75-9 | 0.1 | 3 |
| | Isopropyl myristate | 110-27-0 | 0.1 | 3 |
| | Sodium Lauryl Sulfate | 151-21-3 | 0.002 | 0.08 |
| | Water | 7732-18-5 | 60 | 99 |
| Blend 119 | Thyme Oil White | 8007-46-3 | 0.1 | 4 |
| | Wintergreen Oil | 68917-75-9 | 0.1 | 8 |
| | Isopropyl myristate | 110-27-0 | 0.1 | 5 |
| | AgSorb clay carrier | | 60 | 99 |
| Blend 120 | Thyme Oil White | 8007-46-3 | 0.1 | 4 |
| | Wintergreen Oil | 68917-75-9 | 0.1 | 8 |
| | Isopropyl myristate | 110-27-0 | 0.1 | 5 |
| | DG Lite | | 60 | 99 |
| Blend 121 | D-Limonene | 5989-27-5 | 15 | 75 |
| | Thyme Oil White | 8007-46-3 | 0.1 | 4 |
| | Linalool Coeur | 78-70-6 | 0.08 | 0.6 |
| | Tetrahydrolinalool | 78-69-3 | 0.08 | 0.6 |
| | Vanillin | 121-335 | 0.002 | 0.08 |
| | Isopropyl myristate | 110-27-0 | 0.08 | 0.6 |
| | Piperonal (aldehyde) [Heliotropine] | 120-57-0 | 0.08 | 0.6 |
| | Blend 66 | | 0.1 | 10 |
| | Geraniol 60 | 106-24-1 | 0.06 | 0.3 |
| | Triethyl Citrate | 77-93-0 | 0.08 | 0.6 |
| | Water | 7732-18-5 | 35 | 99 |
| | Stock 10% SLS Solution | | 0.1 | 10 |
| Blend 122 | Miracle Gro (Sterile) | | 60 | 99 |
| | Blend 11 | | 0.1 | 15 |
| Blend 123 | Thyme Oil White | 8007-46-3 | 15 | 75 |
| | Amyl Butyrate | 540-18-1 | 15 | 75 |
| | Anise Star Oil | | 30 | 99 |
| | Genistein | | 0.001 | 0.1 |
| Blend 124 | Linalool Coeur | | 0.1 | 20 |
| | Tetrahydrolinalool | | 0.1 | 25 |
| | Vanillin | | 0.1 | 2 |
| | Isopropyl myristate | | 0.1 | 30 |
| | Piperonal (aldehyde) [Heliotropine] | | 0.1 | 30 |
| | Geraniol Fine FCC | | 0.1 | 15 |
| | Triethyl Citrate | | 0.1 | 30 |
| | Thyme Oil White | | 30 | 99 |
| Blend 125 | D-Limonene | 5989-27-5 | 5 | 30 |
| | Linalool Coeur | 78-70-6 | 8 | 40 |
| | Tetrahydrolinalool | 78-69-3 | 15 | 75 |
| | Vanillin | 121-33-5 | 0.1 | 8 |
| | Isopropyl myristate | 110-27-0 | 15 | 85 |
| | Piperonal (aldehyde) | 120-57-0 | 5 | 30 |
| | Geraniol 60 | | 5 | 30 |
| Blend 126 | D-Limonene | 5989-27-5 | 45 | 99 |
| | Thyme Oil White | 8007-46-3 | 0.1 | 10 |
| | Linalool Coeur | 78-70-6 | 0.1 | 2 |
| | Tetrahydrolinalool | 78-69-3 | 0.1 | 3 |
| | Vanillin | 121-33-5 | 0.005 | 0.2 |
| | Isopropyl myristate | 110-27-0 | 0.1 | 3 |
| | Piperonal (aldehyde) [Heliotropine] | 120-57-0 | 0.1 | 3 |
| | Blend 66 | | 5 | 30 |
| | Geraniol 60 | | 0.1 | 2 |
| | Triethyl Citrate | 77-93-0 | 0.1 | 3 |

Embodiments of the invention relate to compositions for controlling a target post, wherein the composition contains at least two active ingredients, and methods for using these compositions. The at least two active ingredients, when combined, can have a synergistic effect. Thus, for example, compositions of the invention can include any of the following oils listed below, or mixtures thereof:

| | | |
|---|---|---|
| amyl butyrate | linalool | tetrahydrolinalool |
| anise star oil | linalyl acetate | thyme oil (including |
| black seed oil (BSO) | methyl salicyclate | thyme oil white and |
| para-cymene | alpha-pinene (a-pinene) | thyme oil red) |
| geraniol | piperonal | thymol |
| isopropyl myristate | piperonyl | thymyl acetate |
| lilac flower oil (LFO) | piperonyl acetate | vanillin |
| d-limonene | piperonyl alcohol | wintergreen oil |

The compositions of the present invention can also include any of the following oils listed below, or mixtures thereof:

| | | |
|---|---|---|
| Allyl sulfide | Estragole | Nonanone |
| Allyl trisulfide | 2-ethyl-2-hexen-1-ol | 1-octanol |
| Allyl-disulfide | eugenol | E ocimenone |
| Anethole | Eugenol acetate | Z ocimenone |
| trans-anethole | α-farnesene | 3-octanone |
| Artemisia alcohol acetate | (Z,E)-α-farnesene | Ocimene |
| Benzyl acetate | E-β-farnesene | Octyl acetate |
| Benzyl alcohol | Fenehone | PD 98059 |
| Bergamotene | Forskolin | Peppermint oil |
| B-bisabolene | Furanodiene | perillyl alcohol |
| Bisabolene oxide | Furanoeudesma-1,3-diene | Permethrin |
| α-bisabolol | Furanoeudesma-1,4-diene | phenyl acetaldehyde |
| Bisabolol oxide | Furano germacra 1,10(15)- | phenylethyl alcohol |
| Bisobolol oxide β | diene-6-one | phenylethyl propionate |
| Bornyl acetate | Furanosesquiterpene | α-phellandrene |
| B-bourbonene | Geraniol | β-phellandrene |
| α-cadinol | Geraniol acetate | β-pinene |
| camphene | Germacrene D | piperonyl amine quinone |
| α-campholene | Germacrene B | Prenal |
| α-campholene aldehyde | α-gurjunene | Propargite |
| camphor | α-humulene | Pulegone |
| carbaryl | α-ionone | Pyrethrum |
| carvacrol | β-ionone | 2-tert-butyl-p-quinone |
| d-carvone | Isoborneol | Sabinene |
| l-carvone | Isofuranogermacrene | Sabinyl acetate |
| Caryophyllene oxide | Iso-menthone | α-santalene |
| Chamazulene | isopropyl citrate | Santalol |
| Chrysanthemate ester | Iso-pulegone | Sativen |
| Chrysanthemic acid | Jasmone | δ-selinene |
| Chrysanthemyl alcohol | cis-jasmone | β-sesquphelandrene |
| 1,8-cincole | Lavandustin A | Spathulenol |
| Cinnamaldehyde | lemon grass oil | Tagetone |
| Cis-verbenol | lime oil | Tamoxifen |
| Citral A | Limonene | Tebufenozide |
| Citral B | lindenol | α-terpinene |
| Citronellal | Lindestrene | terpinene 900 |
| Citronellol | linalyl anthranilate | 4-terpineol |
| Citronellyl acetate | Methyl-allyl-trisulfide | α-terpineol |
| Citronellyl formate | methyl citrate | gamma-terpineol |
| α-copaene | methyl di-hydrojasmonate | α-terpinolene |
| cornmint oil | Menthol | α-terpinyl acetate |
| β-costol | 2-methoxy furanodiene | tetrahydrofurfuryl alcohol. |
| Cryptone | menthone | α-thujene |
| Curzerenone | Menthyl acetate | α-thujone |
| Davanone | Menthyl salicylate | Thymyl methyl ether |
| Diallyl tetrasulfide | Methyl cinnamate | Trans-caryophyllene |
| Diethyl phthalate | Menthyl salicylate | Trans-pinocarveol |
| dihydropyrocurzerenone | myrcene | Trans-verbenol |
| β-elemene | Myrtenal | Verbenone |
| gamma-elemene | Neraldimethyl acetate | Yomogi alcohol |
| Elmol | Nerolidol | Zingiberene |
| | | Dihydrotagentone |

Optionally, the compositions can additionally include a fixed oil, which is a non-volatile non-scented plant oil. For example, the composition could include one or more of the following fixed oils listed below:

| | | |
|---|---|---|
| castor oil | mineral oil | safflower oil |
| corn oil | olive oil | sesame oil |
| cumin oil | peanut oil | soy bean oil |

In some embodiments of the compositions, it can be desirable to include compounds each having a purity of about 60%, 65%, 70%, 75%, 80%, 85%, 90%, or 95%. For example, in some embodiments of the compositions that include geraniol, it can be desirable to include a geraniol that is at least about 60%, 85% or 95% pure. In some embodiments, it can be desirable to include a specific type of geraniol. For example, in some embodiments, the compositions can include: geraniol 60, geraniol 85, or geraniol 95. When geraniol is obtained as geraniol 60, geraniol 85, or geraniol 95, then forty percent, fifteen percent, or five percent of the oil can be Nerol. Nerol is a monoterpene (C10H18O that can be extracted from attar of roses, oil of orange blossoms and oil of lavender.

In some other embodiments, each compound can make up between about 1% to about 99%, by weight (wt/wt %) or by volume (vol/vol %), of the composition. As used herein, percent amounts, by weight or by volume, of compounds are to be understood as referring to relative amounts of the compounds. As such, for example, a composition including 7% linalool, 35% thymol, 4% alpha-pinene, 30% para-cymene, and 24% soy bean oil (vol/vol %) can be said to include a ratio of 7 to 35 to 4 to 30 to 24 linalool, thymol, alpha-pinene, para-cymene, and soy bean oil, respectively (by volume). As such, if one compound is removed from the composition, or additional compounds or other ingredients are added to the composition, it is contemplated that the remaining compounds can be provided in the same relative amounts. For example, if soy bean oil were removed from the exemplary composition, the resulting composition would include 7 to 35 to 4 to 40 linalool, thymol, alpha-pinene, and para-cymene, respectively (by volume). This resulting composition would include 9.21% linalool, 46.05% thymol, 5.26% alpha-pinene, and 39.48% para-cymene (vol/vol %). For another example, if safflower oil were added to the original composition to yield a final composition containing 40% (vol/vol) safflower oil, then the resulting composition would include 4.2% linalool, 21% thymol, 2.4% alpha-pinene, 18% para-cymene, 14.4% soy bean oil, and 40% safflower oil (vol/vol %). One having ordinary skill in the art would understand that volume percentages are easily converted to weight percentages based the known or measured specific gravity of the substance.

In some embodiments, it can be desirable to include a naturally-occurring version or a synthetic version of a compound. For example, in some embodiments it can be desirable to include a synthetic lime oil that can be obtained commercially. In certain exemplary compositions, it can be desirable to include a compound that is designated as meeting Food Chemical Codex (FCC), for example, Geraniol Fine FCC or Tetrahydrolinaool FCC, which compounds can be obtained commercially.

Additional Composition Components

Embodiments of the present invention can include art-recognised ingredients normally used in such formulations. These ingredients can include, for example, antifoaming agents, anti-microbial agents, anti-oxidants, anti-redeposition agents, bleaches, colorants, emulsifiers, enzymes, fats, fluorescent materials, fungicides, hydrotropes, moisturisers, optical brighteners, perfume carriers, perfume, preservatives, proteins, silicones, soil release agents, solubilisers, sugar derivatives, sun screens, surfactants, vitamins waxes, and the like.

In some embodiments, the compositions can also contain other adjuvants or modifiers such as one or more therapeutically or cosmetically active ingredients. Exemplary therapeutic or cosmetically active ingredients useful in the compositions of the invention can include, for example, fungicides, sunscreening agents, sunblocking agents, vitamins, tanning agents, plant extracts, anti-inflammatory agents, anti-oxidants, radical scavenging agents, retinoids, alpha-hydroxy acids, emollients, antiseptics, antibiotics, antibacterial agents, antihistamines, and the like, and can be present in an amount effective for achieving the therapeutic or cosmetic result desired.

In some embodiments, the compositions can include one or more materials that can function as an antioxidant, such as reducing agents and free radical scavengers. Suitable materials that can function as an antioxidant can include, for example: acetyl cysteine, ascorbic acid, t-butyl hydroquinone, cysteine, diamylhydroquinone, erythorbic acid, ferulic acid, hydroquinone, p-hydroxyanisole, hydroxylamine sulfate, magnesium ascorbate, magnesium ascorbyl phosphate, octocrylene, phloroglucinol, potassium ascorbyl tocopheryl phosphate, potassium sulfite, rutin, sodium ascorbate, sodium sulfite, sodium thloglycolate, thiodiglycol, thiodiglycolamide, thioglycolic acid, thiosalicylic acid, tocopherol, tocopheryl acetate, tocopheryl linoleate, tris(nonylpheny)phosphite, and the like.

Embodiments of the invention can also include one or more materials that can function as a chelating agent to complex with metallic ions. This action can help to inactivate the metallic ions for the purpose of preventing their adverse effects on the stability or appearance of a formulated composition. Chelating agents suitable for use in an embodiment of this invention can include, for example, aminotrimethylene phosphonic acid, beta-alanine diacetic acid, calcium disodium EDTA, citric acid, cyclodextrin, cyclohexanediamine tetraacetic acid, diammonium citrate, diammonium EDTA, dipotassium EDTA, disodium azacycloheptane diphosphonate, disodium EDTA, disodium pyrophosphate, EDTA (ethylene diamine tetra acetic acid), gluconic acid, HEDTA (hydroxyethyl ethylene diamine triacetic acid), methyl cyclodextrin, pentapotassium triphosphate, pentasodium aminotrimethylene phosphonate, pentasodium triphosphate, pentetic acid, phytic acid, potassium citrate, potassium gluconate, sodium citrate, sodium diethylenetriamine pentamethylene phosphonate, sodium dihydroxyethylglycinate, sodium gluconate, sodium metaphosphate, sodium metasilicate, sodium phytate, triethanolamine ("TEA")-EDTA, TEA-polyphosphate, tetrahydroxypropyl ethylenediamine, tetrapotassium pyrophosphate, tetrasodium EDTA, tetrasodium pyrophosphate, tripotassium EDTA, trisodium EDTA, trisodium HEDTA, trisodium phosphate, and the like.

Embodiments of the invention can also include one or more materials that can function as a humectant. A humectant is added to a composition to retard moisture loss during use, which effect is accomplished, in general, by the presence therein of hygroscopic materials.

The following table (Table 2) provides exemplary compositions of embodiments of the invention:

TABLE 2

Exemplary Compositions

| Ingredients | Exemplified form | % Range 1 | | % Range 2 | | % Range 3 | | % Range 4 | | Exemplified % (w/w) |
|---|---|---|---|---|---|---|---|---|---|---|
| Example 1 - Ingredient Family 1 | | | | | | | | | | |
| Linalool | Linalool Coeur | 0.66% | 19.80% | 3.30% | 9.90% | 4.95% | 8.25% | 5.94% | 7.26% | 6.60% |
| Base Oil | Soy Bean Oil | 2.40% | 72.00% | 12.00% | 36.00% | 18.00% | 30.00% | 21.60% | 26.40% | 24.00% |
| Thymol | Thymol (crystal) | 3.72% | 99.00% | 18.60% | 55.80% | 27.90% | 46.50% | 33.48% | 40.92% | 37.20% |
| Pinene | Alpha-Pinene, 98% | 0.38% | 11.40% | 1.90% | 5.70% | 2.85% | 4.75% | 3.42% | 4.18% | 3.80% |
| Cymene | Para-Cymene | 2.84% | 85.17% | 14.20% | 42.59% | 21.29% | 35.49% | 25.55% | 31.23% | 28.39% |
| Example 2 - Ingredient Family 2 | | | | | | | | | | |
| Thyme Oil | Thyme Oil White | 2.06% | 61.80% | 10.30% | 30.90% | 15.45% | 25.75% | 18.54% | 22.66% | 20.60% |
| Wintergreen Oil | Wintergreen Oil | 4.51% | 99.00% | 22.55% | 67.65% | 33.83% | 56.38% | 40.59% | 49.61% | 45.10% |
| Isopropyl myristate | Isopropyl myristate | 3.43% | 99.00% | 17.15% | 51.45% | 25.73% | 42.88% | 30.87% | 37.73% | 34.30% |
| Example 3 - Ingredient Family 3 | | | | | | | | | | |
| Thyme Oil | Thyme Oil White | 2.48% | 74.25% | 12.38% | 37.13% | 18.56% | 30.94% | 22.28% | 27.23% | 24.75% |
| Amyl Butyrate | Amyl Butyrate | 2.30% | 69.12% | 11.52% | 34.56% | 17.28% | 28.80% | 20.74% | 25.34% | 23.04% |
| Anise Star Oil | Anise Star Oil | 5.22% | 99.00% | 26.11% | 78.32% | 39.16% | 65.26% | 46.99% | 57.43% | 52.21% |
| Example 4 - Ingredient Family 4 | | | | | | | | | | |
| Thyme Oil | Thyme Oil White | 2.48% | 74.25% | 12.38% | 37.13% | 18.56% | 30.94% | 22.28% | 27.23% | 24.75% |
| Amyl Butyrate | Amyl Butyrate | 2.30% | 69.12% | 11.52% | 34.56% | 17.28% | 28.80% | 20.74% | 25.34% | 23.04% |
| Anise Star Oil | Anise Star Oil | 5.22% | 99.00% | 26.10% | 78.30% | 39.15% | 65.25% | 46.98% | 57.42% | 52.20% |
| Isoflavone | Genistein | 0.001% | 5.00% | 0.005% | 0.02% | 0.008% | 0.012% | 0.009% | 0.011% | 0.01% |
| Example 5 - Ingredient Family 5 | | | | | | | | | | |
| Thyme Oil | Thyme Oil White | 2.05% | 61.50% | 10.25% | 30.75% | 15.38% | 25.63% | 18.45% | 22.55% | 20.50% |
| Wintergreen Oil | Wintergreen Oil | 4.50% | 99.00% | 22.50% | 67.50% | 33.75% | 56.25% | 40.50% | 49.50% | 45.00% |
| Vanillin | Vanillin | 0.11% | 5.00% | 0.55% | 1.65% | 0.83% | 1.38% | 0.99% | 1.21% | 1.10% |
| Isopropyl myristate | Isopropyl myristate | 3.34% | 99.00% | 16.70% | 50.10% | 25.05% | 41.75% | 30.06% | 36.74% | 33.40% |
| Example 6 - Ingredient Family 6 | | | | | | | | | | |
| Limonene | D-Limonene | 5.63% | 99.00% | 28.15% | 84.45% | 42.23% | 70.38% | 50.67% | 61.93% | 56.30% |
| Thyme Oil | Thyme Oil White | 1.24% | 37.14% | 6.19% | 18.57% | 9.29% | 15.48% | 11.14% | 13.62% | 12.38% |
| Wintergreen Oil | Wintergreen Oil | 3.13% | 93.96% | 15.66% | 46.98% | 23.49% | 39.15% | 28.19% | 34.45% | 31.32% |

TABLE 2-continued

Exemplary Compositions

| Ingredients | Exemplified form | % Range 1 | | % Range 2 | | % Range 3 | | % Range 4 | | Exemplified % (w/w) |
|---|---|---|---|---|---|---|---|---|---|---|
| Example 7 - Ingredient Family 7 | | | | | | | | | | |
| Potassium Sorbate | Potassium Sorbate | 0.10% | 5.00% | 0.50% | 1.50% | 0.75% | 1.25% | 0.90% | 1.10% | 1.00% |
| Xanthan Gum | Xanthan Gum | 0.03% | 5.00% | 0.14% | 0.42% | 0.21% | 0.35% | 0.25% | 0.31% | 0.28% |
| Water | Water | 8.18% | 99.00% | 40.91% | 99.00% | 61.37% | 99.00% | 73.64% | 90.00% | 81.82% |
| Blend 74 | Blend 74 | 1.69% | 50.7% | 8.45% | 25.35% | 12.68% | 21.13% | 15.21% | 18.59% | 16.90% |
| Example 8 - Ingredient Family 8 | | | | | | | | | | |
| Isopropyl myristate | Isopropyl myristate | 4.84% | 99.00% | 24.18% | 72.53% | 36.26% | 60.44% | 43.52% | 53.19% | 48.35% |
| Geraniol | Geraniol Fine FCC | 1.50% | 44.94% | 7.49% | 22.47% | 11.24% | 18.73% | 13.48% | 16.48% | 14.98% |
| Blend 68 | Blend 68 | 3.67% | 99.00% | 18.34% | 55.01% | 27.50% | 45.84% | 33.00% | 40.34% | 36.67% |
| Example 9 - Ingredient Family 9 | | | | | | | | | | |
| Limonene | D-Limonene | 0.99% | 29.70% | 4.95% | 14.85% | 7.43% | 12.38% | 8.91% | 10.89% | 9.90% |
| Linalool | Linalool Coeur | 1.41% | 42.42% | 7.07% | 21.21% | 10.61% | 17.68% | 12.73% | 15.55% | 14.14% |
| Tetrahydrolinalool | Tetrahydrolinalool | 2.43% | 72.87% | 12.15% | 36.44% | 18.22% | 30.36% | 21.86% | 26.72% | 24.29% |
| Vanillin | Vanillin | 0.25% | 7.44% | 1.24% | 3.72% | 1.86% | 3.10% | 2.23% | 2.73% | 2.48% |
| Isopropyl myristate | Isopropyl myristate | 2.89% | 86.76% | 14.46% | 43.38% | 21.69% | 36.15% | 26.03% | 31.81% | 28.92% |
| Piperonal | Piperonal (aldehyde) | 1.00% | 29.91% | 4.99% | 14.96% | 7.48% | 12.46% | 8.97% | 10.97% | 9.97% |
| Geraniol | Geraniol Fine FCC | 1.03% | 30.90% | 5.15% | 15.45% | 7.73% | 12.88% | 9.27% | 11.33% | 10.30% |
| Example 10 - Ingredient Family 10 | | | | | | | | | | |
| Limonene | D-Limonene | 2.85% | 85.38% | 14.23% | 42.69% | 21.35% | 35.58% | 25.61% | 31.31% | 28.46% |
| Thyme Oil | Thyme Oil White | 3.13% | 93.87% | 15.65% | 46.94% | 23.47% | 39.11% | 28.16% | 34.42% | 31.29% |
| Blend 63 | Blend 63 | 4.03% | 99.00% | 20.13% | 60.38% | 30.19% | 50.31% | 36.23% | 44.28% | 40.25% |
| Example 11 - Ingredient Family 11 | | | | | | | | | | |
| Limonene | D-Limonene | 0.96% | 28.89% | 4.82% | 14.45% | 7.22% | 12.04% | 8.67% | 10.59% | 9.63% |
| BSO | BSO | 2.67% | 79.98% | 13.33% | 39.99% | 20.00% | 33.33% | 23.99% | 29.33% | 26.66% |
| Linalool | Linalool Coeur | 0.98% | 29.46% | 4.91% | 14.73% | 7.37% | 12.28% | 8.84% | 10.80% | 9.82% |
| Tetrahydrolinalool | Tetrahydrolinalool | 1.18% | 35.43% | 5.91% | 17.72% | 8.86% | 14.76% | 10.63% | 12.99% | 11.81% |
| Vanillin | Vanillin | 0.12% | 5.00% | 0.60% | 1.80% | 0.90% | 1.50% | 1.08% | 1.32% | 1.20% |
| Base Oil | Mineral Oil White USP | 1.50% | 44.91% | 7.49% | 22.46% | 11.23% | 18.71% | 13.47% | 16.47% | 14.97% |
| Isopropyl myristate | Isopropyl myristate | 1.45% | 43.62% | 7.27% | 21.81% | 10.91% | 18.18% | 13.09% | 15.99% | 14.54% |
| Piperonal | Piperonal (aldehyde) | 0.49% | 14.55% | 2.43% | 7.28% | 3.64% | 6.06% | 4.37% | 5.34% | 4.85% |
| Geraniol | Geraniol Fine FCC | 0.65% | 19.53% | 3.26% | 9.77% | 4.88% | 8.14% | 5.86% | 7.16% | 6.51% |
| Example 12 - Ingredient Family 12 | | | | | | | | | | |
| Thyme Oil | Thyme Oil White | 4.19% | 99.00% | 20.93% | 62.79% | 31.40% | 52.33% | 37.67% | 46.05% | 41.86% |
| Isopropyl myristate | Isopropyl myristate | 3.83% | 99.00% | 19.17% | 57.51% | 28.76% | 47.93% | 34.51% | 42.17% | 38.34% |
| Geraniol | Geraniol Fine FCC | 1.98% | 59.40% | 9.90% | 29.70% | 14.85% | 24.75% | 17.82% | 21.78% | 19.80% |
| Example 13 - Ingredient Family 13 | | | | | | | | | | |
| Linalool | Linalool Coeur | 2.34% | 70.14% | 11.69% | 35.07% | 17.54% | 29.23% | 21.04% | 25.72% | 23.38% |
| Amyl Butyrate | Amyl Butyrate | 2.35% | 70.38% | 11.73% | 35.19% | 17.60% | 29.33% | 21.11% | 25.81% | 23.46% |
| Anise Star Oil | Anise Star Oil | 5.32% | 99.00% | 26.58% | 79.74% | 39.87% | 66.45% | 47.84% | 58.48% | 53.16% |
| Example 14 - Ingredient Family 14 | | | | | | | | | | |
| Linalool | Linalool Coeur | 3.74% | 99.00% | 18.72% | 56.16% | 28.08% | 46.80% | 33.70% | 41.18% | 37.44% |
| Thymol | Thymol | 3.67% | 99.00% | 18.36% | 55.08% | 27.54% | 45.90% | 33.05% | 40.39% | 36.72% |
| Pinene | Alpha-pinene, 98% | 0.47% | 13.98% | 2.33% | 6.99% | 3.50% | 5.83% | 4.19% | 5.13% | 4.66% |
| Cymene | Para-Cymene | 0.19% | 5.61% | 0.94% | 2.81% | 1.40% | 2.34% | 1.68% | 2.06% | 1.87% |
| Anethole | Trans-Anethole | 1.93% | 57.93% | 9.66% | 28.97% | 14.48% | 24.14% | 17.38% | 21.24% | 19.31% |
| Example 15 - Ingredient Family 15 | | | | | | | | | | |
| Limonene | D-Limonene | 2.74% | 82.05% | 13.68% | 41.03% | 20.51% | 34.19% | 24.62% | 30.09% | 27.35% |
| Thyme Oil | Thyme Oil White | 3.01% | 90.24% | 15.04% | 45.12% | 22.56% | 37.60% | 27.07% | 33.09% | 30.08% |
| Lilac Flower Oil | Lilac Flower Oil | 4.26% | 99.00% | 21.30% | 63.90% | 31.95% | 53.25% | 38.34% | 46.86% | 42.57% |
| Example 16 - Ingredient Family 16 | | | | | | | | | | |
| Thyme Oil | Thyme Oil White | 3.82% | 99.00% | 19.11% | 57.32% | 28.66% | 47.76% | 34.39% | 42.03% | 38.21% |
| Wintergreen Oil | Wintergreen Oil | 2.48% | 74.37% | 12.40% | 37.19% | 18.59% | 30.99% | 22.31% | 27.27% | 24.79% |
| Isopropyl Myristate | Isopropyl Myristate | 3.59% | 99.00% | 17.95% | 53.84% | 26.92% | 44.86% | 32.30% | 39.48% | 35.89% |
| vanillin | Vanillin | 0.11% | 5.00% | 0.56% | 1.67% | 0.83% | 1.39% | 1.00% | 1.22% | 1.11% |
| Example 17 - Ingredient Family 17 | | | | | | | | | | |
| Wintergreen Oil | Wintergreen Oil | 2.48% | 74.46% | 12.41% | 37.23% | 18.62% | 31.03% | 22.34% | 27.30% | 24.82% |
| Isopropyl Myristate | Isopropyl Myristate | 3.59% | 99.00% | 17.97% | 53.91% | 26.96% | 44.93% | 32.35% | 39.53% | 35.94% |
| Thyme Oil | Thyme Oil White | 3.92% | 99.00% | 19.62% | 58.86% | 29.43% | 49.05% | 35.32% | 43.16% | 39.24% |
| Example 18 - Ingredient Family 18 | | | | | | | | | | |
| Thyme Oil | Thyme Oil White | 0.46% | 13.8% | 2.30% | 6.90% | 3.45% | 5.75% | 4.14% | 5.06% | 4.60% |
| Wintergreen Oil | Wintergreen Oil | 5.78% | 99.00% | 28.90% | 86.70% | 43.35% | 72.25% | 52.02% | 63.58% | 57.80% |
| Isopropyl Myristate | Isopropyl Myristate | 3.76% | 99.00% | 18.80% | 56.40% | 28.20% | 47.00% | 33.84% | 41.36% | 37.60% |

TABLE 2-continued

Exemplary Compositions

| Ingredients | Exemplified form | % Range 1 | | % Range 2 | | % Range 3 | | % Range 4 | | Exemplified % (w/w) |
|---|---|---|---|---|---|---|---|---|---|---|
| Example 19 - Ingredient Family 19 | | | | | | | | | | |
| Thyme Oil | Thyme Oil White | 3.16% | 94.71% | 15.79% | 47.36% | 23.68% | 39.46% | 28.41% | 34.73% | 31.57% |
| Isopropyl myristate | Isopropyl myristate | 3.86% | 99.00% | 19.28% | 57.84% | 28.92% | 48.20% | 34.70% | 42.42% | 38.56% |
| Wintergreen Oil | Wintergreen Oil | 2.99% | 89.61% | 14.94% | 44.81% | 22.40% | 37.34% | 26.88% | 32.86% | 29.87% |
| Example 20 - Ingredient Family 20 | | | | | | | | | | |
| Thyme Oil | Thyme Oil White | 2.06% | 61.80% | 10.30% | 30.90% | 15.45% | 25.75% | 18.54% | 22.66% | 20.60% |
| Isopropyl myristate | Isopropyl myristate | 3.43% | 99.00% | 17.15% | 51.45% | 25.73% | 42.88% | 30.87% | 37.73% | 34.30% |
| Geraniol | Geraniol Fine FCC | 4.51% | 99.00% | 22.55% | 67.65% | 33.83% | 56.38% | 40.59% | 49.61% | 45.10% |
| Example 21 - Ingredient Family 21 | | | | | | | | | | |
| Thyme Oil | Thyme Oil White | 1.24% | 37.14% | 6.19% | 18.57% | 9.29% | 15.48% | 11.14% | 13.62% | 12.38% |
| Wintergreen Oil | Wintergreen Oil | 3.13% | 93.96% | 15.66% | 46.98% | 23.49% | 39.15% | 28.19% | 34.45% | 31.32% |
| Limonene | D-Limonene | 5.63% | 99.00% | 28.15% | 84.45% | 42.23% | 70.38% | 50.67% | 61.93% | 56.30% |
| Example 22 - Ingredient Family 22 | | | | | | | | | | |
| LFO | LFO | 5.01% | 99.00% | 25.07% | 75.20% | 37.60% | 62.66% | 45.12% | 55.14% | 50.13% |
| BSO (Black Seed Oil) | BSO | 4.99% | 99.00% | 24.94% | 74.81% | 37.40% | 62.34% | 44.88% | 54.86% | 49.87% |
| Example 23 - Ingredient Family 23 | | | | | | | | | | |
| LFO | LFO | 8.01% | 99.00% | 40.05% | 99.00% | 60.07% | 99.00% | 72.08% | 88.10% | 80.09% |
| BSO (Black Seed Oil) | BSO | 1.99% | 59.73% | 9.96% | 29.87% | 14.93% | 24.89% | 17.92% | 21.90% | 19.91% |

In embodiments of the invention that include at least one blend of compounds of a plant origin, the compounds of plant origin can be tested for their precise chemical composition using, for example, High-Performance Liquid Chromatography (HPLC), Mass Spectrometry (MS), gas chromatography, or the like.

Other exemplary embodiments include the blends of compounds as set forth on pages 71-120 of WIPO Publication No. WO 2008/088827, published on Jul. 24, 2008.

The term "about" or "approximately" means within an acceptable error range for the particular value as determined by one of ordinary skill in the art, which will depend in part on how the value is measured or determined, i.e., the limitations of the measurement system, i.e., the degree of precision required for a particular purpose, such as a pharmaceutical formulation. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The term "substantially," as used herein, means at least about 80%, preferably at least about 90%, more preferably at least about 99%, for example at least about 99.9%. In some embodiments, the term "substantially" can mean completely, or about 100%.

Embodiments of the invention can include at least one oil, such as, for example, "Superior oil," highly-refined oils, and the like.

Synergistic Properties of Blends

Surprisingly, by blending certain compounds in certain relative amounts, the resulting composition demonstrates a repellant or pesticidal effect that exceeds the repellant or pesticidal effect of any component of the composition. As used herein, "component of a composition" refers to a compound, or a subset of compounds included in a composition, e.g., the complete composition minus at least one compound. As used herein, "repellant effect" is an effect wherein more insects are repelled away from a host or area that has been treated with the composition than a control host or area that has not been treated with the composition. In some embodiments, repellant effect is an effect wherein at least about 75% of insects are repelled away from a host or area that has been treated with the composition. In some embodiments, repellant effect is an effect wherein at least about 90% of insects are repelled away from a host or area that has been treated with the composition. As used herein, "pesticidal effect" is an effect wherein treatment with a composition causes at least about 1% of the insects to die. In this regard, when a first effect and a second effect are compared, the first effect can indicate a greater pesticidal or repellant efficacy if it exceeds the second effect. For example, when the effect being measured is a % killing of target insects, a greater % killing is a pesticidal effect that exceeds a lesser % killing. Effects that can be measured include, but are not limited to: time to kill a given percentage of a target insect, or repellency as to a given percentage of a target insect.

Surprisingly, by combining certain pest control chemicals, and compounds or blends of the present invention, pest control activity of the resulting compositions can be enhanced, i.e., a synergistic effect on pest control activity is achieved when a certain chemical or chemicals, and a certain compound or compounds are combined. In other words, the compositions including certain combinations of at least one chemical, and at least one compound or at least one blend of compounds can have an enhanced ability to control target pests, as compared to each of the chemicals or compounds taken alone.

In embodiments of the present invention, "synergy" can refer to any substantial enhancement, in a combination of at least two ingredients, of a measurable effect, when compared with the effect of one active ingredient alone, or when compared with the effect of the complete combination minus at least one ingredient. Synergy is a specific feature of a combination of ingredients, and is above any background level of enhancement that would be due solely to, e.g., additive effects of any random combination of ingredients. Effects include but are not limited to: repellant effect of the composition; pesticidal effect of the composition; perturbation of a cell message or cell signal such as, e.g., calcium, cyclic-AMP, and the like; and diminution of activity or downstream effects of a molecular target.

As used herein, "synergy" and "synergistic effect" can refer to any substantial enhancement, in a composition of at least two compounds, of a measurable effect, e.g., an antiparasitic effect, when compared with the effect of a component of the composition, e.g., one active compound alone, or the complete blend of compounds minus at least one compound. Synergy is a specific feature of a blend of compounds, and is above any background level of enhancement that would be due solely to, e.g., additive effects of any random combination of ingredients.

In some embodiments, a substantial enhancement of a measurable effect can be expressed as a coefficient of synergy. A coefficient of synergy is an expression of a comparison between measured effects of a composition and measured effects of a comparison composition. The comparison composition can be a component of the composition. In some embodiments, the synergy coefficient can be adjusted for differences in concentration of the complete blend and the comparison composition.

Synergy coefficients can be calculated as follows. An activity ratio (R) can be calculated by dividing the % effect of the composition (AB) by the % effect of the comparison composition ($X_n$), as follows:

$$R = A_B/X_n \qquad \text{(Formula 1)}$$

A concentration adjustment factor (F) can be calculated based on the concentration ($C_n$), i.e., % (wt/wt) or % (vol/vol), of the comparison composition in the composition, as follows:

$$F = 100/C_n \qquad \text{(Formula 2)}$$

The synergy coefficient (S) can then be calculated by multiplying the activity ratio (R) and the concentration adjustment factor (F), as follows:

$$S = (R)(F) \qquad \text{(Formula 3)}$$

As such, the synergy coefficient (S) can also by calculated, as follows:

$$S = [(AB/X_n)(100)]/C_n \qquad \text{(Formula 4)}$$

In Formula 4, AB is expressed as % effect of the blend, X, is expressed as % effect of the comparison composition ($X_n$), and $C_n$ is expressed as % (wt/wt) or % (vol/vol) concentration of the comparison composition in the blend.

In some embodiments, a coefficient of synergy of about 1.1, 1.2, 1.3, 1.4, or 1.5 can be substantial and commercially desirable. In other embodiments, the coefficient of synergy can be from about 1.6 to about 5, including but not limited to about 1.8, 2.0, 2.5, 3.0, 3.5, 4.0, and 4.5. In other embodiments, the coefficient of synergy can be from about 5 to 50, including but not limited to about 10, 15, 20, 25, 30, 35, 40, and 45. In other embodiments, the coefficient of synergy can be from about 50 to about 500, or more, including but not limited to about 50, 75, 100, 125, 150, 200, 250, 300, 350, 400, and 450. Any coefficient of synergy above 500 is also contemplated within embodiments of the compositions.

Given that a broad range of synergies can be found in various embodiments described herein, it is expressly noted that a coefficient of synergy can be described as being "greater than" a given number and therefore not necessarily limited to being within the bounds of a range having a lower and an upper numerical limit. Likewise, in some embodiments described herein, certain low synergy coefficients, or lower ends of ranges, are expressly excluded. Accordingly, in some embodiments, synergy can be expressed as being "greater than" a given number that constitutes a lower limit of synergy for such an embodiment. For example, in some embodiments, the synergy coefficient is equal to or greater than 25; in such an embodiment, all synergy coefficients below 25, even though substantial, are expressly excluded.

In some embodiments, synergy or synergistic effect associated with a composition can be determined using calculations similar to those described in Colby, S. R., "Calculating Synergistic and Antagonistic Responses of Herbicide Combinations," Weeds, 1967 15:1, pp. 20-22, which is incorporated herein by reference. In this regard, the following formula can be used to express percent effect (E) of a composition including two compounds, Compound X and Compound Y:

$$E = X + Y - (X*Y/100) \qquad \text{(Formula 5)}$$

In Formula 5, X is the measured actual percent effect of Compound X in the composition, and Y is the measured actual percent effect of Compound Y in the composition. The expected percent effect (E) of the composition is then compared to a measured actual percent effect (A) of the composition. If the actual percent effect (A) that is measured differs from the expected percent effect (E) as calculated by the formula, then the difference is due to an interaction of the compounds. Thus, the composition has synergy (a positive interaction of the compounds) when A>E. Further, there is a negative interaction (antagonism) when A<E.

Formula 5 can be extended to account for any number of compounds in a composition; however it becomes more complex as it is expanded, as is illustrated by the following formula for a composition including three compounds, Compound X, Compound Y, and Compound Z:

$$E = X + Y + Z - ((XY + XZ + YZ)/100) + (X*Y*Z/1000) \qquad \text{(Formula 6)}$$

An easy-to-use formula that accommodates compositions with any number of compounds can be provided by modifying Formulas 5 and 6. Such a modification of the formula will now be described. When using Formulas 5 and 6, an untreated control value (untreated with composition or compound) is set at 100%, e.g., if the effect being measured is the amount of target insects killed, the control value would be set at 100% survival of the target insect. In this regard, if treatment with compound A results in 80% killing of the target insect, then the treatment with compound A can be said to result in a 20% survival, or 20% of the control value. The relationship between values expressed as a percent effect and values expressed as a percent-of-control are set forth in the following formulas, where E' is the expected percent of control of the composition, $X_n$ is the measured actual % effect of an individual compound (Compound $X_n$) of the composition, $X_n'$ is the percent of control of an individual compound of the composition, and A' is the actual measured percent of control of the composition.

$$E = 100 - E' \quad \text{(Formula 7)}$$
$$X_n = 100 - X_n' \quad \text{(Formula 8)}$$
$$A = 100 - A' \quad \text{(Formula 9)}$$

By substituting the percent-of-control values for the percent effect values of Formulas 5 and 6, and making modifications to accommodate any number (n) of compounds, the following formula is provided for calculating the expected % of control (E') of the composition:

$$E' = \left(\prod_{i=1}^{n} X_i'\right) \div 100^{n-1} \quad \text{(Formula 10)}$$

According to Formula 10, the expected % of control (E') for the composition is calculated by dividing the product of the measured actual % of control values ($X_n'$) for each compound of the composition by $100^{n-1}$. The expected % of control (E') of the composition is then compared to the measured actual % of control (A') of the composition. If the actual % of control (A') that is measured differs from the expected % of control (E') as calculated by the Formula 10, then the difference is due to an interaction of the compounds. Thus, the composition has synergy (a positive interaction of the compounds) when A'<E'. Further, there is a negative interaction (antagonism) when A'>E'.

Compositions containing two or more compounds in certain ratios or relative amounts can be tested for a synergistic effect by comparing the pesticidal effect of a particular composition of compounds to the pesticidal effect of a component of the composition. Additional information related to making a synergy determination can be found in the examples set forth in this document. While synergy has been described in terms of a coefficient of synergy and in terms of the Colby synergy calculations, it is noted that synergy by other measures or determinations known in the art is, in some embodiments, also within the meaning of synergy as described and claimed herein.

Exemplary methods that can be used to determine the synergistic effect of a particular composition are set forth in the following applications, each of which is incorporated in its entirety herein by reference: U.S. application Ser. No. 10/832,022, entitled COMPOSITIONS AND METHODS FOR CONTROLLING INSECTS; U.S. application Ser. No. 11/086,615, entitled COMPOSITIONS AND METHODS FOR CONTROLLING INSECTS RELATED TO THE OCTOPAMINE RECEPTOR; U.S. application Ser. No. 11/365,426, entitled COMPOSITIONS AND METHODS FOR CONTROLLING INSECTS INVOLVING THE TYRAMINE RECEPTOR; and U.S. application Ser. No. 11/870,385, entitled COMPOSITIONS AND METHODS FOR CONTROLLING INSECTS.

Screening of Compositions

In some embodiments of the invention, the screening method for pest control potential can target a molecule of an insect olfactory receptor protein. In some embodiments of the invention, the screening method for pest control potential can target an insect olfactory receptor protein. The insect olfactory system includes more than 60 identified olfactory receptors. These receptors are generally members of a large family of G protein coupled receptors (GPCRs).

As used herein, a "receptor" is an entity on the cell membrane or within the cell, cytoplasm, or cell nucleus that can bind to a specific molecule (a ligand), such as, for example, a neurotransmitter, hormone, or the like, and initiates the cellular response to the ligand. Ligand-induced changes in the behavior of receptor proteins can result in physiological changes that constitute the biological actions of the ligands.

In accordance with the present disclosure, receptors such as G protein-coupled receptors may be classified on the basis of binding affinity of the receptor to an active ingredient. This may also be expressed as the binding affinity of the active ingredient for the receptor. The binding affinity of an active ingredient for a receptor, or the binding affinity of a receptor for an active ingredient, may be measured in accordance with methods disclosed herein or methods known to those of skill in the art. As used in the present disclosure, a "low" affinity indicates that a high concentration of the active ingredient relative to the receptor is required to maximally occupy the binding site of the receptor and trigger a physiological response, while a "high" affinity indicates that that a low concentration of the active ingredient relative to the receptor is adequate to maximally occupy the binding site of the receptor and trigger a physiological response. A "high" affinity may correspond to, for example, an active ingredient concentration of two or more orders of magnitude less than the concentration of the receptor that is effective to trigger the physiological response, while a "low" affinity may correspond to an active ingredient concentration of one or more orders of magnitude greater than the concentration of the receptor that is effective to trigger the physiological response.

Any insect cell or cell line can be used for the screening assay. Exemplary insect cell lines include but are not limited to SF9, SF21, T.ni, Drosophila S2 cells, and the like. Methods of culturing the insect cells are known in the art, and are described, for example, in Lynn et al., J. Insect Sci. 2002; 2: 9, incorporated herein by reference in its entirety. Methods of starting a new insect cell culture from a desired insect cell are described, for example, in Lynn et al. Cytotechnology. 1996; 20.3-1 1, which is incorporated herein by reference in its entirety.

Further discussion of various approaches to screening, preparing, evaluating, and using pest control formulations are disclosed in the following applications, each of which is incorporated by reference in its entirety: U.S. application Ser. No. 10/832,022, entitled COMPOSITIONS AND METHODS FOR CONTROLLING INSECTS; U.S. application Ser. No. 11/086,615, entitled COMPOSITIONS AND METHODS FOR CONTROLLING INSECTS RELATED TO THE OCTOPAMINE RECEPTOR; U.S. application Ser. No. 11/365,426, entitled COMPOSITIONS AND METHODS FOR CONTROLLING INSECTS INVOLVING THE TYRAMINE RECEPTOR; U.S. Provisional Application 60/807,600, entitled COMPOSITIONS AND METHODS FOR CONTROLLING INSECTS; U.S. Provisional Application 60/805,963, entitled COMPOSITIONS FOR TREATING PARASITIC INFECTIONS AND METHODS OF SCREENING FOR SAME; U.S. Provisional Application 60/718,570, entitled COMPOSITIONS HAVING INSECT CONTROL ACTIVITY AND METHODS FOR USE THEREOF.

In embodiments of the present invention, a Drosophila Schneider 2 (S2) cell line is stably transfected with a G protein-coupled receptor that is amplified from *Drosophila melanogaster* head cDNA phage library. The cell line can be used to screen potential active ingredients, as described below.

Receptor binding can result in cellular changes downstream to the receptor. The subsequent cellular changes may include altered intracellular cAMP levels, calcium levels or both.

In some embodiments of the invention, the screening method for pest control activity can target an insect olfactory receptor protein. The insect olfactory system includes more than 60 identified olfactory receptors. These receptors are generally members of a large family of G protein coupled receptors (GPCRs).

In *Drosophila melanogaster*, the olfactory receptors are located in two pairs of appendages located on the head of the fly. The family of Drosophila chemoreceptors includes approximately 62 odorant receptor (Or) and 68 gustatory receptor (Gr) proteins, encoded by families of approximately 60 Or and 60 Gr genes through alternative splicing. Some of these receptor proteins have been functionally characterized, while others have been identified by sequence homology to other sequences but have not been fully characterized. Other insects have similar olfactory receptor proteins.

In some embodiments, the insect olfactory receptor protein targeted by the screening or pest control method of the invention is the tyramine receptor (tyrR). In additional embodiments, the insect olfactory receptor protein is the insect olfactory receptor protein Or83b or Or43a. For example, the receptor can be any of the tyramine (TyrR), Or83b, or Or43a receptors referenced as SEQ ID NOs. 1-6 on pages 20-26 of U.S. Patent Publication No. 2005-0008714, published Jan. 13, 2005 and entitled COMPOSITIONS AND METHODS FOR CONTROLLING INSECTS. In additional embodiments, the targeted protein can be any of the insect olfactory protein receptors.

Additionally, other components of the insect olfactory receptor cascade can be targeted using the method of the invention in order to identify useful pest control compounds. Exemplary insect olfactory cascade components that can be targeted by methods of the invention include but are not limited to serotonin receptor, Or22a, Or22b, Gr5a, Gr21a, Gr61a, beta-arrestin receptor, GRK2 receptor, and tyramine beta-hydroxylase receptor, and the like.

Figure 22:
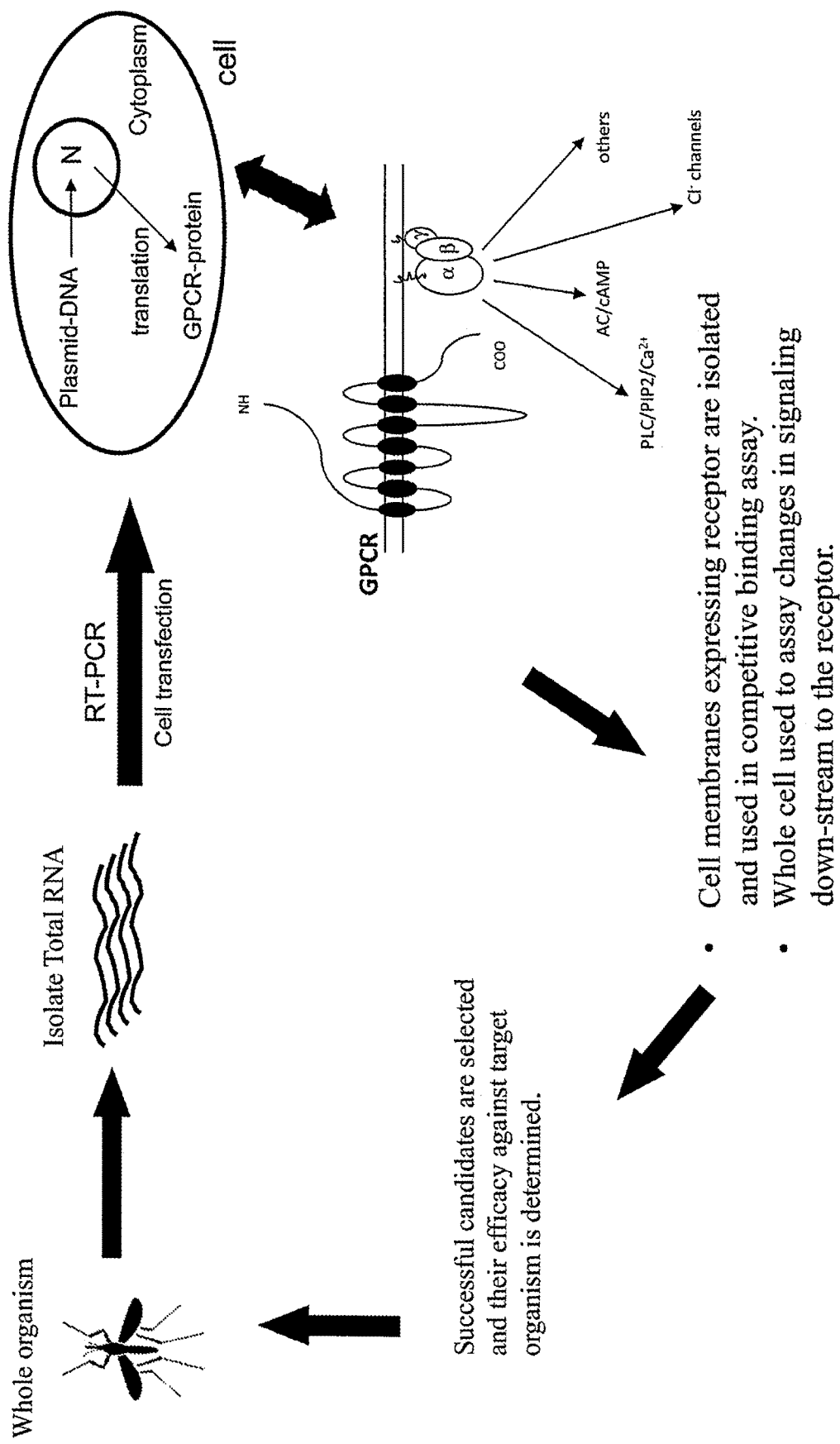
FIG. 22 is a schematic illustrating an embodiment of a screening method using a transfected cell line expressing a receptor of interest.
Figure 23:
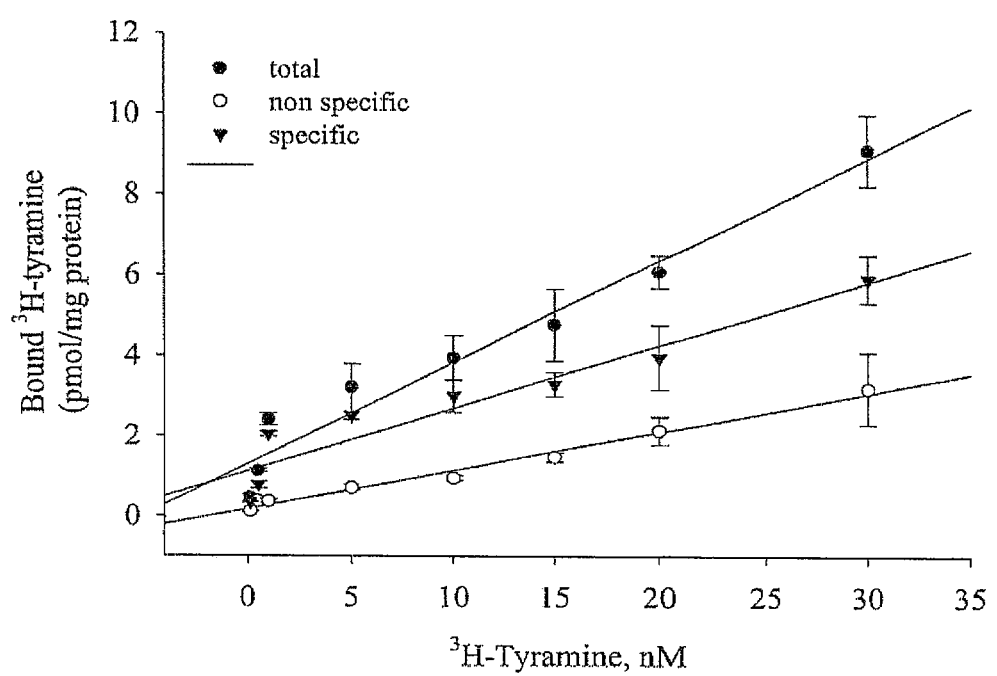
FIG. 23 is a graph illustrating a saturation binding curve of $^3$H-tyramine to the membrane fractions of S2 cells expressing a tyramine receptor ("Tyr$^R$").

With reference to FIG. 22, an exemplary screening method for identifying effective pestcontrol compositions can make use of one or more transfected cell lines expressing a receptor of interest, for example, a biogenic amine receptor, such as, a TyR or an octopamine receptor.

In some embodiments of the invention, isolated cell membranes expressing the receptor of interest can be used in competitive binding assays. Whole cells can be used to study changes in signaling down-stream to the receptor, in response to treatment with a test composition.

Embodiments of the invention can utilize prokaryotic and eukaryotic cells including, for example, bacterial cells, yeast cells, fungal cells, insect cells, nematode cells, plant cells, animal cells, and the like. Suitable animal cells can include, for example, HEK cells, HeLa cells, COS cells, U2OS cells, CHO-K1 cells, various primary mammalian cells, and the like. An animal model expressing one or more conjugates of an arrestin and a marker molecule, for example, throughout its tissues, within a particular organ or tissue type, or the like, can be used.

The potential for pest control activity can be identified by measuring the affinity of the test compositions for the receptor in the cell lines expressing a TyrR, Or83b, and/or Or43a. The potential for pest control activity can also be identified by measuring the change in intracellular cAMP and/or Ca2+ in the cell lines expressing TyrR, Or83b, and/or Or43a following treatment with the test compositions. The gene sequences of the TyrR, the Or83b receptor and the Or43a receptor have substantial similarity between various insect species. As such, the Drosophila Schneider cell lines expressing these receptors can be used to screen for compositions having pest control activity in various insect species.

Targeted Pests

The methods of embodiments of the invention can used to control any type of target pest.

In some embodiments, the target pest is an insect. Exemplary insects that can be controlled include but are not limited to beetles, cockroaches, flies, ants, insect larvae, bees, lice, fleas, mosquitoes, moths, and the like. Exemplary insect orders can include but are not limited to orders Acari, Anoplura, Araneae, Blattodea, Coleoptera, Collembola, Diptera, Grylloptera, Heteroptera, Homoptera, Hymenoptera, Isopoda, Isoptera, Lepidoptera, Mantodea, Mallophaga, Neuroptera, Odonata, Orthoptera, Psocoptera, Siphonaptera, Symphyla, Thysanura, and Thysanoptera and the like. Embodiments of the invention can also be used to control, for example, the insects set forth in Table 5 on pages 123-195 of WIPO Publication No. WO 2008/088827 (a publication of PCT Application Serial No. PCT/US2008/000573, entitled PEST CONTROL COMPOSITIONS AND METHODS, published on Jul. 24, 2008).

In some embodiments, the target pest is a parasite. Exemplary parasites include, but are not limited to, protozoa (including intestinal protozoa, tissue protozoa, and blood protozoa), helminthes and parasitic worms, including nematodes (roundworms) and platyhelminthes (flatworms). Examples of intestinal protozoa include, but are not limited to: *Entaroeba hystolytica, Giardia lamblia, Cryptosporidium muris*, and *Cryptosporidium parvum*. Examples of tissue protozoa include, but are not limited to: *Trypanosomatida gambiense, Trypmosomatida rhodesiense, Tryxmosomatida crusi, Leishmania mexicana, Leishmania braziliensis, Leishmania tropica, Leishmania donovani, Toxoplasma gondii*, and *Trichomonas vaginalis*. Examples of blood protozoa include, but are not limited to *Plasmodium vivax, Plasmodium ovale, Plasmodium malariae*, and *Plasmodium falciparum*. *Histomonas meleagridis* is yet another example of a protozoan parasite. Examples of nematodes include, but are not limited to: animal and plant nematodes of the adenophorea class, such as the intestinal nematode *Trichuris trichiura* (whipworm) and the plant nematode *Trichodorus obtusus* (stubby-root nematode); intestinal nematodes of the secementea class, such as *Ascaris lumbricoides, Enterobius vermicularis* (pinworm), *Ancylostora duodenale* (hookworm), *Necator americanus* (hookworm), and *Strongyloides stercoralis*; tissue nematodes of the secementea class, such as *Wuchereria bancrofti* (*Filaria bancrofti*) and *Dracunculus medinensis* (Guinea worm); *Ascaris suum*; and *Toxocara canis*. Examples of plathyeminthes include, but are not limited to: Trematodes (flukes), including blood flukes, such as *Schistosoma mansoni* (intestinal Schistosomiasis), *Schistosoma haematobium*, and *Schisto-*

*soma japonicum*; liver flukes, such as *Fasciola hepatica*, and *Fasciola gigantica*: intestinal flukes, such as *Heterophyes heterophyes*; and lung flukes such as *Paragonimus westermani*. Examples of plathemintes further include, but are not limited to: Cestodes (tapeworms), including *Taenia solium, Trenia saginata, Hymenolepsis nana*, and *Echinococcus granulosus*. Parasites also include ectoparasites, such as, for example, roundworms, worms, ticks, fleas, lice and other organisms found on an external orifice or found on or in a skin surface. Exemplary ectoparasites include, but are not limited to, *Ctenocephalides felis, Dermacentor andersoni, Rhipicephalus sanguineus, Aedes aegypti, Stomoxys calcitrans*, and the like. Embodiments of the invention can also be used to control, for example, the parasites set forth on pages 196-205 (including Table 6) of WIPO Publication No. WO 2008/088827, published on Jul. 24, 2008, or the like.

Embodiments of the invention can also be used to prevent or treat parasitic disease inflicted upon the parasite hosts set forth in Table 7 on pages 205-232 of W IPO Publication No. WO 2008/088827, published on Jul. 24, 2008, or the like.

Embodiments of the invention can be used to treat crops in order to limit or prevent pest infestation. The crops that can be treated by the compositions and methods disclosed herein include, but are not limited to, the crops set forth in Table 8 on pages 232-239 of WIPO Publication No. WO 2008/008827, published on Jul. 24, 2008, or the like.

Modes of Administration or Dispensation

In the case of an animal, human or non-human, the host can also be treated directly by using a formulation of a composition that is delivered orally. For example, a composition can be enclosed within a liquid capsule and ingested.

An area can be treated with a composition of the present invention, for example, by using a spray formulation, such as an aerosol or a pump spray, or a burning formulation, such as a candle or a piece of incense containing the composition. Of course, various treatment methods can be used without departing from the spirit and scope of the present invention. For example, compositions can be comprised in household products such as: air fresheners (including heated air fresheners in which insect repellent substances are released upon heating, e.g., electrically, or by burning); hard surface cleaners; or laundry products (e.g., laundry detergent-containing compositions, conditioners). In some embodiments of the invention, an area can be treated, for example, via aerial delivery, by truck-mounted equipment, or the like.

An exemplary dispenser of a system of the present invention can deliver a pest control composition to the atmosphere in a continuous manner over a period of time. The exemplary dispenser can include a reservoir for holding a pest control composition, and a wick for drawing the composition from the reservoir and releasing the pest control composition into the atmosphere. The reservoir can be constructed from a material that is impermeable to the pest control composition, for example, appropriate glass, ceramic, or polymeric materials can be used. The reservoir can include an aperture, which can be sealed or unsealed, as desired. When the exemplary system of the present invention is not in use, the aperture can be sealed to prevent the release of the pest control composition into the atmosphere. It may be desirable, for example, to seal the aperture when the exemplary system is being stored or transported. When the system is in use, the aperture is unsealed, such that the wick can draw the pest control composition from the reservoir, and release the control composition through the aperture into the atmosphere.

In some embodiments, the rate of release of the composition can be controlled, for example, by making adjustments to the wick of the dispenser. For example, the surface area of the wick that is exposed to the atmosphere can be altered. Generally, the greater the exposed surface area, the greater the rate of release of the pest control composition. In this regard, in some embodiments, the dispenser can include multiple wicks and the reservoir can include multiple apertures through which the pest control composition can be released into the atmosphere. As another example, the wick can be constructed from a particular material that draws the pest control composition from the reservoir and releases it into the environment at a desired rate, such as, for example, a wick made of wood, a wick made of a synthetic fiber, or the like.

Another exemplary dispenser of a system of the present invention can deliver a pest control composition to a desired area. The dispenser can include a sealed pouch that can be constructed from a material that is impermeable to the pest control composition, for example, a metallic foil, a polymeric material, or the like. The pouch can define a volume for holding the pest control composition. The composition can be provided in a material disposed within the volume of the pouch, for example, a sponge, a cloth saturated with the material, or the like. When it becomes desirable to place the exemplary system into use, the pouch can be unsealed, exposing the composition for release into the atmosphere or for application to a desired area.

In some embodiments, the pest control composition is provided in a saturated cloth within the pouch, which can be used to apply the control composition a desired area. For example, a desired area can be an animal, such as a human, a domestic animal, surfaces within a dwelling, an outdoor living area, or the like.

In some embodiments, the dispenser can further include a hook, allowing the pouch and exposed control composition to be hung in a desired location, such as in a closet or a pantry.

In some embodiments, a method of the present invention can deliver insect a control composition to a desired area. In some embodiments, a dispenser used with the method can be constructed from a substantially planar, integral piece of material, having a first side that is coated with control composition, and a second side that is not coated with control composition. The integral piece of material can be folded and sealed such that the side coated with the control composition is contained within the volume defined by the sealed pouch. When the pouch is unsealed, the side that is coated with control composition is exposed. The substantially planar piece of material can be placed in a desired location to deliver control composition to the atmosphere, or to crawling insects that walk across the material.

Another exemplary dispenser of a system of the present invention can deliver a pest control composition to a desired area. The control composition can be incorporated into an appropriate material. In some embodiments, the composition-containing material can be a material that is capable of controlling the release rate of the control composition, i.e., controlled-release material, allowing the control composition to be released into the atmosphere at a desired rate that can be adjusted by providing controlled-release material having appropriate specifications. The controlled-release material can be constructed from an appropriate polymer. In other embodiments the composition-containing material does not allow the control composition to be released into the atmosphere, but rather retains the control composition. An optional casing that is impermeable to the pest control composition can be provided to hold the composition-containing material until the system is ready for use. When the system is ready for use, the casing can be peeled away, exposing the composition-containing material. The composition-containing material can be placed in a desired location to deliver control composition to crawling insects that walk across the material, or to deliver the control composition to the atmosphere when a controlled-release material is used, e.g., control flying insects.

In some embodiments, the composition-containing material can have a substantially planar design, appropriate for positioning adjacent a mattress for controlling bed bugs, e.g., *Cimex lectularius*. A substantially planar design can also be used, for example, as or with a picnic table cloth. In some embodiments, the composition-containing material can be used as ground cover for a garden bed or adjacent crop plants to control weeds. In some embodiments, the composition-containing material can take the shape of a bag, and could be used for trash collection, while controlling insect commonly attracted to household garbage or other trash.

Another exemplary dispenser of a system of the present invention can be a substantially dry sheet containing the control composition, which control composition can be applied to a desired location upon exposing the cloth to water or an aqueous liquid, e.g., perspiration. In some embodiments, the dry sheet containing the control composition can dissolve into a cream or gel when exposed to water or an aqueous liquid, which can then be applied to a desired area. For example, a desired area can be an animal, such as a human, a domestic animal, or another animal.

Identification of Components for Making an Improved Pest Control Agent

Embodiments of the invention are also directed to making an improved pest control agent by identifying one or more fractions in a complex agent, screening the one or more fractions using the methods disclosed herein, and characterizing the one or more fractions as having a positive or negative effect on potential activity against a target pest.

In some embodiments, one or more fractions in a complex agent (such as, for example, an essential oil) can be isolated using fractionation techniques including, for example, differential solvent extraction, fractional distillation, fractional crystallization, fractional freezing, dry fractionation, detergent fractionation, solvent extraction, supercritical $CO_2$ fractionation, vacuum distillation, column chromatography, reverse-phase chromatography, high-pressure liquid chromatography, and the like. These methods are known to those of skill in the art. Vacuum distillation is preferred, because it is relatively simple to employ and does not require the use of solvents.

In some embodiments, one or more fractions of a complex agent can be isolated by column chromatography using silica or alumina solid support. An organic solvent, including for example, alkanes such as hexanes and petroleum ether, toluene, methylene chloride (or other halogenated hydrocarbons), diethyl ether, ethyl acetate, acetone, alcohol, acetic acid, and the like, can be used alone or in combination as the column solvent, or mobile phase. In some embodiments, the complex agent is fractionated by column chromatography using an increasing concentration of a polar solvent as eluting solvent. Methods of column chromatography and solvents common for its use are well known in the art.

In some embodiments, a complex agent, such as a plant essential oil, can be isolated by solvent extraction. For example, an essential oil can be combined with an organic solvent, including, for example an organic solvent such as acetic acid, acetone, acetonitrile, benzene, 1-butanol, 2-butanol, 2-butanone, t-butyl alcohol, carbon tetrachloride, chlorobenzene, chloroform, cyclohexane, 1,2-dichloroethane, diethyl ether, diethylene glycol, diglyme (diethylene glycol dimethyl ether), 1,2-dimethoxy-ethane (glyme, DME), dimethylether, dimethyl-formamide (DMF), dimethyl sulfoxide (DMSO), dioxane, ethanol, ethyl acetate, ethylene glycol, glycerin, heptane, hexamethylphosphoramide (HMPA), hexamethylphosphorous triamide (HMPT), hexane, methanol, methyl t-butyl ether (MTBE), methylene chloride, N-methyl-2-pyrrolidinone (NMP), nitromethane, pentane, petroleum ether (ligroine), 1-propanol, 2-propanol, pyridine, tetrahydrofuran (THF), toluene, triethyl amine, water, heavy water, o-xylene, m-xylene, and p-xylene. Other organic solvents known to those of skill in the art can also be employed. The mixture of the essential oil and the organic solvent can then be combined with an extraction solvent that is not miscible in the organic solvent, including, for example, water, ethanol, and methanol. This combination is shaken vigorously in a glass container such as a separatory funnel for several minutes, then allowed to settle into separate phases for several minutes. The lower, more dense phase is then allowed to drain from the separatory funnel. The organic phase can then be repeatedly reextracted with the extraction solvent to further partition compounds that are soluble in the extraction solvent from the organic phase. The volume of the organic phase and the extracted phase can then be reduced in volume using rotary evaporation, yielding two separate fractions of the plant essential oil.

In some embodiments, a method of making an improved agent against a target pest can include the following: a fraction of a complex agent with activity against a target pest is isolated. This fraction is recombined with proportionally smaller volumes of the remaining fractions of the complex agent, such that the components of the fraction are enriched in the recombined complex agent relative to the unfractionated complex agent. A cell expressing Drosophila TyrR is provided and is contacted with the recombined complex agent. At least one parameter selected from the following parameters is measured: competitive inhibition of tyramine binding by TyrR, intracellular cAMP level, and intracellular $Ca^{2+}$ level. In parallel, the same parameter is measured in cells contacted with a volume of the unfractionated complex agent that is equivalent to the test volume of the recombined complex agent. The magnitude of the specific parameter measured in the cells contacted with the recombined complex agent is compared with the magnitude of the parameter measured in parallel cells contacted with the unfractionated complex agent. If the magnitude of this parameter is higher for the recombined agent, the comparison indicates that one or more active ingredients with an ability to modulate the activity of the tyramine receptor are enriched in the recombined agent with respect to the concentration of the active ingredients in the unfractionated agent. Thus this comparison identifies the recombined agent as an improved agent against a target pest. If the magnitude of this parameter is lower for the recombined agent, the comparison indicates that one or more active ingredients with an ability to modulate the activity of the tyramine receptor are diluted in the recombined agent with respect to the concentration of the active ingredients in the unfractionated agent. In this case, the comparison indicates that the recombination of the isolated fraction with proportionally larger, rather than smaller, volumes of the remaining fractions generates an improved agent against a target pest.

Thus, in some embodiments, a method of identifying an improved agent against a target pest can include the isolation of a fraction of a complex agent followed by recombination of this fraction with proportionally larger volumes of the remaining fractions, such that the components of the fraction are diluted in the recombined complex agent relative to the unfractionated complex agent. A cell expressing Drosophila TyrR is provided and is contacted with the recombined complex agent. At least one parameter selected from the following parameters is measured: competitive inhibition of tyramine binding by TyrR, intracellular cAMP level, and intracellular $Ca^{2+}$ level. In parallel, the same parameter is measured in cells contacted with a volume of the unfractionated complex agent that is equivalent to the test volume of the recombined complex agent. The magnitude of the specific parameter measured in the cells contacted with the recombined complex agent is compared with the magnitude of the parameter measured in parallel cells contacted with the unfractionated complex agent. If the magnitude of the parameter is higher for the recombined agent, the comparison indicates that one or more active ingredients with an ability to modulate the activity of the tyramine receptor are enriched in the recombined agent with respect to the concentration of the active ingredients in the unfractionated agent. In this case, an improved agent against a target pest is generated by reducing the relative abundance of the isolated fraction.

In some embodiments, a method for identifying an improved agent against a target pest can include the identification of the compounds present in either a complex agent or individual isolated fractions of a complex agent and screening of the ingredient compounds for their ability to bind or mediate the activity of an insect olfactory receptor. Identification of the compounds can be performed by analyzing the complex agent or an isolated fraction thereof by High-Performance Liquid Chromatography (HPLC) or gas chromatography (GC) coupled with Mass Spectrometry (MS). Ingredient compounds can also be identified by first enriching or purifying individual ingredients to homogeneity using techniques including, for example, differential solvent extraction, fractional distillation, vacuum distillation, fractional crystallization, fractional freezing, dry fractionation, detergent fractionation, solvent extraction, supercritical $CO_2$ fractionation, column chromatography, reverse-phase chromatography, high-pressure liquid chromatography, and the like. Enriched or purified components can be identified using spectroscopy techniques, including, for example, infrared (IR) spectroscopy, Raman spectroscopy, nuclear magnetic resonance spectroscopy (NMR), and the like.

Some embodiments relate to the use of chemical derivatives or analogs of chemicals identified in plant essential oils to generate an improved agent against a target pest. Chemical derivatives of the chemicals identified in plant essential oils can include compounds derivatized with an inorganic or organic functional group. In some embodiments, the chemical derivative is a compound derivatized with an organic functional group. In some embodiments, the organic functional group can be an alkyl group. In some embodiments, the organic functional group can be a methyl, ethyl, propyl, butyl, ceryl, decyl, heptyl, hexyl, myricyl, myristyl, nonyl, octyl, palmityl, pentyl, stearyl, isopropyl, isobutyl, lignoceryl, pentacosyl, heptacosyl, montanyl, nonacosyl, pentan-2-yl, isopentyl, 3-methylbutan-2-yl, tert-pentyl, neopentyl, undecyl, tridecyl, pentadecyl, margaryl, nonadecyl, arachidyl, henicosyl, behenyl, tricosyl, cyclobutyl, cyclopropyl group, or the like. In some embodiments, the organic functional group can be an aryl group. In some embodiments, the organic functional group can be a phenyl or biphenyl-4-yl group.

In some embodiments, the improved agent against a target pest includes a chemical derivative that is a halogenated derivative of a compound identified in a plant essential oil. In some embodiments, the chemical derivative is a fluorinated, chlorinated, brominated, or iodinated derivative.

In some embodiments, the improved agent against a target pest includes a chemical derivative that is an alkenylated derivative of a compound identified in a plant essential oil. In some embodiments, the chemical derivative is an oleylated, allylated, isopropenylated, vinylated, prenylated, or phytylated derivative.

In some embodiments, the improved agent against a target pest includes a chemical derivative that is a hydroxylated derivative of a compound identified in a plant essential oil.

In some embodiments, the improved agent against a target pest includes a chemical derivative that is a thiolated derivative of a compound identified in a plant essential oil.

In some embodiments, the improved agent against a target pest includes a chemical derivative that is a carboxylated derivative of a compound identified in a plant essential oil.

In some embodiments, the improved agent against a target pest includes a chemical derivative that is an amidated derivative of a compound identified in a plant essential oil.

In some embodiments, the improved agent against a target pest includes a chemical derivative that is an esterified derivative of a compound identified in a plant essential oil.

In some embodiments, the improved agent against a target pest includes a chemical derivative that is acylated derivative of a compound identified in a plant essential oil.

In some embodiments, the improved agent against a target pest includes a chemical derivative that is a sulfonated derivative of a compound identified in a plant essential oil.

In some embodiments, the improved agent against a target pest includes a chemical analogue of a compound identified in a plant essential oil. A chemical analogue can be identified using readily available chemical databases such as ChemBioFiner.com (copyright 2008 CambridgeSoft Corporation).

Compounds identified as ingredients of a plant essential oil, or chemical derivative thereof, can be obtained by commercial suppliers, including, for example Sigma Aldrich, Fluka, Fisher, Novabiochem, TCI America, Acros, Lancaster, and Alfa Aesar.

Compounds can then be screened for activity against a target pest by using the methods disclosed herein. For example, a compound can be screened for activity against a target pest by contacting a cell expressing an olfactory receptor with the compound and measuring a parameter such as competitive inhibition of a receptor-ligand binding interaction, intracellular cAMP level, and intracellular $Ca^{2+}$ level, as described in the screening methods disclosed herein. In some embodiments, competitive inhibition of tyramine binding by the Drosophila tyramine receptor (TyrR) is measured. In some embodiments, allosteric binding to target receptors can be measured. In some embodiments, screening of compounds can be performed in a high-throughput manner by assaying cells cultured in microtiter plates, such as 386-well or 96-well plates. Methods of screening are well known in the art.

In some embodiments of the invention, the cell used to determine the activity of a compound related to target pest control can be any cell capable of being transfected with and express an insect olfactory receptor, including, for example, TyrR, Or83b, Or43a, and the like. Examples of cells include, but are not limited to: insect cells, such as Drosophila Schneider cells, Drosophila Schneider 2 cells (S2 cells), and *Spodoptera frugiperda* cells (e.g., Sf9 or Sf21); or mammalian cells, such as Human Embryonic Kidney cells (HEK-293 cells), African green monkey kidney fibroblast cells (COS-7 cells), HeLa Cells, and Human Keratinocyte cells (HaCaT cells).

The TyrR can be a full-length TyrR, a functional fragment of a TyrR, or a functional variant of a TyrR. A functional fragment of a TyrR is a TyrR in which amino acid residues are deleted as compared to the reference polypeptide, i.e., full-length TyrR, but where the remaining amino acid sequence retains the binding affinity of the reference polypeptide for tyramine. A functional variant of a TyrR is a TyrR with amino acid insertions, amino acid deletions, or conservative amino acid substitutions, that retains the binding affinity of the reference polypeptide for tyramine. A "conservative amino acid substitution" is a substitution of an amino acid residue with a functionally similar residue. Examples of conservative substitutions can include, for example, the substitution of one non-polar (hydrophobic) residue such as isoleucine, valine, leucine or methionine for another; the substitution of one polar (hydrophilic) residue for another such as between arginine and lysine, between glutamine and asparagine, between glycine and serine; the substitution of one basic residue such as lysine, arginine or histidine for another; the substitution of one acidic residue, such as aspartic acid or glutamic acid for another, and the like. A conservative amino acid substitution can also include replacing a residue with a chemically derivatized residue, provided that the resulting polypeptide retains the binding affinity of the reference polypeptide for tyramine. Examples of TyrRs can include, for example: TyrRs, such as, *Drosophila melanogaster* TyrR (GENBANK®) accession number (GAN) CAA38565), *Locusta migratoria* TyrR (GAN: Q25321), TyrRs of other invertebrates, TyrRs of nematodes, and the like.

Exemplary screening methods can include "positive" screening, where, for example, compositions that bind a receptor of interest are selected. Exemplary screening methods can include "negative" screening, where, for example, compositions that bind a receptor of interest are rejected. An exemplary method can include: selecting a composition that binds a TyrR. Another exemplary method can include: selecting a composition that binds a TyrR and does not bind an octopamine receptor.

In some embodiments of the invention, the efficacy of a test composition can be determined by conducting studies with insects. For example, the efficacy of a test composition for repelling an insect can be studied using controlled experiments wherein insects are exposed to the test composition. In some embodiments, the toxicity of a test composition against an insect can be studied using controlled experiments wherein insects are exposed to the test composition.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

In Vitro Synergistic Response to a Blend Containing Natural Ingredients

A blend of oils, denoted as Blend 27 (also referred to in the figures as "B7001" or "Armor Lead Blend"), was prepared and set aside. The composition of this blend in weight percent format is provided below:

TABLE A

| Blend 27 from Oils | | |
|---|---|---|
| CAS | Description | Wt/wt |
| 80-56-8 | Alpha-Pinene, 98% | 3.78% |
| 78-70-6 | Linalool Coeur | 6.63% |
|  | Canola Oil | 24.0% |
| 99-87-6 | Para-Cymene | 28.39% |
| 89-83-8 | Thymol | 37.17% | where soy bean oil (CAS 8016-70-4) can also be substituted for canola oil.

The blend (at a final concentration of 0.5 mg/mL) was tested on a Drosophila Scheider 2 ("S2") cell line that was stably transfected with a DNA encoding a tyramine receptor that was amplified from a *Drosophila melanogaster* head cDNA phage library ("droTyrR"). The intracellular calcium levels ("$[Ca^{2+}]_i$") in the treated S2 cells were then measured as a function of time. As a comparison, the a solution of carrier (canola oil, final concentration=0.12 mg/mL) and a solution of surfactant (sugar ester OWA-1570) in insect saline were tested separately. The results indicated that treatment with Blend 27 resulted in a synergistic increase in $Ca^{2+}$ release triggered by olfactory receptor activation in Drosophila S2 cells in comparison to carrier alone and surfactant alone (FIG. 1).

Figure 2:
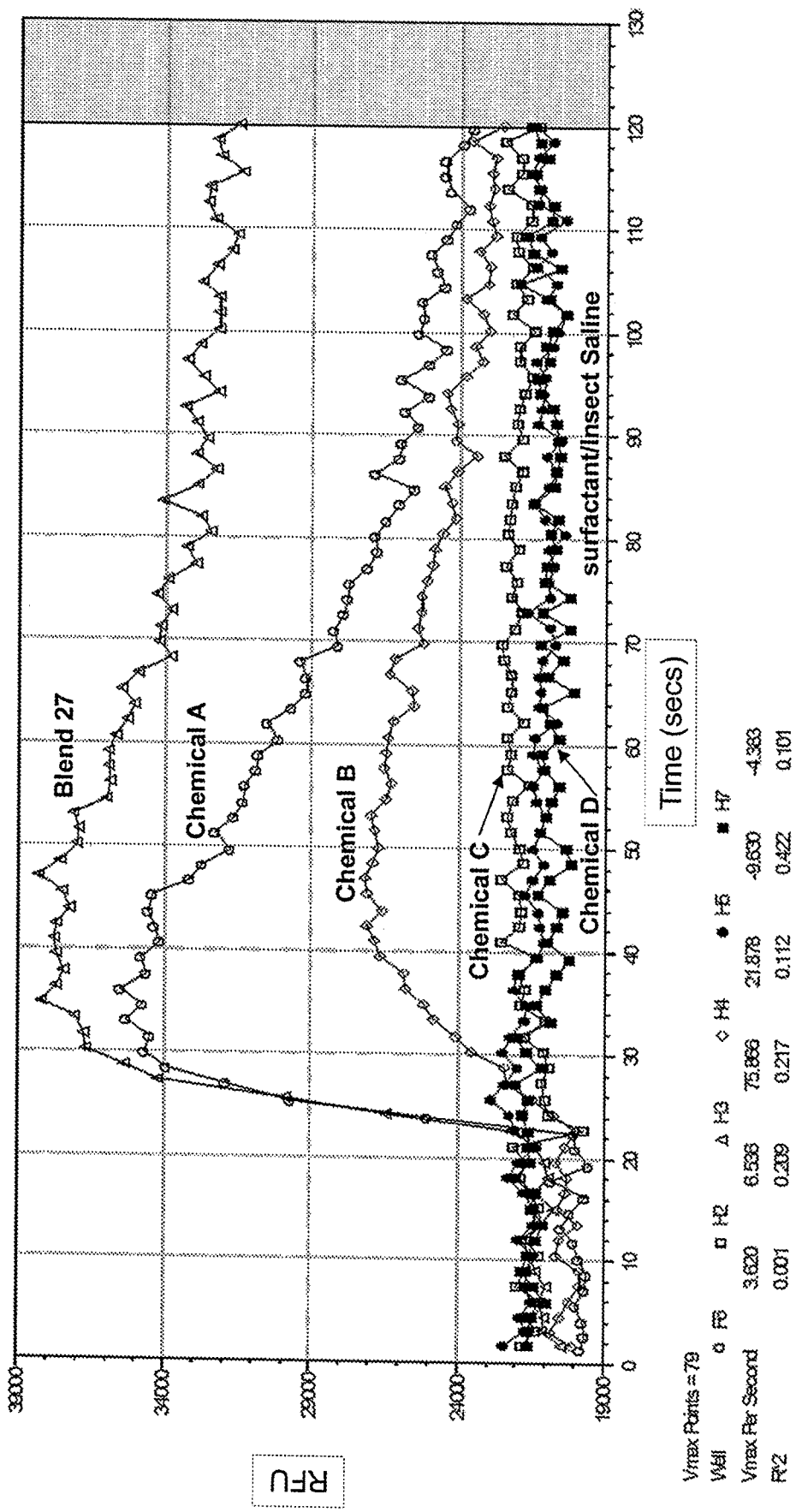

In a separate set of experiments, the blend (at a final concentration of 0.5 mg/mL) was tested on a Drosophila Scheider 2 ("S2") cell line that was stably transfected with droTyrR DNA, and the intracellular calcium levels ("$[Ca^{2+}]_i$") in the treated S2 cells were then measured as a function of time. As a comparison, the individual ingredients of the blend (A=thymol, B=para-cymene, C=linalool coeur, D=alpha-pinene (or "a-pinene")), were each tested separately on the cells at the same final concentration as that of the blend. In addition, a solution of surfactant (sugar ester OWA-1570) in insect saline was tested separately. The results indicated that treatment with Blend 27 resulted in a synergistic increase in $Ca^{2+}$ release triggered by olfactory receptor activation in Drosophila S2 cells in comparison to that caused by administration of the individual ingredients or of the surfactant alone (FIG. 2).

Figure 3:
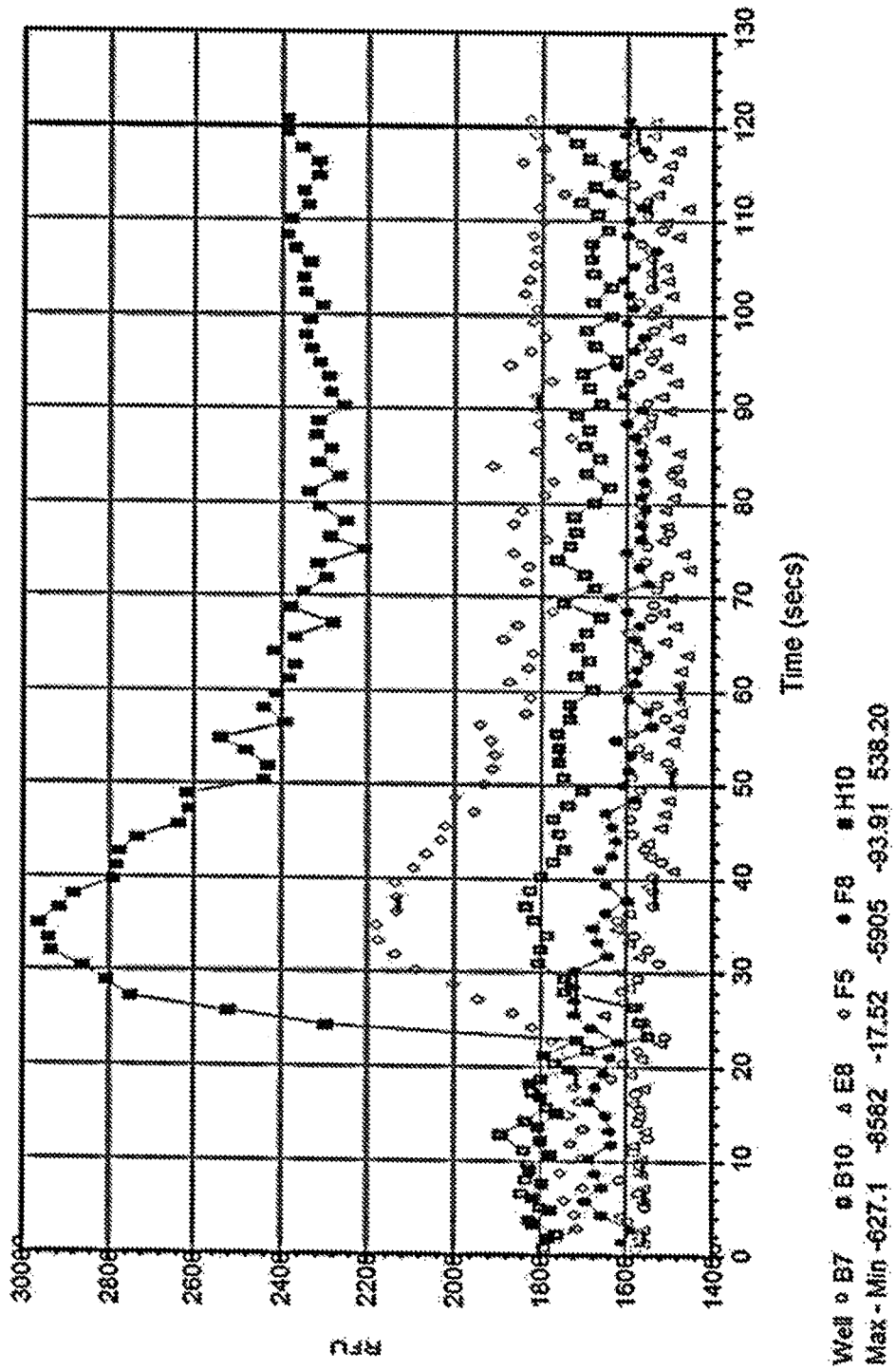

In yet another separate set of experiments, the blend (at a final concentration of 0.5 mg/mL) was tested on a Drosophila Scheider 2 ("S2") cell line that was stably transfected with droTyrR DNA, and the intracellular calcium levels ("$[Ca^{2+}]_i$") in the treated S2 cells were then measured as a function of time. As a comparison, the individual ingredients of the blend (A=thymol, B=para-cymene, C=linalool coeur, D=alpha-pinene (or "a-pinene")), were each tested separately on the cells at final concentrations that reflected the % (v/v) in which they are found in the blend. In addition, a solution of surfactant (sugar ester OWA-1570) in insect saline was tested separately. The results indicated that treatment with Blend 27 resulted in a synergistic increase in $Ca^{2+}$ release triggered by olfactory receptor activation in Drosophila S2 cells in comparison to that caused by administration of the individual ingredients or of the surfactant alone (FIG. 3).

Example 2

Synergistic Response to a Blend Containing Natural Ingredients on *Ascaris suum*

Blend 27 (also referred to in the figures as "B7001" or "Armor Lead Blend") was prepared and set aside as described (Example 1). The blend, as well as solutions containing individual ingredients (A=thymol, B=para-cymene, C=linalool coeur, D=alpha-pinene (or "a-pinene"), carrier=canola oil) that make up the blend, were administered to the endoparasite *Ascaris suum* in RPMI 1640 culture media containing antibiotics and antimycotic agents (10 worms per test). The final concentration of the blend tested was 10 µg/mL, while the final concentrations of the individual ingredients reflected the % (v/v) in which they are found in the blend. As a control, a solution of surfactant (sugar ester OWA-1570) was tested separately. The results indicated that treatment with Blend 27 resulted in a synergistic effect on the mortality of the endoparasites compared to that observed with administration of the individual ingredients or carrier alone (FIG. 4).

Example 3

Synergistic Response to Blends Containing Natural Ingredients on Various Endoparasites Blend 27 (also referred to in the figures as "B7001" or "Armor Lead Blend") was prepared and set aside as described (Example 1). A separate blend of oils, denoted as Blend 58, was prepared and set aside. The composition of this blend in weight percent format is provided below:

TABLE B

| Blend 58 from Oils | | |
| --- | --- | --- |
| CAS | Description | Wt/wt |
| 99-87-6 | Para-Cymene | 1.870% |
| 80-56-8 | Alpha-Pinene, 98% | 4.664% |
| 4180-23-8 | Trans-Anethole | 19.305% |
| 89-83-8 | Thymol | 36.719% |
| 78-70-6 | Linalool Coeur | 37.442% |

Various amounts of each blend (to achieve a final concentration ranging from 0.1 µg/mL to 10 µg/mL) were administered to the endoparasite *Ascaris suum* in RPMI 1640 culture media containing antibiotics and antimycotic agents (3 worms per test). The worms were then checked at 30 minutes, 120 minutes, 320 minutes and 72 hours after administration of the blends to determine the numbers of worms killed by the addition of the blend. As a control, a solution of surfactant (sugar ester OWA 1570) was tested separately. As illustrated in FIG. 5, the results show that at high concentrations of the blends (10 µg/mL), the worms died within 30 minutes. At the intermediate concentrations (1 µg/mL, 0.5 µg/mL), the effect of the administered blends on worm mortality were observed within 6 hours of administration, while at the lowest concentrations (0.1 µg/mL), the mortality effect was observed within 3 days.

A similar experiment was conducted on *Toxocara canis*, an endoparasite that infects canine dogs. Groups of 6 worms incubated in culture media were exposed to 10 µg/mL or 1 µg/mL of Blend 58 or to 10 µg/mL of surfactant control, and the worms were then checked at various times after administration of the compositions to determine the numbers of worms killed by the addition of the blend. Worms exposed to the high and low concentrations of Blend 58 died within 30 minutes of exposure, while worms which were administered surfactant control were viable and continued to move vigorously throughout a 3 day observation period.

Thus, these results indicate that various blends containing natural ingredients are effective in treating endoparasites.

Example 4

Synergistic Response to a Blend Containing Natural Ingredients on *Hymenolepis nana*

Figure 6:
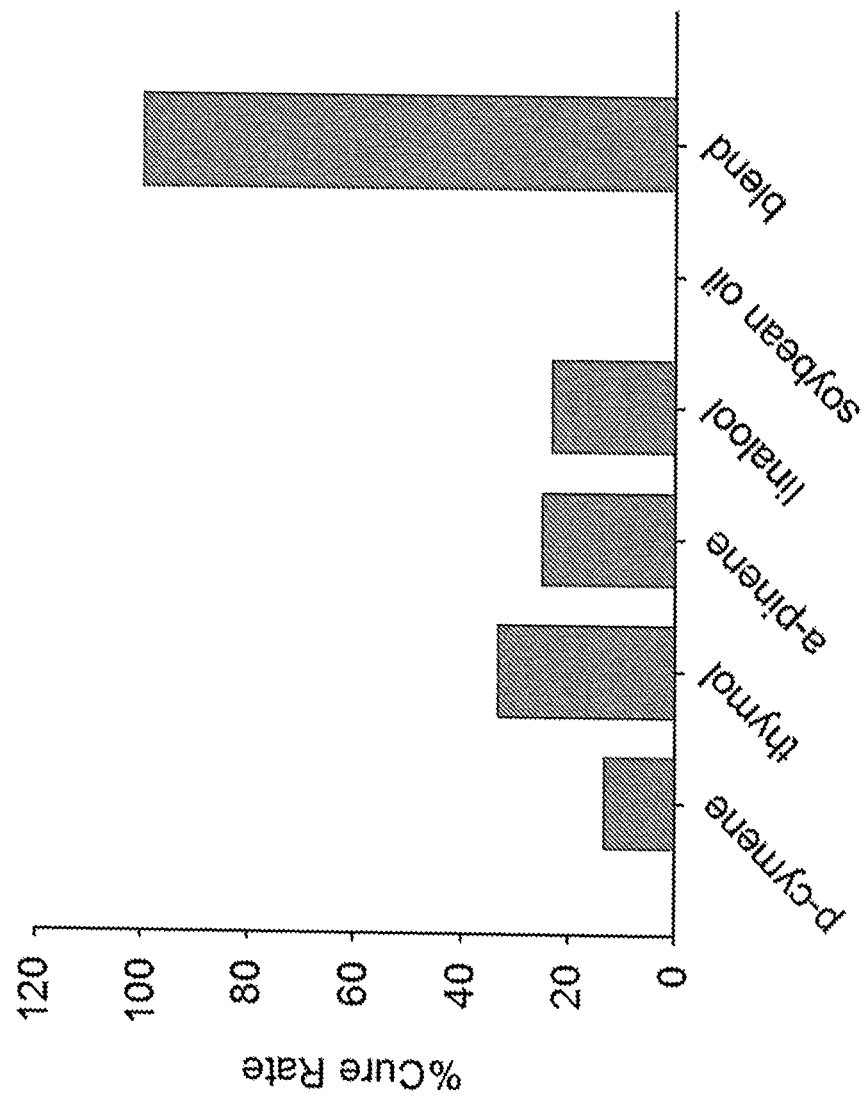

Blend 27 was prepared and set aside as described (Example 1), except that soybean oil was used in place of canola oil. The blend, as well as solutions containing individual ingredients (1=thymol, 2=para-cymene, 3=linalool coeur, 4=alpha-pinene (or "a-pinene"), 5=soybean oil) that make up the blend, were administered to mice infected with the endoparasite *Hymenolepis nana*. About 25 animals were tested per experimental group, and each animal was injected with 200 viable eggs of *H. nana* prior to treatment with the blend of solutions containing individual ingredient (final concentration=100 mg/kg of body weight). A background infection number was established by infecting about 25 animals with *H. nana*. The cure rate ("% Cure Rate") for each tested blend or solution was calculated based on the number of treated animals which were found to be free from *H. nana* eggs and worms divided by the total number of infected animals found in the background infection group. The results indicated that treatment with Blend 27 (containing soybean oil) resulted in a synergistic effect on the cure rate of the endoparasites compared to that observed with administration of the individual ingredients alone (FIG. 6).

Example 5

Figure 7:
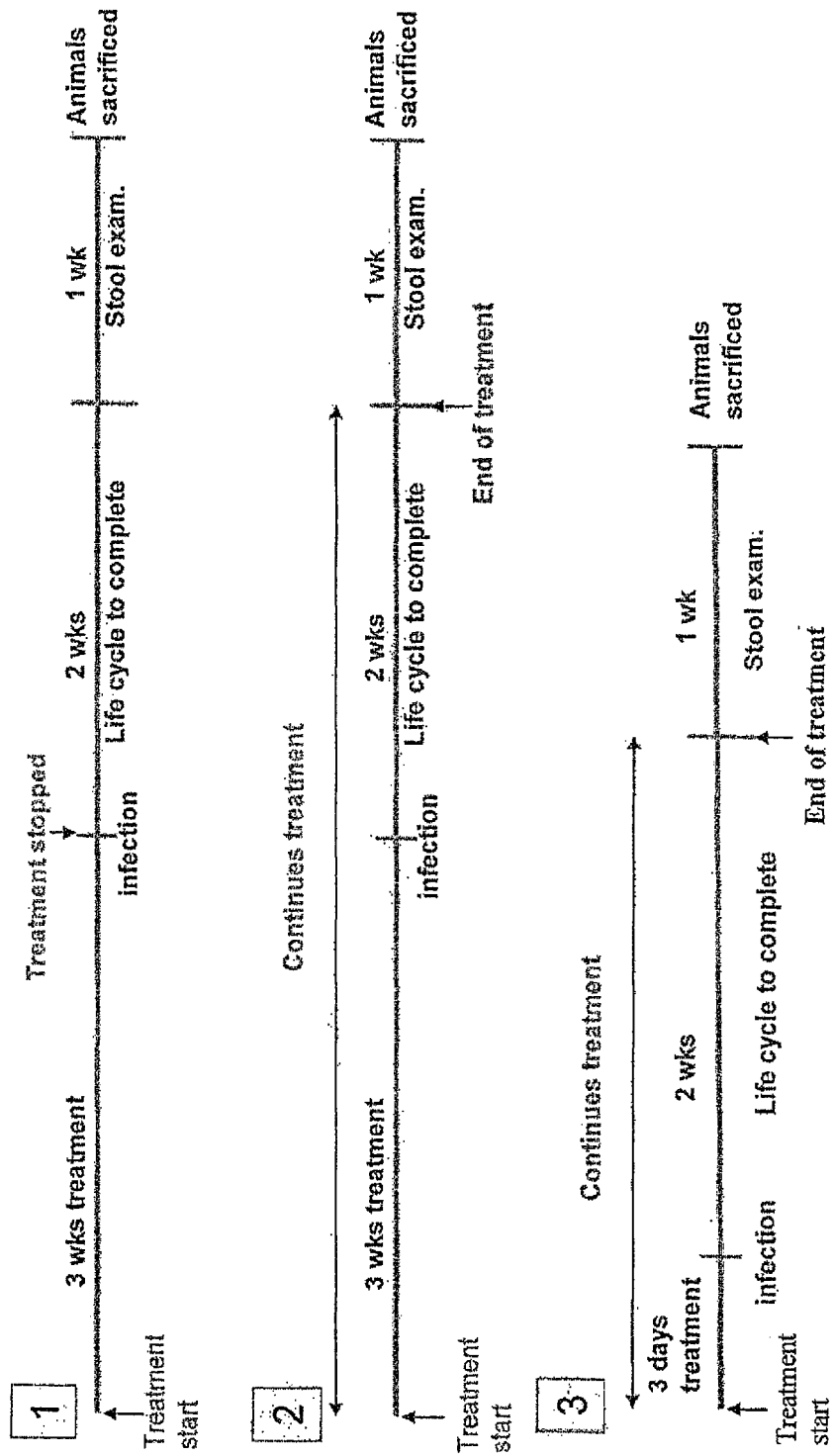

Prophylaxis and Treatment of *Hymenolepis nana* Infection Using Various Dosages of a Blend Containing Natural Ingredients Blend 27 was prepared and set aside as described (Example 1). The blend was then used in various treatment and prophylaxis protocols as outlined in FIG. 7. Briefly, in Protocol 1, Blend 27 was administered in various amounts (ranging from 1 mg/kg of body weight to 100 mg/kg of body weight) to mice for three weeks, followed by infection of each animal with 200 viable eggs of *H. nana* and an 2-week incubation period during which no administration of test compositions was performed. During the third week post-infection, the stool of the treated and infected mice were examined, and the mice were then sacrificed at the end of the third week to ascertain cure rate. In Protocol 2, Blend 27 was administered in various amounts as described for three weeks, followed by infection of each animal with 200 viable eggs of *H. nana*. During the 2 week incubation period following infection, the animals continued to be treated with the blend compositions at the various test amounts. During the third week post-infection, administration of the compositions was stopped, and the stool of the treated and infected mice were examined. The mice were then sacrificed at the end of the third week to ascertain cure rate. In Protocol 3, Blend 27 was at administered in various amounts as described for three days, followed by infection of each animal with 200 viable eggs of *H. nana*. During the 2 week incubation period following infection, the animals continued to be treated with the blend compositions at the various test amounts. During the third week post-infection, administration of the compositions was stopped, and the stool of the treated and infected mice were examined. The mice were then sacrificed at the end of the third week to ascertain cure rate. A background infection number was established by infecting untreated animals with 200 viable eggs of *H. nana*.

The results are illustrated in FIG. 8. It was found that an administered dose of 1 mg/kg of body weight administered according to Protocol 2 resulted in a 78% *H. nana* egg reduction but a 0% cure rate (where the animal is free from eggs and worms). In contrast, a dose of 10 mg/kg of body weight administered according to Protocol 2 resulted in a 79% *H. nana* egg reduction and a 91% cure rate. Finally, doses of 20 mg/kg of body weight and 100 mg/kg of body weight administered according to Protocol 3 resulted in comparable cure rates, although the higher dose resulted in a greater percentage of egg reduction than the lower dose. These results indicate that the blend containing natural ingredients is effective both in curing and preventing *H. nana* infections in animals.

Example 6

Initial Safety Assessment of a Blend Containing Natural Ingredients

Blend 27 was prepared and set aside as described (Example 1). The blend was administered to animals infected with the endoparasite *H. nana* at a dose of 100 mg/kg of body weight for a period of 5 weeks. A control contained infected animals that did not receive any treatment. Data was collected from both groups during the treatment period until the animals were sacrificed. The collected data and observations included: blood samples, fetal matter consistency, change in water intake, change in food intake and change in body weight. In addition, the animals were monitored for internal bleeding.

The results of blood analysis throughout the 5-week administration period indicated that no significant physiological differences were found between non-treated infected animals compared to infected animals that received treatment. In addition, relative to the control group of animals, the infected and treated animals appeared to have: (1) normal appearance in fecal matter consistency, (2) normal consumption in water intake, (3) normal consumption in food intake, and (4) no significant difference in body weight. Finally, no internal bleeding was observed in the infected and treated animals.

Thus, the results indicate that the blend containing natural ingredients are safe and do not introduce any significant medical risks.

Example 7

Treatment of *Hymenolepis nana* Infection Using Various Dosages of an Encapsulated Blend Containing Natural Ingredients Blend 27 (also referred to in the figures as "Armor Blend (B7001)") was prepared and set aside as described (Example 1). The blend was then encapsulated according to standard protocols using either zein, shellac, or a combination of 25% zein/75% shellac. The encapsulated blends were then administered to mice infected with the endoparasite *H. nana* in various daily dosages ranging from 1 mg/day to 5 mg/day. The cure rate was then calculated based on the number of mice found to be free of *H. nana* eggs and worms at the conclusion of treatment relative to the number of mice that were infected. In addition, the % reduction in egg count was also determined for the treated animals.

The results are illustrated in FIGS. 9 and 10. It was found that all three encapsulation formulations of the blend were effective in curing *H. nana* infection relative to a infected control group which did not receive treatment. In addition, the encapsulation formulations of the blend were found to be effective in reducing the *H. nana* egg counts relative to that of the untreated but infected control group. A separate analysis was conducted on the encapsulated formulations to ascertain the volume percent ranges of the individual ingredients of the blend. Although the individual ingredients were found in varying volume percentages in each encapsulated formulation, the results indicate that the blend retained anti-parasitic activity. Briefly, an appropriate target range for each ingredient of the blend was observed as follows: ("Chemical A") alpha-pinene: 4.2% (v/v) to 6.8% (v/v); ("Chemical B") para-cymene: 22.0% (v/v) to 38.1% (v/v); ("Chemical C") linalool: 7.8% (v/v) to 14.9% (v.v); and ("Chemical D") thymol: 42.8% (v/v) to 64.4% (v/v).

Example 8

Residual Activity of Various Blends Containing Natural Ingredients Against the Common Cat Flea Various blends containing natural ingredients were tested for their residual effects, i.e., ability to affecting pest control for an extended period of time. Two blends, denoted Blend 11A (referred to in the figures as "25b/4a (B5028)") and Blend 8 (referred to in the figures as "25b/4b") were prepared and set aside. The compositions of these blends in weight percent format is provided below:

TABLE C

| Blend 11A from Oils | | |
| --- | --- | --- |
| CAS | Description | Wt/wt |
| 8007-46-3 | Thymol Oil White | 20.59% |
| 110-27-0 | Isopropyl myristate | 34.29% |
| 68917-75-9 | Wintergreen Oil | 45.11% |

TABLE D

| Blend 8 from Oils | | |
| --- | --- | --- |
| CAS | Description | Wt/wt |
| 8007-46-3 | Thymol Oil White | 12.38% |
| 68917-75-9 | Wintergreen Oil | 31.32% |
| 5989-27-5 | D-limonene | 56.30% |

Forty (40) insects (*Ctenocephalides felis*, or the common cat flea) were introduced to various test surfaces coated with a formulation (diluted to a final concentration of 30% (v/v)) as described above. Briefly, the formulations were first applied with a pipetter to each test surface in a uniform manner equivalent to an application rate of 1 gallon per 1000 square feet. Two hours after application of the blend or commercial agent, 10 insects were placed on each treated surface, and kill efficacy was measured at about 30 minutes, 1 hour, 4 hours and 24 hours after continuous exposure to the treated surface. The insects were confined to the surface of the panel by placing a mesh-topped container over the insects on the panel. Four replicates of each product were tested on four (4) individual panels, with 10 insects per replicate being tested on each panel.

The residual activity, expressed based on mortality, is set forth in FIG. 11. The results indicate that Blend 11A ("25b/4a (B5028)") was effective in killing the insects within 30 minutes of exposure on all test surfaces. Blend 8 ("Blend 25b/4b") was effective in killing the insects within 30 minutes of exposure on stainless steel and collagen membrane surfaces but less so on the vinyl test surface. Both blends were as effective in killing the insects within 30 minutes of exposure as a commercial blend ("Sergeant's Nature's Guardian Flea and Tick"), indicating that the blends containing natural ingredients can be employed as an effective substitute for commercial blends containing synthetic ingredients.

Example 9

Comparison of a Blend Containing Natural Ingredients with a Commercial Agent Against the Common Cat Flea A blend containing natural ingredients was compared against a commercial agent ("Sergeant's Nature's Guardian Flea and Tick") for the ability to control *Ctenocephalides felis*, or the common cat flea. A blend, denoted Blend 75 (referred to in the figures as "F-4002"), was prepared and set aside. The compositions of the blend in weight percent format is provided below:

TABLE E

| Blend 75 from Oils | | |
|---|---|---|
| CAS | Description | Wt/wt |
| 11138-66-2 | Xanthan Gum | 0.275% |
| 590-00-1 or 24634-61-5 | Potassium Sorbate | 1% |
| | Blend 74 | 16.9% |
| 7732-18-5 | Water | 81.82% |

The blend (Blend 74) used to make Blend 75 contains the compositions in weight percent format as provided below:

TABLE F

| Blend 74 from Oils | | |
|---|---|---|
| CAS | Description | Wt/wt |
| 8002-43-5 | Lecithin | 0.20% |
| 9007-48-1 | Polyglycerol-4-oleate | 0.90% |
| 7732-18-5 | Water | 9.8% |
| | Blend 11A | 89.1% |

The composition of Blend 1 IA is as described in Example 8.

The blend or the commercial agent (at a final concentration of 5% (v/v) or 2.5% (v/v) was sprayed onto a collagen membrane surface and allowed to dry. The insects were then introduced onto the treated surface, and mortality was determined at 1 hour, 4 hours and 24 hours after exposure. A control surface was treated with an application of water containing 1% sodium lauryl sulfate (SLS).

Figure 12:
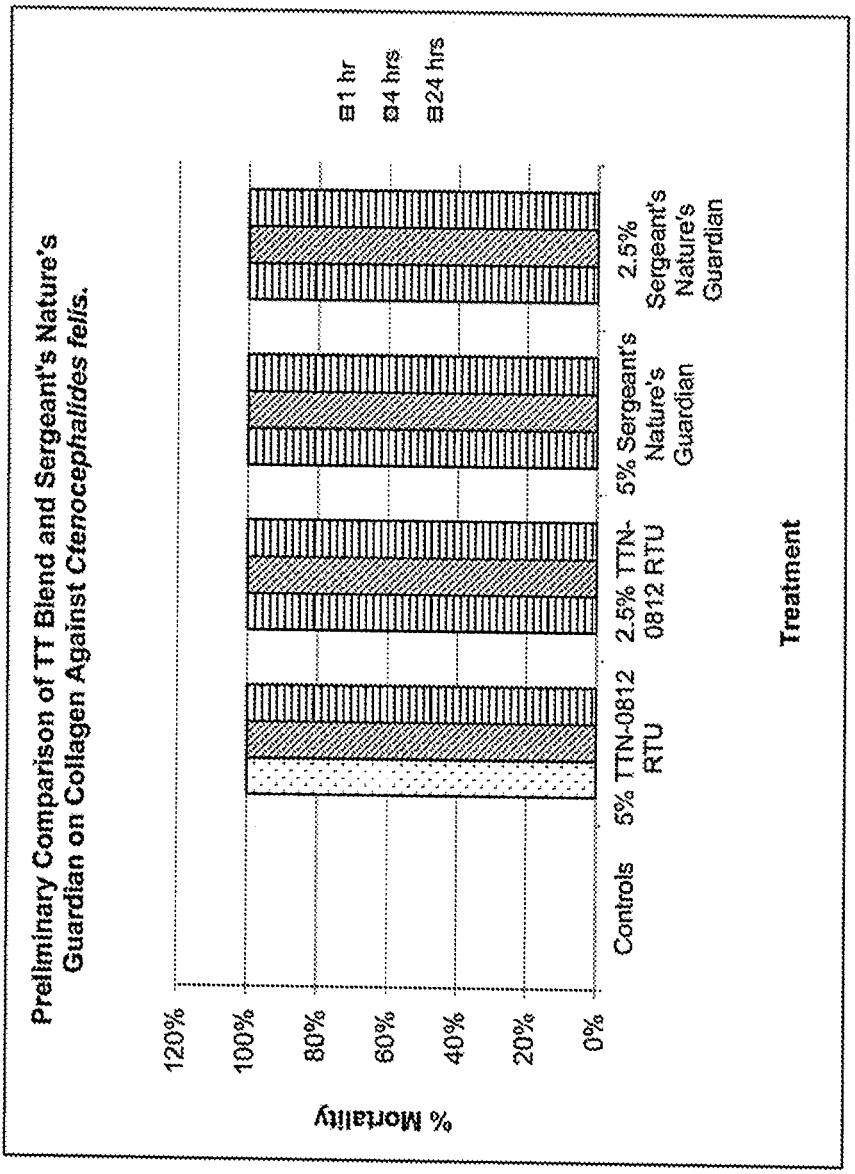
FIG. 12 is a bar graph illustrating the effect of Blend 75 ("F-4002") at different concentrations on the mortality of the ectoparasite *Ctenocephalides felis* (cat flea) at 1, 2 and 4 hours after exposure compared to a commercial brand at the same comparison concentrations.

The results are illustrated in FIG. 12. As indicated in the figure, both concentrations of Blend 75 ("F-4002") were as effective as the commercial agent at the same comparison concentrations in killing the insects at 1, 4 and 24 hours after exposure to the treated surface. The results indicate that the blend containing natural ingredients can be employed as an effective substitute for commercial blends containing synthetic ingredients.

Example 10

Comparison of a Blend Containing Natural Ingredients with a Commercial Agent Against the Wood Tick A blend containing natural ingredients was compared against a commercial agent ("Sergeant's Nature's Guardian Flea and Tick") for the ability to control *Dermacentor andersoni*, or the wood tick. Blend 75 (referred to in the figures as "F-4002") was prepared as described (Example 9).

The blend or the commercial agent (at a final concentration of 5% (v/v) or 2.5% (v/v) was sprayed onto a collagen membrane surface or a stainless steel surface and allowed to dry. The insects were then introduced onto the treated surface, and mortality was determined at 30 minutes, 1 hour, 2 hours, 4 hours and 24 hours after exposure. A control surface was treated with an application of water containing 1% sodium lauryl sulfate (SLS).

Figure 13:
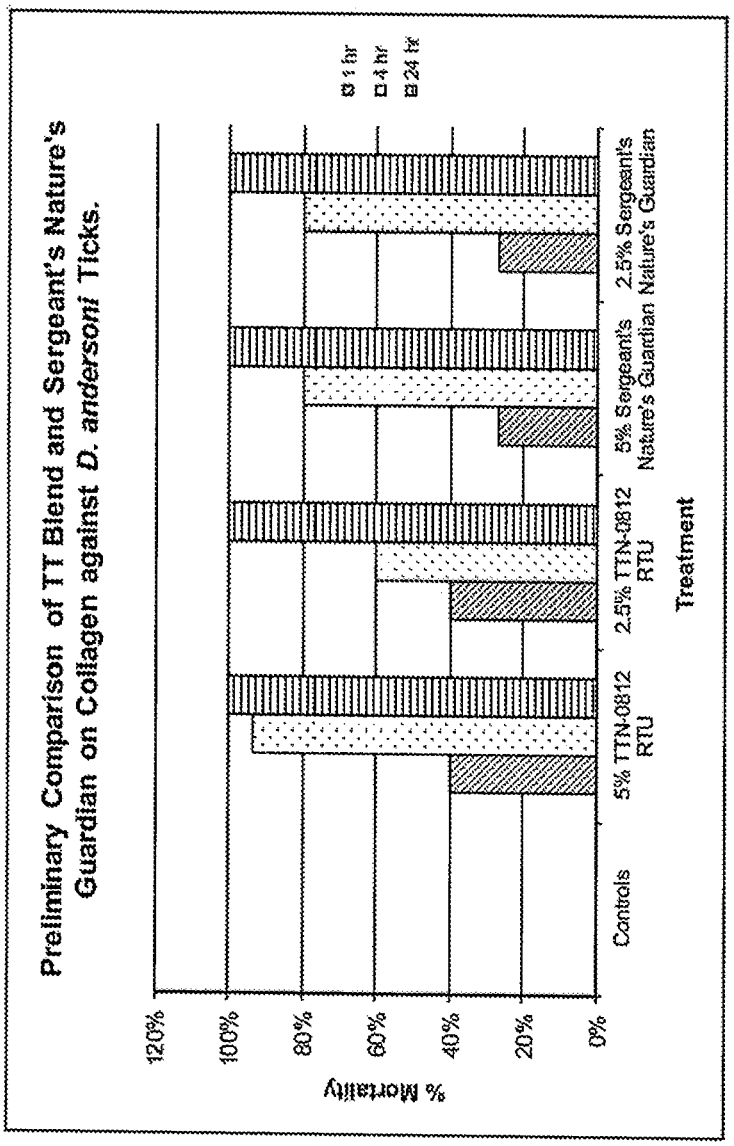
FIG. 13 is a bar graph illustrating the effect of Blend 75 ("F-4002") at different concentrations on the mortality of the ectoparasite *Dermacentor andersoni* (wood tick) at 1, 2 and 4 hours after exposure compared to a commercial brand at the same comparison concentrations.
Figure 14:
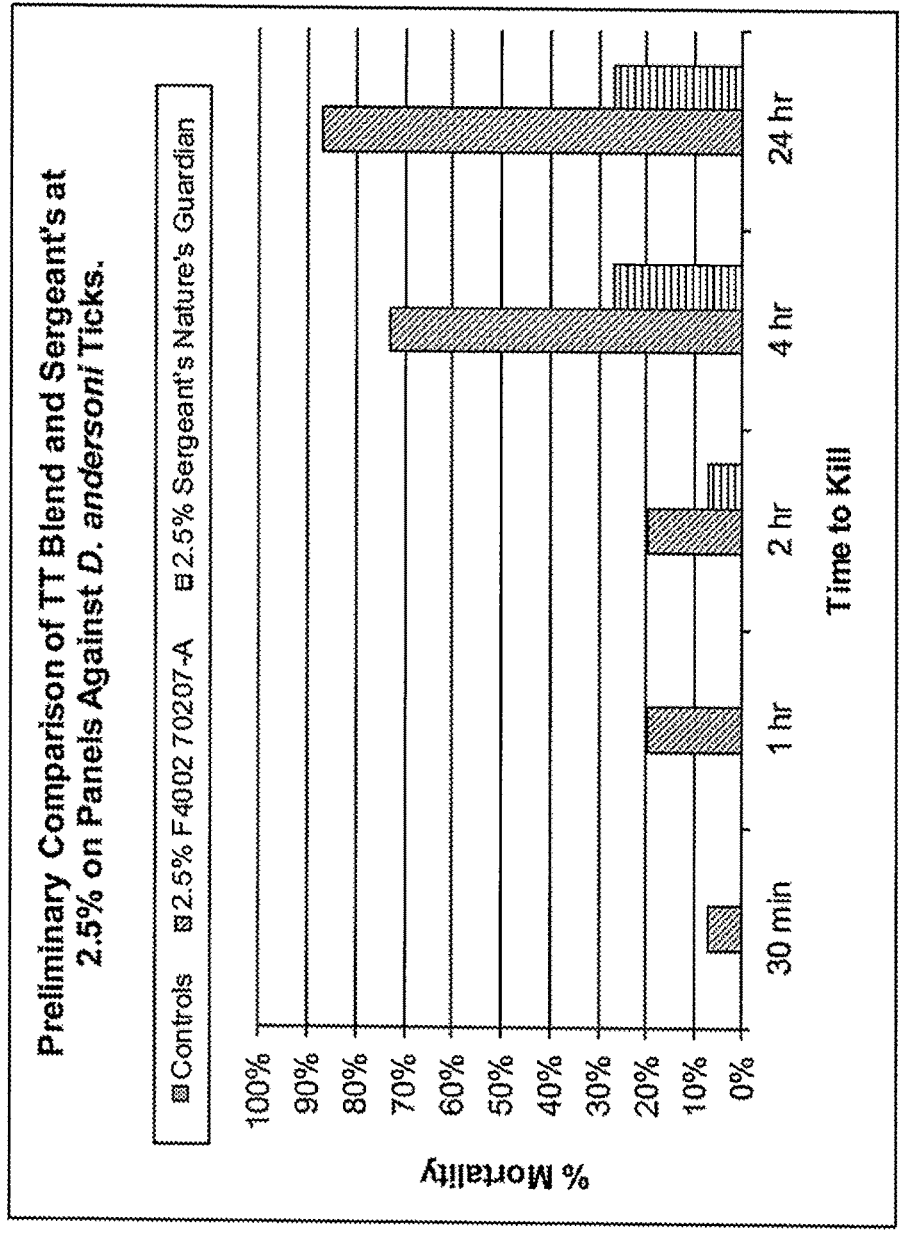
FIG. 14 is a bar graph illustrating the effect of Blend 75 ("F-4002") at 2.5% (v/v) on the mortality of the ectoparasite *Dermacentor andersoni* (wood tick) at 1, 2, 4 and 24 hours after exposure compared to a commercial brand at the same comparison concentration.

The results are illustrated in FIGS. 13 and 14. As indicated in FIG. 13, for the collagen membrane surface, both concentrations of Blend 75 ("F-4002") were as effective as the commercial agent at the same comparison concentrations in killing the insects at 1, 4 and 24 hours after exposure to the treated surface. As illustrated in FIG. 14, for the stainless steel surface, the blend was more effective than the commercial agent at the same comparison concentration in killing the insects at all the observation times.

Thus, the results indicate that the blend containing natural ingredients can be employed as an effective substitute for commercial blends containing synthetic ingredients.

Example 11

Residual Activity of a Blend Containing Natural Ingredients Against the Wood Tick A blend containing natural ingredients was compared against a commercial agent ("Sergeant's Nature's Guardian Flea and Tick") for the ability to control *Dermacentor andersoni*, or the wood tick. Blend 75 (referred to in the figures as "F-4002") was prepared as described (Example 9).

The blend or the commercial agent (at a final concentration of 5% (v/v) or 2.5% (v/v) was sprayed onto a stainless steel surface and allowed to dry. The insects were then introduced onto the treated surface, and mortality was determined at 72 hours after exposure. A control surface was treated with an application of water containing 1% sodium lauryl sulfate (SLS).

The residual activity, expressed based on mortality, is set forth in FIG. 15. The results indicate that, at a final concentration of 5% (v/v), Blend 75 ("F-4002") was as effective in killing the insects within 72 hours of exposure as the commercial agent. In addition, at a final concentration of 2.5% (v/v), Blend 75 was more effective in killing the insects within 72 hours of exposure as the commercial agent exposure on all test surfaces. The results thus indicate that a blend containing natural ingredients can be employed as an effective substitute for commercial blends containing synthetic ingredients in controlling the wood tick.

Example 12

Comparison of the Activity of Various Blends Containing Natural Ingredients and Commercial Agents Against Various Ectoparasites Various blends containing natural ingredients were compared against a commercial agent ("Sentry-Natural Defense") for the ability to control *Ctenocephalides felis*, or the common cat flea and *Rhipicephalus sanguineus* (a tick). The various blends, denoted Blends 19 (referred to in the figures as "HL1"), 6 (referred to in the figures as "HL3"), 11A (referred to in the figures as "B5028"), 42 (referred to in the figures as "AAT") and 123 (referred to in the figures as "AAT Plus"), were prepared and set aside. The compositions of the remaining blends in weight percent format are provided below:

TABLE G

Blend 19 from Oils

| CAS | Description | Wt/wt |
|---|---|---|
| 5989-27-5 | D-Limonene | 27.35% |
| 8007-46-3 | Thyme Oil White | 30.08% |
|  | Lilac Flower Oil (LFO) | 42.57% |

TABLE H

Blend 6 from Oils

| CAS | Description | Wt/wt |
|---|---|---|
| 121-33-5 | Vanillin | 0.8% |
| 120-57-0 | Piperonal | 3.2% |
| 106-24-1 | Geraniol | 4.3% |
| 78-70-6 | Linalool Coeur | 6.4% |
| 78-69-3 | Tetrahydrolinalool | 7.8% |
| 5989-27-5 | D-Limonene | 8.8% |
| 110-27-0 | Isopropyl myristate | 9.5% |
| 977017-84-7 | Black Seed Oil (BSO) | 26.2% |
| 119-36-8 | Methyl salicyclate | 33% |

TABLE I

Blend 42 from Oils

| CAS | Description | Wt/wt |
|---|---|---|
| 540-18-1 | Amyl butyrate | 23.04% |
| 8007-46-3 | Thyme Oil White | 24.747% |
|  | Anise Star of Oil | 52.213% |

TABLE J

Blend 123 from Oils

| CAS | Description | Wt/wt |
|---|---|---|
|  | Genistein | 0.01% |
| 540-18-1 | Amyl butyrate | 23.04% |
| 8007-46-3 | Thyme Oil White | 24.75% |
|  | Anise Star of Oil | 52.2% |

The composition of Blend 11A is as described in Example 8.

Each blend or commercial agent was diluted to a final concentration of 7.4% (v/v) in a diluent solution of 40% (v/v) isopropyl alcohol and 60% (v/v) isopropyl myristate. The target dose rate of each agent was 3 grams/kg of body weight, as applied on day 0. About 24 hours after treatment, 100 fleas (*Ctenocephalis felis*) and 50 ticks (*Rhipicephalus sanguineus*) were applied to three dogs in each experimental group. The number of insects were counted 24 hours after infestation with timed body counts without removal or destruction of the pests. After an additional 48 hour period, the number of insects were counted again before being subsequently removed and destroyed. Individual efficacy values were calculated as a percent reduction from the mean count obtained from the control (untreated group).

The results are illustrated in FIG. 16. As shown, the blends containing the natural ingredients were comparable to the commercial agent in killing fleas and ticks at 2-days and 4-days post treatment. The results thus indicate that a blend containing natural ingredients can be employed as an effective substitute for commercial blends containing synthetic ingredients in controlling the fleas and ticks.

Example 13

Comparison of the Activity of a Blend Containing Natural Ingredients with Commercial Agents Against Mosquitoes Various formulations of a blend containing natural ingredients were compared against a commercial agent ("Off-Skintastic") for the ability to repel *Aedes aegypti* (or the mosquito). The blend, denoted Blend 4 (also referred to in the figures as "XL101"), was prepared and set aside. The compositions of the blend in weight percent format are provided below:

TABLE K

Blend 4 from Oils

| CAS | Description | Wt/wt |
|---|---|---|
| 977017-84-7 | Black Seed Oil (BSO) | 49.87% |
|  | Lilac Flower Oil (LFO) | 50.13% |

"XL101Natural" denotes Blend 4 diluted to a final concentration of 30% (v/v) in a diluent containing water and surfactant (1% SLS). "XL101D" denotes Blend 4 diluted to a final concentration of 30% (v/v) in denatured alcohol.

Figure 17:
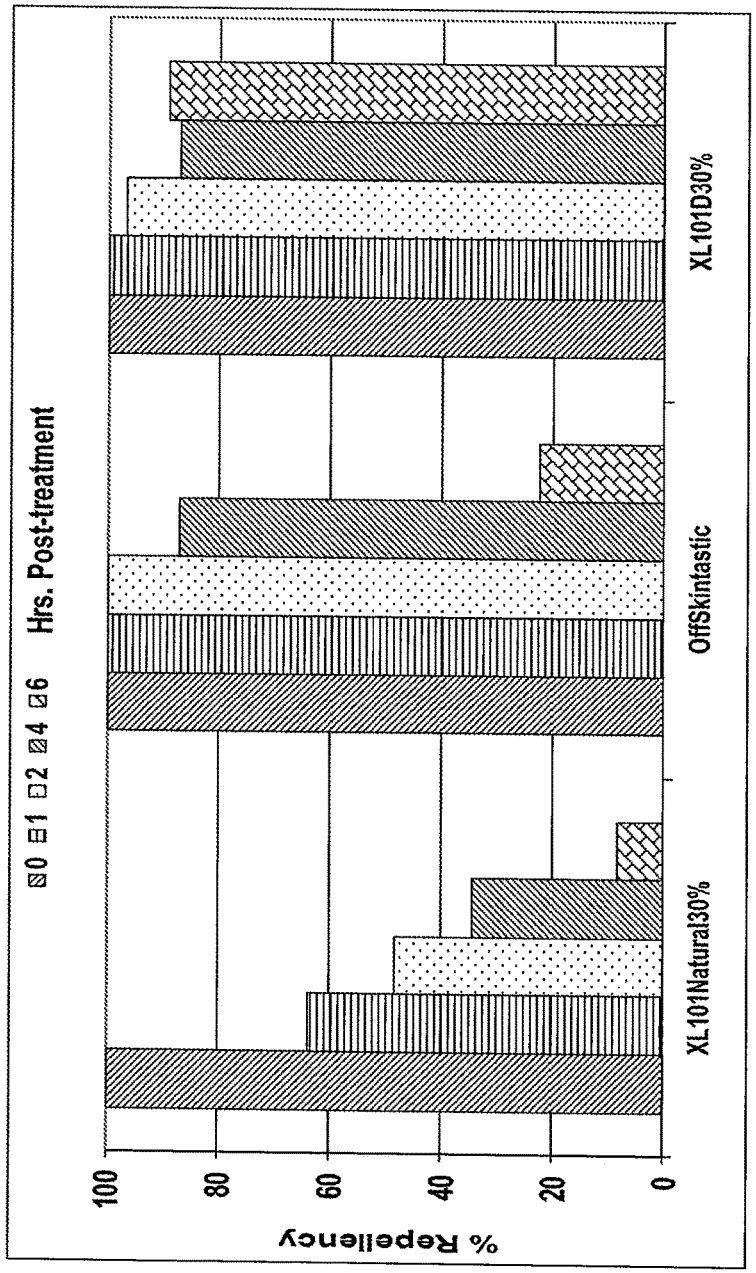
FIG. 17 is a bar graph illustrating the repellency of different formulations of Blend 4 ("XL101") on the ectoparasite *Aedes aegypti* at 0, 1, 2, 4 and 6 hours post-treatment compared to a commercial brand at the same comparison concentration.

The various formulations or commercial agent were applied to human skin surface with a brush at a dose of 1 mL/450 cm$^2$. All formulations were provided at a final concentration of 30% (v/v). The skin surface was then exposed to mosquitoes for 2-minute biting counts at 0, 1, 2, 4 and 6 hours post-treatment with the blends or commercial agent. As illustrated in FIG. 17, Blend 4 ("XL101"), particularly the formulation in denatured alcohol, was comparable or more effective than the commercial agent in repelling mosquitoes. Thus, the results indicate that a blend containing natural ingredients can be employed as an effective substitute for commercial blends containing synthetic ingredients in repelling mosquitoes.

Example 14

Comparison of the Duration of Repellency of a Cream Formulation of a Blend Containing Natural Ingredients with a Commercial Agent Blend 4 was prepared as described (Example 13) and set aside. The blend was formulated into various skin cream formulation that contained 25% (v/v) of the blend.

Figure 18:
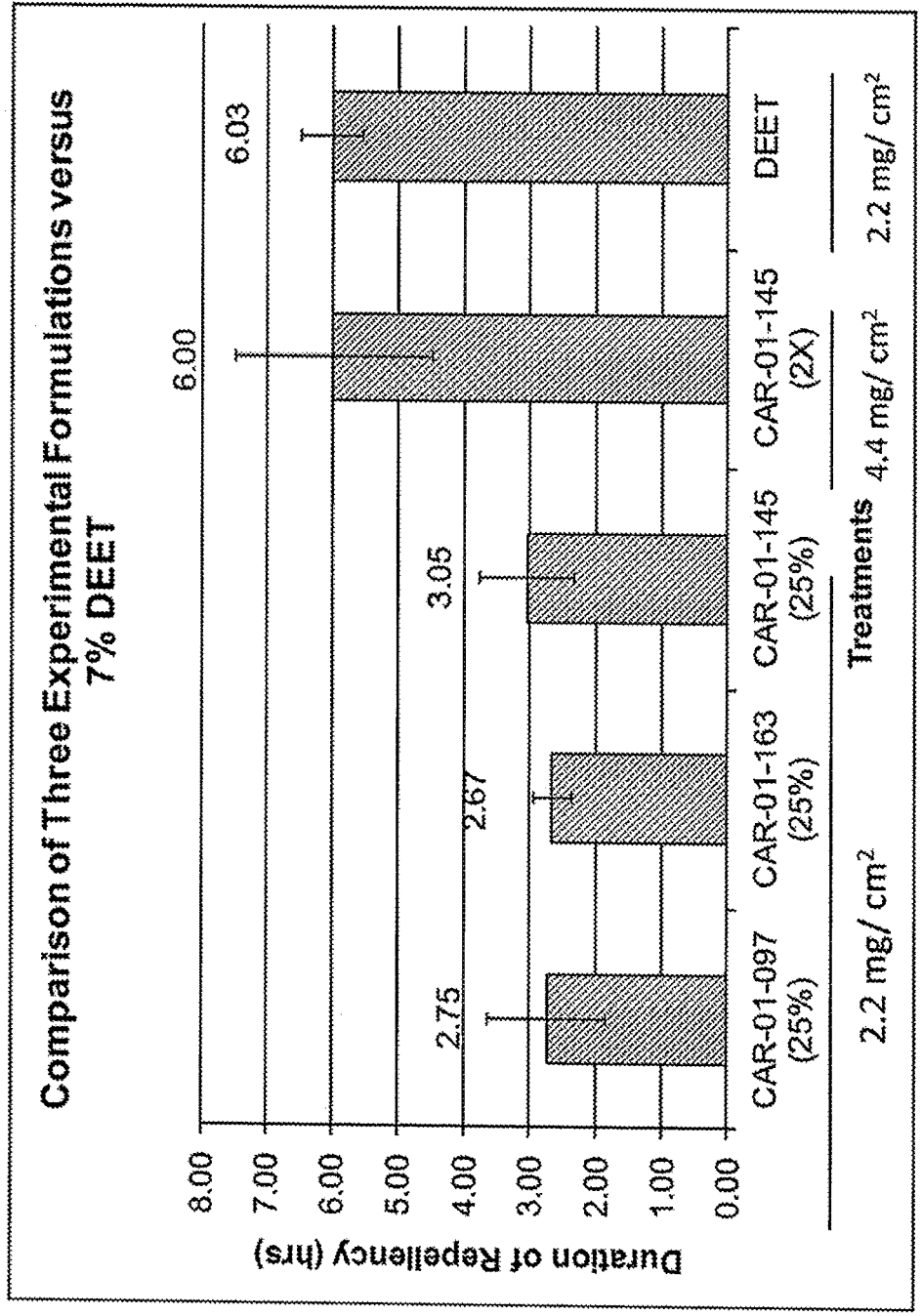
FIG. 18 is a bar graph illustrating the duration of repellency of different skin cream formulations of Blend 4 ("CAR-01") on the ectoparasite *Aedes aegypti* compared to a commercial brand at the same comparison concentration.

The various skin cream formulations of Blend 4 (referred to in the figures as "CAR-01-097", "CAR-01-163", and "CAR-01-145"), or a commercial agent ("DEET"), was applied to human skin surface with a brush at a dose of 2.2 mg cream/cm². The "CAR-01-145" formulation was applied twice to human skin surface ("2×"). The skin surface was then exposed to mosquitoes. As illustrated in FIG. 18, skin cream formulations of Blend 4, are effective in repelling mosquitoes for 2-3 hours. Two applications of the Blend 4 skin cream formulation labeled as "CAR-01-145" formulation were as effective as a single application of the commercial agent in duration of repellency of mosquitoes. Thus, the results indicate that a skin cream formulation containing a blend of natural ingredients can be employed as substitute for commercial blends containing synthetic ingredients in repelling mosquitoes.

Example 15

Use of Various Blends Containing Natural Ingredients for Controlling Thrips

Various blends containing natural ingredients were studied for the ability to control thrips. The various blends, denoted Blend 11B and Blend 8, were prepared and set aside. The compositions of the blends in weight percent format are provided below:

TABLE L

| | Blend 11B from Oils | |
| --- | --- | --- |
| CAS | Description | Wt/wt |
| 68917-75-9 | Wintergreen Oil | 24.82% |
| 110-27-0 | Isopropyl myristate | 35.94% |
| 8007-46-3 | Thyme Oil White | 39.27% |

The composition of Blend 8 is as described in Example 8.

Figure 19:
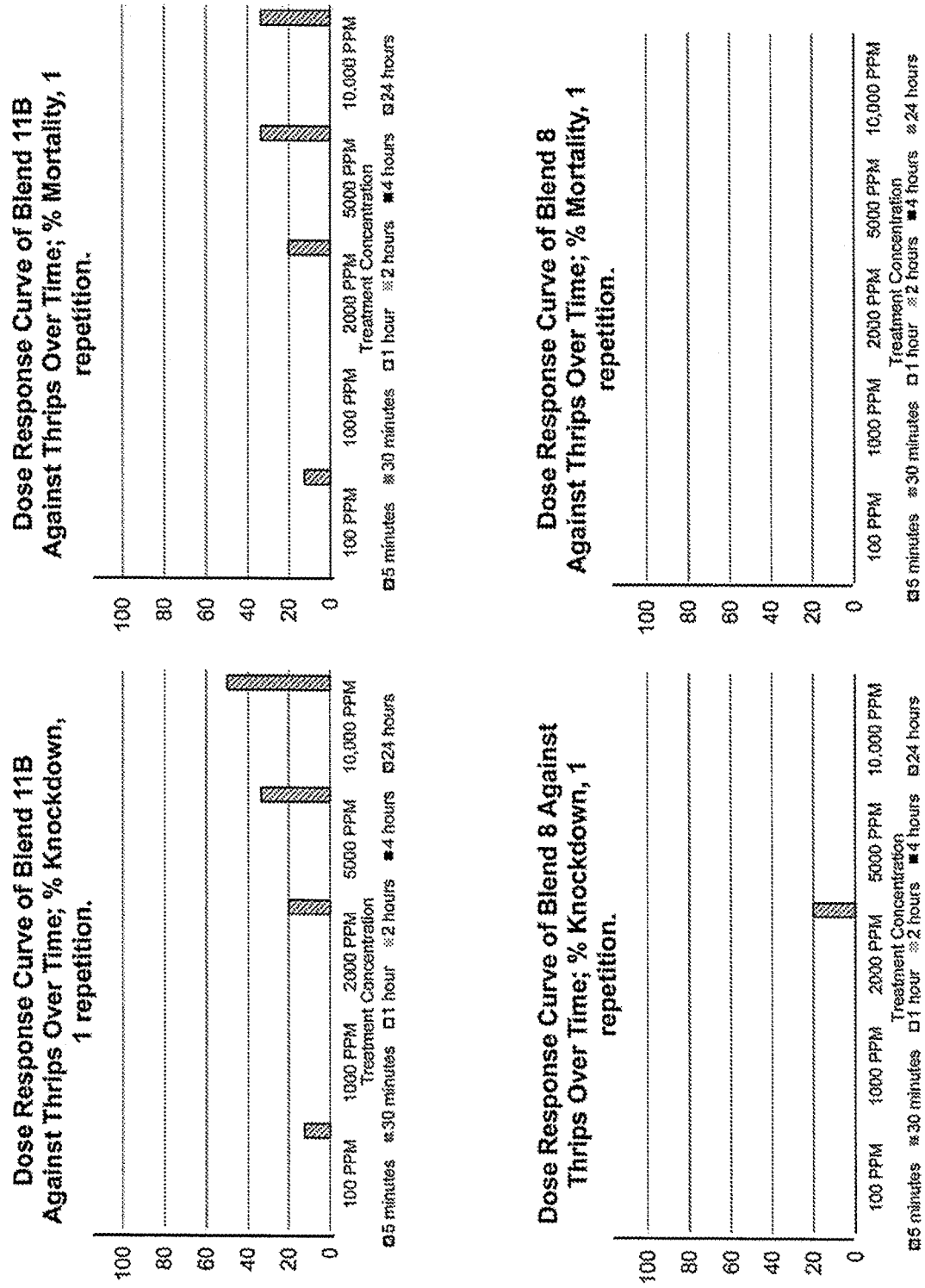
FIG. 19 are bar graphs illustrating the effect of various blends (Blends 11B and 8) on the knockdown and mortality of *thrips* at various concentrations.

The blends were applied at various doses ranging from 100 ppm to 10,000 ppm to a surface. Thrips were then introduced to the treated surfaces, and pest control was measured as the number of insects that were knocked down or died upon introduction to the treated surface. The results are illustrated in FIG. 19. As shown, Blend 11B was effective in controlling thrips, as measured by % knockdown and % mortality, with higher doses illustrating better efficacy.

Example 16

Efficacy of a Direct Spray Formulation Containing a Blend of Natural Ingredients on Ticks Various blends containing natural ingredients were studied for the ability to control *Dermacentor andersoni* (Rocky Mountain wood tick). The various blends, denoted Blend 1 (referred to in the figures as "CL17"), 11A (referred to in the figures as "25b/4a"), 8 (referred to in the figures as "25b/4b"), DKSH/TT 1 (Blend 11A in 4% (v/v) pyrethrum), DKSH/TT 2 (Blend 12 in 4% (v/v) pyrethrum) and DKSH/TT 3 (Blend 19 in 4% (v/v) pyrethrum), were prepared and set aside. The compositions of the blends in weight percent format are provided below:

TABLE M

| | Blend 1 from Oils | |
| --- | --- | --- |
| CAS | Description | Wt/wt |
| | Thyme Oil White | 3.30% |
| | Lilac Flower Oil (LFO) | 4.40% |
| | Lime Oil (as exemplified in Blend 65) | 10.0% |
| | D-Limonene | 82.3% |

TABLE N

| | Blend 12 from Oils | |
| --- | --- | --- |
| CAS | Description | Wt/wt |
| | Vanillin | 2.48% |
| | D-Limonene | 9.90% |
| | Piperonal (aldehyde) | 9.97% |
| | Geraniol Fine FCC | 10.30% |
| | Linalool Coeur | 14.14% |
| | Tetrahydrolinalool | 24.29% |
| | Isopropyl myristate | 28.92% |

The compositions of Blends 11A and 8 are as described in Example 8. The composition of Blend 19 is as described in Example 12.

Each blend was administered directly to ticks placed on a surface, where 1 mL of blend was applied from a spray nozzle located 18 inches from the surface. Blends 1, 11A and 8 were tested at a final concentration of 30% (v/v), while the "DKSH" blends were tested at a final concentration of 4% (v/v) for each of Blends 11A, 12 and 19. The kill number of ticks was then assessed for each blend at 30 minutes and 4 hours post-spray. The results are illustrated in FIG. 20. Blends 1 ("CL17"), DKSH/TT 1 and DKSH/TT 3 were effective in killing ticks within 30 minutes post-exposure, while Blend 11A ("25b/4a") exhibited high killing efficacy within 4 hours of exposure.

Example 17

Comparison of Residual Activity of Various Blends of Natural Ingredients with a Commercial Agent The residual activity of various blends containing natural ingredients were compared against that of a commercial agent ("Sergeant's Nature's Guardian Natural Flea and Tick") for the ability to control *Dermacentor Andersoni* (Rocky Mountain wood tick). Two blends, Blends 11A (referred to in the figures as "25b/4a") and 8 (referred to in the figures as "25b/4b"), were prepared and set aside. The composition of the blends are as described in Example 8.

The blends or commercial agent were applied to blood filled membranes infested with ticks, where each blend contained a final concentration of 6.1% (v/v) of active ingredient. Kill counts were then assessed at 30 minutes, 1 hour, 2 hours and 4 hours after exposure. The results are illustrated in FIG. 21 and show that the Blends 11A ("25b/4a") and 8 ("25b/4b") are as effective or more effective than the commercial agent. Thus, the results indicate that the blends containing natural ingredients, as disclosed herein, can be substituted for a commercial agent in controlling ticks.

Example 18

Fractionation of a Plant Essential Oil and Screening for Fractions with Potential Activity Against a Target Pest An improved insecticide based on an insect-repelling plant essential oil is generated by screening separated fractions of the plant essential oil against the Drosophila Tyramine receptor, Dro-TyrR, and then recombining fractions with higher specific competitive binding ability to Dro-TyrR than the plant essential oil. This is performed in the following steps.

PCR Amplification and Subcloning of Drosophila melanogaster Tyramine Receptor Gene To generate Drosophila cells in culture expressing the cell-surface tyramine receptor for the purposes of screening the plant essential oil fractions, the tyramine receptor is first amplified from Drosophila melanogaster head cDNA phage library that is obtained through the Berkeley Drosophila Genome Project (www.fruitfly.org). Phage DNA is purified from this library using a liquid culture lysate as described in Lech (2001) "Preparing DNA from small-scale liquid lysates" In: Ausubel, J. G., Smith, J. A., Struhl, K. (Eds.), Current Protocols in Molecular Biology. John Wiley & Sons, Inc, pp. 1.13.7. Briefly, gene specific primers used to amplify the open reading frame of the Drosophila tyramine receptor (TyrR) are designed based on the published dro-TyrR sequence by Saudou et al., (1990, Genbank accession #X54794; protein accession #"CAA38565"). These gene specific primers consist of the 5' oligonucleotide: 5'gccgaattcATGCCATCGGCAGATCAGATCCTG3' (SEQ ID NO. 1) and 3'oligonucleotide: 5'taatctagaTCAATTCAGGCCCAGAAGTCGCTTG 3' (SEQ ID NO. 2). Capitalized letters match the tyramine receptor sequence. The 5' oligonucleotide also contains an EcoR I site and the 3' oligonucleotide a Xba I site restriction sites that are indicated by underlined nucleotides. PCR is performed using Vent polymerase (New England Biolabs) with the following conditions: 95° C., 5 min for 1 cycle; 95° C., 30 s; and 70° C., 90 s for 40 cycles; and 70° C., 10 min for 1 cycle. The PCR product is digested with EcoR I and Xba I, subcloned into pCDNA3 and sequenced on both strands by automated DNA sequencing (Vanderbilt Cancer Center). The open reading frame contained in this PCR product encodes a protein of 601 amino acids with a predicted molecular mass of 64 KDa. Based on alignment comparisons using DNA Star Software Program, both sequences of dro-TyrR(Saudou et al., 1990, supra) and the current TyrR are essentially identical, except one residue at location 261 which is cysteine (C) in the dro-TyrR sequence (accession #CAA38565) and tyrosine (Y) in the current TyrR sequence. Hydropathy analysis by the method of Kyte and Doolittle, with a window of 9 amino acids, indicates seven potential transmembrane spanning domains. SecKyte and Doolittle, (1982) J. *Mol. Biol* 157:105-132. The BLAST analysis also indicates that the cloned *Drosophila melanogaster* TyrR is most similar to other biogenic amine receptors.

TyrR is essentially identical to tyr-dro receptor, a tyramine receptor from the fruit fly *Drosophila melanogaster* (Saudou et al., 1990, supra), and to the same sequence, also designated as oct/TyrRreceptor (accession P22270) Arakawa, et al., (1990) Neuron 2:343-354. Protein alignment indicates the cloned TyrR is 66% identical to Amtyrl (Blenau, et al., (2000) *J. Neurochem.* 74:900-908), 48% identical to both Tyr-Loc 1 and Tyr-Loc2 (Vanden Broeck, et al., (1995) *J. Neurochem.* 64:2387-2395), 49% identical to *C. elegans*-Tyr2 (Rex, et al., (2002) *J. Neurochem.* 82:1352-1359), 50% identical to Tyr-*Bombyx mori* (Ohta, et al., (2003) *Insect Mol. Biol.* 12(3):217-223), 56% identical to Tyramine receptor from *Anopheles gambiae* (Genbank, 2003, accession number EA A07468), 29% identical to locus OAR2 (Gerhardt, et al. (1997) *Mol. Pharmacol.* 51:293-300), 27% identical to Pa $oa_1$, an octopamine receptor from *Periplaneta americana* (Bischof, et al., (2004) *Insect Biochem. Mol. Biol.* 34:511-521), and 32% identical to human a2B adenoreceptor (Lomasney, et al., (1990) *Proc. Natl. Acad. Sci. USA* 87:5094-5098).

For expression in Drosophila Schneider S2 cells, the tyramine receptor (TyrR) open reading frame contained in the PCR product described above is excised from pCDNA3 and inserted into pAc5.1/V5-His B (pAC) using the Eco RI and Xba I restriction sites, generating the expression plasmid pAc5.1/V5-His B-tyramine receptor (pAC-TyrR).

Cell Culture and Transfection

Drosophila Schneider 2 (S2) cells, lacking endogenous tyramine receptor (Vanden Broeek et al., 1995; Van Poyer et al., 2001), are used in the current study for stable transfection and expression of tyramine receptor that is amplified from *Drosophila melanogaster* head cDNA phage library. In this regard, cells are grown in Schneider's Drosophila Medium containing 10% heated-inactivated fetal bovine serum (FBS). Medium is supplemented with 50 Units penicillin G/ml, 50 μg streptomycin sulfate/mi. For stable transfection, Drosophila S2 cells are transfected with pAc5.1N5-His B-tyramine receptor (pAC-TyrR) using the calcium phosphate-DNA coprecipitation protocol as described by Invitrogen Drosophila Expression System (DES) manual. The cells are maintained and grown at room temperature (23° C.) in the same medium supplemented with selection agent (25 μg blasticidin/ml medium). Ten clones of stably transfected cells are selected and separately propagated. Clonal cell lines are selected and assayed for receptor expression with whole cell binding by incubating $1\times10^6$ cells in 1 ml insect saline buffer (170 mM NaCl, 6 mM KCl, 2 mM NaHCO3, 17 mM glucose, 6 mM $NaH_2PO_4$, 2 mM $CaCl_2$, and 4 mM $MgCl_2$) with 4 nM $^3$H-tyramine for 20 min at 23° C. Cells are pelleted by centrifugation, washed once with insect saline, and then transferred to scintillation vials. Nonspecific binding is determined by including 100 μM unlabeled-tyramine in the reaction. The clone of cells stably transfected with pAC-TyrR that demonstrates the highest binding affinity to $^3$H-tyramine is propagated for use in identifying improved agents against a target pest. In all exemplary embodiments, S2 cells transfected with pAc5.1N/V5-His B (pAc5.1; the parent vector lacking the tyramine receptor gene) are treated in parallel as negative controls.

For pharmacological binding experiments, membrane fractions from the clone of stably transfected Drosophila S2 cells demonstrating the highest binding affinity to $^3$H-tyramine are isolated and analyzed to determine total, nonspecific and specific binding of $^3$H-tyramine (FIG. 23). To first isolate membranes, Dro-TyrR-expressing S2 cells grown in Drosophila media are harvested in the same media by scraping from the dishes and then rinsing dishes with PBS. The cells are centrifuged at 1000 g for 3 min, washed once with PBS and centrifuged again as previously described. The cells are suspended in ice cold hypotonic buffer (10 mM Tris-Cl, pH 7.4), incubated on ice for 10 min, and lysed using a glass Bounce homogenizer and tight glass pestle (Kontes Glass Co., Vineland, NJ) with 10 strokes. Nuclei are pelleted by centrifugation at 600 g for 5 min. The supernatant is decanted and centrifuged at 30,000 g for 30 min to pellet a crude membrane fraction. The pellet is suspended in binding buffer (50 mM Tris-Cl, 5 mM $MgCl_2$, pH 7.4). Protein concentration is determined by the Bradford Assay (Bio-Rad Laboratories, Hercules, CA). Membranes are frozen on dry ice then stored at −75° C. in aliquots.

To then assay total, specific, and nonspecific binding of $^3$H-tyramine, radioligand binding is performed in 500 µl binding buffer containing 10-50 µg membrane protein and 4 nM $^3$H-tyramine. The binding reaction is incubated at 23° C. in the presence and absence of 10 µM unlabeled tyramine. Reactions are terminated after 60 min by addition of 3 ml ice cold binding buffer and filtered over GF/C filters that have been soaked for 30 min in 0.3% polyethylenimine. Filters are rinsed one additional time with 3 ml binding buffer.

For the determination of $K_d$ and $B_{max}$, a range of $^3$H-tyramine is used from 0.1 to 30 nM, and 10 µM unlabeled tyramine is used as a competitor to determine nonspecific binding. The $K_d$ and $B_{max}$ for specific binding are determined to be 2.557 nM and 0.679 pmol receptor/mg membrane protein, respectively. Membrane fractions from Drosophila S2 cells stably transfected with the empty pAc5.1 do not demonstrate specific binding. The high affinity binding of $^3$H-tyramine by the membrane expressing TyrR indicate this is a suitable ligand to be used for competition binding experiments.

Figure 24:
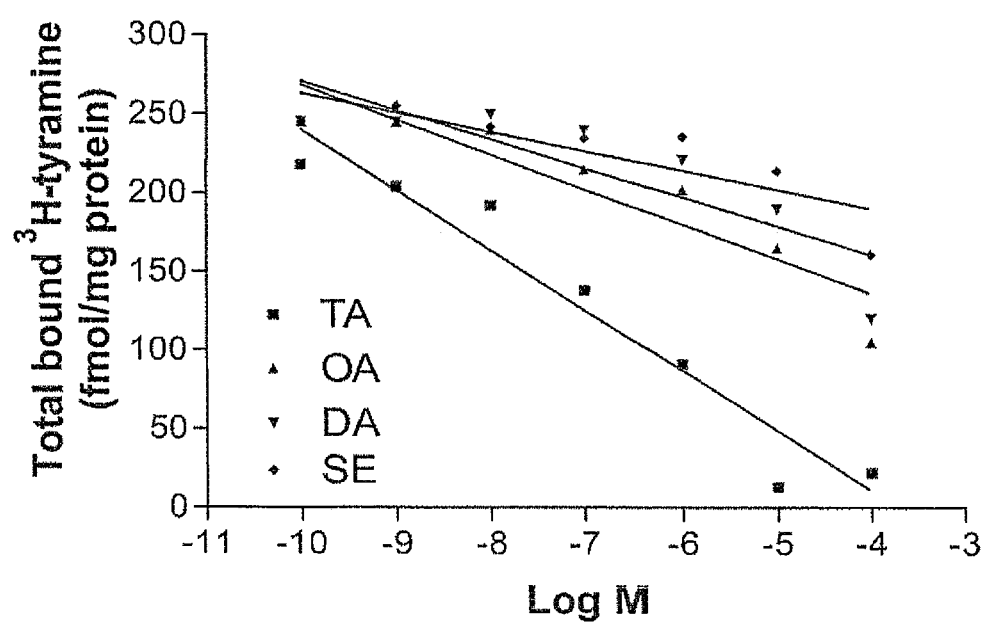
FIG. 24 is a graph showing an inhibition binding curve of $^3$H-tyramine to the membrane fractions of S2 cells expressing a tyramine receptor ("Tyr$^R$").

The affinity of potential natural ligands of TyrR is determined in a competitive binding assay with $^3$H-tyramine and five biogenic amines (FIG. 24 and Table O). Tyramine (TA) has the lowest $K_i$(1.27 µM) for Drosophila TyrR followed by DL-octopamine (OA; 28.68 µM). The decreasing order of affinity for the biogenic amines is TA>OA>dopamine (DA)>serotonin (SE)>histamine (His). These values are about the same as those obtained for tyr-dro (Saudou et al., 1990, supra). The affinity of TA is about 22.58 fold higher than DL-octopamine for TyrR. These results therefore indicate that TA is the endogenous ligand for the cloned TyrR. The affinity of various other biogenic amine receptors antagonists is tested to determine the pharmacological profile of TyrR. The tested drugs demonstrated a potency rank order of decreasing affinity as follows: yohimbine>phentolamine>chlorpromazine>mianserine (Table O).

TABLE O

| Chemical Agents | $K_i$ (uM) |
| --- | --- |
| Biogenic amines | |
| Tyramine (TA) | 1.27 ± 0.08 |
| Octopamine (OA) | 28.68 ± 0.78 |
| Dopamine (DA) | 57.47 ± 3.91 |
| Serotonin (SE) | 89.45 ± 9.01 |
| Histamine (His) | 193.50 ± 16.8 |
| Other ligands | |
| Yohimbine | 0.071 ± 0.001 |
| Phentolamine | 0.125 ± 0.020 |
| Chlorpromazine | 0.193 ± 0.050 |
| Mianserine | 0.280 ± 0.030 |

Inhibition constants of biogenic amines and certain receptor antagonists for competitive binding to TyrR. The inhibition constant (Ki) was determined using membranes from Schneider Drosophila cells that expressed TyrR. The Kis are reported as mean + standard deviation. ANOVA indicated statistically significant differences (p < 0.05) between all pairwise comparisons of biogenic amine Kis as well as other ligands Kis.

This potency order of tested drugs is in agreement with the potency order described by Saudou et al., (1990), supra. Yohimbine is identified as specific antagonist for tyramine receptor from *Drosophila melanogaster* (Saudou et al., 1990, supra; Arakawa et al., 1990, supra) and *Bombyx mori* (Khan, et al., (2003) *Arch. Insect Biochem. Physiol.* 52:7-16). The pharmacology of this receptor does not agree with any of the other biogenic amine receptors cloned from Drosophila or in other insect species. In particular, the octopamine receptor cloned from *Periplaneta americana*, Pa oa$_1$ or from *Drosophila melanogaster*, OAMB (Bischof and Enan, 2004, supra), or octopamine receptor characterized in various insect preparation Evans (1981) *J. Physiol.* 318:99-122; Dudai, et al., (1982) *J. Neurochem.* 38:1551-1558; Guillen, et al., (1989) *Life Sci.* 45(7):655-662), did not display an affinity rank order similar to the current data.

Fractionation of an Insect-Repellent Plant Essential Oil

To generate fractions an insect-repellent plant essential oil to screen against the Dro-TyrR-expressing S2 cells, a sample of a plant essential oil is fractionated by column chromatography. A preparative-scale gravity column containing 90-230-mesh silica gel adsorbent in 5% acetonitrile/95% hexanes is first prepared by mixing a slurry of silica gel in 5% acetonitrile/95% hexanes and transferring the slurry into a glass chromatography column. The slurry is allowed to settle and the solvent allowed to drain from the column until its level reaches the top of the silica gel. On top of the packed silica, a 5-ml volume of the plant essential oil is gently added. The column is allowed to drain until the level of the loaded plant essential oil reaches the top of the silica. Two column volumes of 5% acetonitrile/95% hexane elution solvent are then loaded into the top of the column, and the column is allowed to drain by gravity flow, while 5-ml fractions are collected. When the elution solvent nearly reaches the top of the silica, the column is then eluted stepwise with 1 column volume each of 10% acetonitrile/90% hexane, 20% acetonitrile/80% hexane, 30% acetonitrile/70% hexane, 40% acetonitrile/60% hexane, and 50% acetonitrile/50% hexane, while 5-ml fractions are collected throughout. The volume of the collected fractions is reduced to approximately 500 µl each with rotary evaporation.

Competitive Tyramine Receptor Binding Assay

Aliquots of the plant essential oil column fractions are then screened against the Drosophila tyramine receptor using the competitive tyramine receptor binding assay. To perform this assay, membranes containing Dro-TyrR are first isolated from Dro-TyrR-expressing S2 cells generated as described above. All steps are performed at 4° C. or on ice. Dro-TyrR-expressing S2 cells grown in Drosophila media are harvested in the same media by scraping from the dishes and then rinsing dishes with PBS. The cells are centrifuged at 1000 g for 3 min, washed once with PBS and centrifuged again as previously described. The cells are suspended in ice cold hypotonic buffer (10 mM Tris-Cl, pH 7.4), incubated on ice for 10 min, and lysed using a glass dounce homogenizer and tight glass pestle (Kontes Glass Co., Vineland, NJ) with 10 strokes. Nuclei are pelleted by centrifugation at 600 g for 5 min. The supernatant is decanted and centrifuged at 30,000 g for 30 min to pellet a crude membrane fraction. The pellet is suspended in binding buffer (50 mM Tris-Cl, 5 mM MgCl$_2$, pH 7.4). Protein concentration is determined by the Bradford Assay (Bio-Rad Laboratories, Hercules, CA). Membranes are frozen on dry ice then stored at −75° C. in aliquots.

The effect of the plant essential oil or fractions thereof on tyramine binding by the tyramine receptor is then determined by incubating 10-50 µg membrane protein and 4 nM H-tyramine with various dilutions of either the plant essential oil or a specific fraction thereof, and repeating the incubation, termination and detection steps of the assay. Binding data is analyzed by Scatchard plots using the software GraphPad Prism (San Diego, CA), using the log of the reciprocal dilution factor of the plant essential oil or specific fraction as a proxy for the exact molar concentration of the tested competitive ligand. All binding analyses are performed 3 times with duplicate samples in each assay.

Intracellular Calcium Assay

Figure 25:
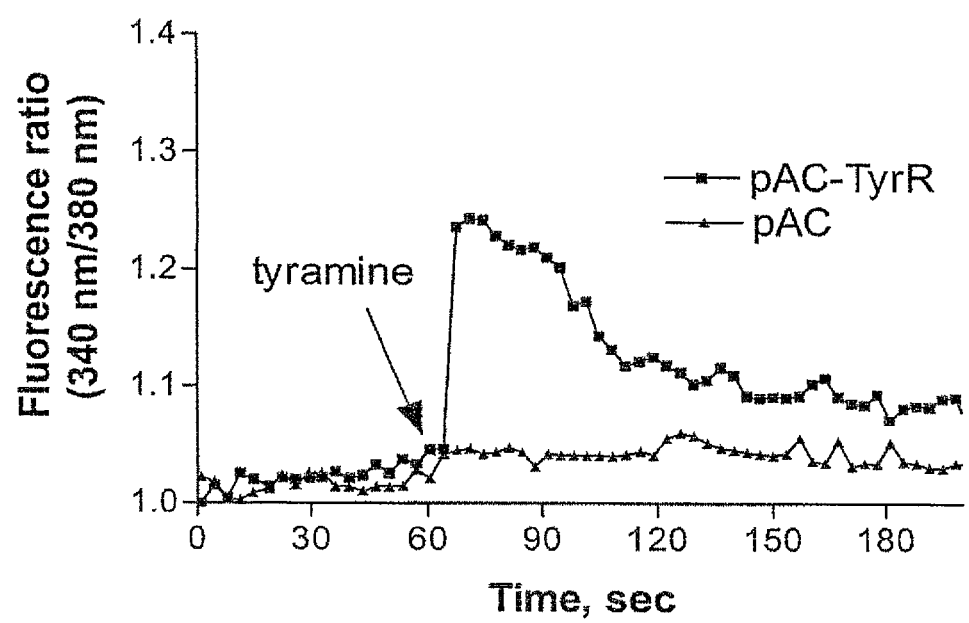
FIG. 25 is a graph showing the effect of tyramine on intracellular calcium levels ("[Ca$^{2+}$],") in S2 cells that are transfected with a plasmid encoding a tyramine receptor ("pAC-TyrR") or with an empty vector control plasmid ("pAC").

When a ligand binds to a biogenic amine receptor, this results in G-protein-mediated activation of Phospho-Lipase C (PLC), which cleaves phospho-inositol phosphate (PIP2) to form diacyl-glycerol (DAG) and inositol triphosphate (IP3). Increased cytoplasmic concentrations of IP3 induce release of Ca2+ from the endoplasmic reticulum. A pest control chemical, such as deltamethrin (DM), can affect signaling downstream of the biogenic amine receptor. To screen fractions of the plant essential oil for their ability to activate receptor-mediated increases in intracellular calcium levels, the fluorescence of the calcium-responsive, cell permeant dye Fura-2 AM in Dro-TyrR-expressing S2 cell samples is measured following incubation of the cells with each of the fractions. In Dro-TyrR-expressing S2 cells pre-incubated with Fura-2 AM, a sharp increase in $Ca^{2+}$-bound Fura-2 AM fluorescence is observed shortly after the addition of 1 µM tyramine (FIG. 25). This response is dependent on TyrR, as no $Ca^{2+}$ increase is observed in cells transfected with control plasmid pAC lacking the TyrR gene. To perform this assay with the plant essential oil fractions, S2 cells stably transfected with pAC-TyrR are grown in culture dishes, washed once with insect saline, collected by scraping, and suspended at $1 \times 10^6$ cells/ml in insect saline buffer with 5 µM Fura-2 AM. Cells are incubated at 23° C. for 1 hr in the dark, centrifuged, suspended in 1 ml insect saline buffer, and used immediately for calcium measurements. The fluorescence of $Ca^{2+}$-bound Fura-2 AM is measured as a function of time following the addition of a sample of a specific plant essential oil fraction. Control cells given the same treatment, except for the presence of a plant essential oil fraction, are tested in parallel. A spectrofluorometer with Felix software from Photon Technology International (Lawrenceville, NJ) is used for the fluorescence measurements and data collection. Cells are also incubated with the plant essential oil in parallel to compare calcium release induced by the unfractionated oil with that induced by specific fractions. Four separate trials for each test sample are performed. Data are normalized by dividing each value by the background fluorescence at the beginning of the assay before adding the test sample.

To determine if an increase in intracellular $Ca^{2+}$ in response to cell treatment with a plant essential oil fraction is specifically mediated by the tyramine receptor, the Fura-2 AM fluorescence assay is repeated with S2 cells transfected with pAC, therefore lacking the endogenous tyramine receptor, as described above. The plant essential oil fractions that induce an increase in $Ca^{2+}$-bound Fura-2 AM in Dro-TyrR-expressing S2 cells, but not in cells lacking TyrR, contain ingredients which specifically effect tyramine receptor signaling.

Receptor-Mediated cAMP Production Assay

Aliquots of the plant essential oil column fractions are also screened for their ability to modulate tyramine receptor-mediated activation of cAMP production.

Twenty four hours before cell treatment, 300,000 cells from the pAC-TyrR-stably transfected S2 cell line demonstrating the highest binding affinity to $^3$H-tyramine and control (untransfected) cells are plated in 1 ml media with 25 µg blasticidin/ml into 12 well dishes (4.5 cm$^2$). For cell treatment, the media is aspirated and 1 ml PBS with 300 µM IBMX (3-isobutyl-1-methylxanthine) and the test reagent is added. For each column chromatography fraction of the plant essential oil, cells are incubated at 23° C. in the presence and absence of the fraction. A sample of cells is also incubated with the unfractionated plant essential oil in parallel. After 10 min incubation, the PBS is aspirated and cells are incubated with 70% ethanol for 12 hours at −20° C. The cellular debris is centrifuged, and then the supernatant is removed and lyophilized to dryness. The amount of cAMP in the extract is determined by using a cAMP binding protein from the $^3$H-cAMP Biotrak Assay System (Amersham Biosciences, Piscataway, NJ) as per the manufacturer's instructions. Cell treatment is performed 3 times with duplicates at each concentration. Specific tyramine receptor-mediated activation of cAMP production by individual plant essential oil fractions is indicated by a lack of cAMP production in control untransfected cells given identical treatment. To determine the levels of cAMP produced in the cell independent of increases in intracellular calcium, the cells are incubated with 20 µM BAPTA/AM to chelate the intracellular calcium 10 min before the addition of TA.

Example 19

Generating an Improved Agent Against a Target Pest by Selective Recombination of Plant Essential Oil Fractions Fractions of plant essential oils that are screened for their ability to bind and activate the Drosophila tyramine receptor as described in Example 18 are recombined according to their specific activity. Fractions with specific activity that are elevated as compared to the unfractionated oil are recombined, while fractions with lower or negligible specific activity compared to the unfractionated oil are not recombined with other fractions, or are recombined in proportionally smaller quantities. The activity of the recombined fractions in the competitive inhibition tyramine binding assay, intracellular calcium release assay, and cAMP production assay, each of which is described in Example 18, is compared to that of the unfractionated oil to confirm that the specific activity of the agent is increased following fractionation and recombination.

Example 20

Determining Toxicity Against *Drosophila melanogaster* Fly Insects and Test Agents

*Drosophila melanogaster* (wild type) is purchased from Carolina Biological Supply Company (Burlington, NC). The tyramine receptor mutant (TyrR$^{neo30}$) *Drosophila melanogaster* is obtained from Bloomington Drosophila Stock Center (stock #BL-10268). The mutant flies are constructed in which the insertion of a single P transposable element has caused a mutation in tyramine receptor; their phenotype includes olfaction defects. See e.g., Cooley, et al., (1988) *Science,* 239, 1121-1128. The responsible transposon is reported as P {hsneo}TyrRile$^{neo30}$, BDGP:1(3)neo30 as described on the flybase website (hyper text transfer protocol at flybase<dot>bio<dot>indiana<dot>edu/<dot>bin/fbidq<dot>htm?FBA10011043. Both Drosophila strains are maintained under standard laboratory conditions.

Toxicity Against *Drosophila melanogaster* Fly

To determine whether the cellular changes in pAC-TyrR cell model (clone #2) in response to treatment with unfractionated or fractionated and recombined essential oils correlate with their insecticidal activity, a toxicity bioassay is performed against the wild type *Drosophila melanogaster* fly. Solutions of unfractionated or fractionated and recombined plant essential oils are prepared at various dilutions in acetone and applied to flies by topical application. Three replicates, with 5 flies per replicate, are used for each concentration. Control flies are treated with the same volume (0.5 μl/fly) of acetone. Data are subjected to probit analysis to determine LD50 value for each chemical as described in Finney (1971) *Probit analysis,* 3rd edn. Cambridge University Press, London, 333. To determine whether the tyramine receptor is involved in the toxicity of tested plant essential oils, tyramine receptor mutant (TyrR$^{neo30}$) *Drosophila melanogaster* strain is topically treated with a dose equivalent to the determined LD$_{50}$ for wild type strain. The mortality is calculated 24 hrs after treatment. Three replicates and 5 insects per replicate are used for the bioassay of each chemical. This bioassay is repeated five times.

Example 21

Identification and Screening of Compounds in Plant Essential Oils to Determine Active Ingredients for Generating Improved Agents Against a Target Pest The compounds in a plant essential oil or specific fraction thereof are identified by analysis on a mass spectrometer linked directly to a gas-chromatography column (GC-MS). Each compound is identified by its characteristic mass spectrum, which matches a fingerprint mass spectrum in a library of such spectra that is a standard component of mass spectrometer analysis software.

The compounds identified in a plant essential oil or fraction thereof are obtained from commercial chemical suppliers and screened against Drosophila S2 cells expressing the tyramine receptor using the intracellular calcium release assay, as described in Example 18. In this case, fluorescence of Ca$^{2+}$-bound Fura-2 AM in Dro-TyrR-expressing S2 cell samples is measured following incubation of the cells with one of these specific compounds, instead of a plant essential oil fraction. The final concentration of each compound in the cell samples is between 10 μM and 10 μM. Control cells tested in parallel are given the same treatment, but are not incubated with a test compound. Four separate trials for each test compound are performed. Data are normalized by dividing each value by the background fluorescence at the beginning of the assay before adding the test compound.

Example 22

Comparison of Competitive Inhibition of Tyramine Binding to Tyramine Receptor by Compounds Identified in Plant Essential Oils Compounds that trigger specific tyramine receptor-mediated changes in intracellular Ca$^{2+}$ levels are tested for their ability to interact with the tyramine receptor by examining their ability to competitively inhibit tyramine binding by the tyramine receptor, as described in Example 18. Plasma membranes from Dro-TyrR-expressing S2 cells are isolated as described. The effect of each specific compound on tyramine binding by the tyramine receptor is then determined by incubating 10-50 μg membrane protein and 4 nM $^3$H-tyramine with individual compounds, and repeating the incubation, termination and detection steps of the assay. Control experiments are performed with membrane protein and 4 nM $^3$H-tyramine alone to determine the fraction of tyramine bound to the tyramine receptor in the absence of an added compound identified in the plant essential oil. Binding data is analyzed by Scatchard plots using the software GraphPad Prism (San Diego, CA). All binding analyses are performed 3 times with duplicate samples in each assay. The degree to which individual compounds inhibit tyramine binding correlates with the affinity that the compounds have for the tyramine receptor.

Example 23

Insect Toxicity of Specific Compounds Identified in a Plant Essential Oil

The insect toxicity of specific, isolated compounds identified in a plant essential oil is tested in *Drosophila melanogaster* using the toxicity test described in Example 20. Solutions of individual compounds obtained after their identification in a plant essential oil are prepared in acetone and applied to individual flies by topical application. Three replicates, with 5 flies per replicate, are used for each concentration. Control flies are treated with the same volume (0.5 μl/fly) of acetone. Data are subjected to probit analysis to determine LD$_{50}$ value for each chemical as described in Finney (1971) *Probit analysis,* 3$^{rd}$ edn. Cambridge University Press, London, 333. To determine whether the tyramine receptor is involved in the toxicity of tested compounds, tyramine receptor mutant (TyrR$^{neo30}$) *Drosophila melanogaster* strain is topically treated with a dose equivalent to the determined LD$_{50}$ for wild type strain. The mortality is calculated 24 hrs after treatment. Three replicates and 5 insects per replicate are used for the bioassay of each chemical. This bioassay is repeated five times.

Example 24

Generation of an Improved Agent Against a Target Pest by Combining Individual Compounds Identified in a Plant Essential Oil Two or more compounds that are identified in a plant essential oil and that exhibit toxicity against fruit flies in the assay described in Example 23 are combined to form a mixture. The ability of this mixture to induce intracellular Ca$^{2+}$ release is tested using the Ca$^{2+}$-release assay described in Example 18, and is compared to the activity of the unfractionated plant essential oil. The concentrations of the compounds are varied to determine the proportions that produce the greatest increase in intracellular Ca$^{2+}$ release over the unfractionated plant oil. These combinations of compounds are then tested in the toxicity assay to determine their lethality to Drosophila relative to each individual compound.

Example 25

Generation of an Improved Agent Against a Target Pest by Combining Individual Compounds Identified in Different Plant Essential Oils Two or more compounds that are identified in different plant essential oils and that trigger receptor-specific toxicity against fruit flies in the assay described in Example 23 are combined to form a mixture. The extent to which this mixture is able to trigger tyramine receptor-activated intracellular Ca$^{2+}$ release is tested using the Ca$^{2+}$ release assay described in Example 18, and is compared to the activity of each unfractionated plant essential oil in which the compounds are identified. The concentrations of the chemical derivative or analog compounds are varied to determine the proportions that produce the greatest increase in intracellular Ca$^{2+}$ release over unfractionated plant oil. These combinations of compounds are then tested in the toxicity assay to determine their lethality to Drosophila relative to each individual compound and relative to the unfractionated plant oil.

Example 26

Screening of Chemical Derivatives or Analogs of an Active Ingredient Compound of Plant Essential Oils Chemical derivatives and analogs of compounds identified and tested as described in Examples 21-23 are obtained and screened for their ability to mediate tyramine receptor-activated intracellular $Ca^{2+}$ release in multiwell assay plates. Fluorescence of $Ca^{2+}$-bound Fura-2 AM in Dro-TyrR-expressing S2 cell samples is measured following incubation of the individual cell samples with one of these specific compounds. The final concentration of each compound in the cell samples is between 10 µM and 10 µM. Control cells tested in parallel are given the same treatment, but are not incubated with a test compound. Four separate trials for each test compound are performed. Data are normalized by dividing each value by the background fluorescence at the beginning of the assay before adding the test compound. S2 control cells that do not express the tyramine receptor (stably transfected with the pAC vector not containing the Dro-TyrR gene) are tested in parallel to determine tyramine receptor specificity of increases in intracellular $Ca^{2+}$ triggered by test compounds.

Example 27

Generation of an Improved Agent Against a Target Pest by Combining Chemical Derivatives or Analogs of Compounds Identified in a Plant Essential Oil Two or more chemical derivatives or analogs of compounds that trigger receptor-specific toxicity against fruit flies in the assay described in Example 26 are combined to form a mixture. The level of tyramine receptor-activated intracellular $Ca^{2+}$ release that is triggered by this mixture is determined using the $Ca^{2+}$ release assay described in Example 18, and is compared to the level of receptor-activated intracellular $Ca^{2+}$ release triggered by the unfractionated plant essential oil in which the parent compounds were identified. The concentrations of the chemical derivative or analog compounds are varied to determine the proportions that produce the greatest increase in intracellular $Ca^{2+}$ release over the unfractionated plant oil. These combinations of compounds are then tested in the toxicity assay as described in Example 23 to determine their lethality to Drosophila relative to each individual compound and relative to the unfractionated plant oil.

Example 28

Generation of an Improved Agent Against a Target Pest by Combining Chemical Derivatives or Analogs of Compounds Identified in Different Plant Essential Oils Two or more chemical derivatives or analogs of compounds that are identified in different plant essential oils and that trigger receptor-specific toxicity against fruit flies in the assay described in Example 25 are combined to form a mixture. The extent to which this mixture is able to trigger tyramine receptor-activated intracellular $Ca^{2+}$ release is tested using the $Ca^{2+}$ release assay described in Example 18, and is compared to the activity of each unfractionated plant essential oil in which the parent compounds were identified. The concentrations of the chemical derivative or analog compounds are varied to determine the proportions that produce the greatest increase in intracellular $Ca^{2+}$ release over the unfractionated plant oils. These combinations of compounds are then tested in the toxicity assay to determine their lethality to Drosophila relative to each individual compound and relative to each unfractionated plant oil. An improved insecticide based on an insect-repelling plant essential The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the at least two active ingredients selected for the pest control composition, the target pest, and the amounts of the various ingredients present in the pest control composition. Various embodiments of the invention can specifically include or exclude any of these variations or elements.

In some embodiments, the numbers expressing quantities of ingredients, properties such as molecular weight, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

What is claimed is:

1. A pest control composition comprising:
   0.1 to 5 weight percent isopropyl myristate;
   0.01 to 1.0 weight percent beta-pinene;
   0.01 to 0.3 weight percent camphene;
   limonene; and
   mineral oil.

2. The pest control composition of claim 1, comprising 0.1 to 3 weight percent isopropyl myristate.

3. The pest control composition of claim 1, further comprising at least one of:
   alpha-pinene;
   camphor; and
   linalool.

4. The pest control composition of claim 1, further comprising alpha-pinene and linalool.

5. The pest control composition of claim 1, further comprising camphor and linalool.

6. The pest control composition of claim 1, further comprising alpha-pinene, camphor, and linalool.

7. The pest control composition of claim 2, further comprising at least one of:
   alpha-pinene;
   camphor; and
   linalool.

8. The pest control composition of claim 2, further comprising alpha-pinene and linalool.

9. The pest control composition of claim 2, further comprising camphor and linalool.

10. The pest control composition of claim 2, further comprising alpha-pinene, camphor, and linalool.

11. A pest control composition comprising:
    0.08 to 0.6 weight percent isopropyl myristate;
    0.01 to 1.0 weight percent beta-pinene;
    0.01 to 0.3 weight percent camphene;
    limonene; and
    mineral oil.

12. The pest control composition of claim 11, further comprising at least one of:
    alpha-pinene;
    camphor; and
    linalool.

13. The pest control composition of claim 11, further comprising alpha-pinene and linalool.

14. The pest control composition of claim 11, further comprising camphor and linalool.

15. The pest control composition of claim 11, further comprising alpha-pinene, camphor, and linalool.

16. A method for controlling a pest comprising:
    contacting a pest with a pest control composition comprising
    0.1 to 5 weight percent isopropyl myristate;
    0.01 to 1.0 weight percent beta-pinene;
    0.01 to 0.3 weight percent camphene;
    limonene; and
    mineral oil.

17. The method for controlling a pest of claim 16, wherein the pest control composition comprises 0.1 to 3 weight percent isopropyl myristate.

18. The method for controlling a pest of claim 16, wherein the pest control composition further comprises at least one of alpha-pinene, camphor, and linalool.

19. The method for controlling a pest of claim 16, wherein the pest control composition further comprises alpha-pinene and linalool.

20. The method for controlling a pest of claim 16, wherein the pest control composition further comprises alpha-pinene, camphor, and linalool.

21. The method for controlling a pest of claim 17, wherein the pest control composition further comprises at least one of alpha-pinene, camphor, and linalool.

22. The method for controlling a pest of claim 17, wherein the pest control composition further comprises alpha-pinene and linalool.

23. The method for controlling a pest of claim 17, wherein the pest control composition further comprises camphor and linalool.

24. The method for controlling a pest of claim 17, wherein the pest control composition further comprises alpha-pinene, camphor, and linalool.

25. The method for controlling a pest of claim 16, wherein the pest control composition comprises 0.08 to 0.6 weight percent isopropyl myristate.

26. The method for controlling a pest of claim 25, wherein the pest control composition further comprises alpha-pinene and linalool.

27. The method for controlling a pest of claim 25, wherein the pest control composition further comprises camphor and linalool.

28. The method for controlling a pest of claim 25, wherein the pest control composition further comprises alpha-pinene, camphor, and linalool.

* * * * *

SEQUENCE LISTING

```
Sequence total quantity: 2
SEQ ID NO: 1            moltype = DNA  length = 33
FEATURE                 Location/Qualifiers
misc_feature            1..33
                        note = synthetic polynucleotide
source                  1..33
                        mol_type = other DNA
                        organism = synthetic construct
SEQUENCE: 1
gccgaattca tgccatcggc agatcagatc ctg                                    33

SEQ ID NO: 2            moltype = DNA  length = 34
FEATURE                 Location/Qualifiers
misc_feature            1..34
                        note = synthetic polynucleotide
source                  1..34
                        mol_type = other DNA
                        organism = synthetic construct
SEQUENCE: 2
taatctagat caattcaggc ccagaagtcg cttg                                   34
```